(12) United States Patent
Amarchinta et al.

(10) Patent No.: US 10,286,142 B2
(45) Date of Patent: May 14, 2019

(54) SYRINGE PACKAGING SYSTEM INCLUDING OXYGEN ABSORBER

(71) Applicant: Becton, Dickinson and Company, Franklin Lakes, NJ (US)

(72) Inventors: Hemanth Amarchinta, Fair Lawn, NJ (US); Jennifer Vo, Franklin Lakes, NJ (US); Richard Giddes, Edison, NJ (US); Christopher Hilliard, Bath, NC (US); Yusuf O. Oni, Hackensack, NJ (US); Gerald Bonczynski, Columbus, NE (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 16/103,380

(22) Filed: Aug. 14, 2018

(65) Prior Publication Data
US 2018/0353675 A1    Dec. 13, 2018

Related U.S. Application Data

(60) Continuation of application No. 15/486,601, filed on Apr. 13, 2017, now Pat. No. 10,076,603, which is a (Continued)

(51) Int. Cl.
*A61M 5/00* (2006.01)
*A61M 5/31* (2006.01)
*B65D 81/26* (2006.01)

(52) U.S. Cl.
CPC .......... *A61M 5/002* (2013.01); *A61M 5/3129* (2013.01); *B65D 81/268* (2013.01);
(Continued)

(58) Field of Classification Search
CPC .......... A61M 5/00; A61M 5/002; A61M 5/31; A61M 5/3129; A61M 25/00;
(Continued)

(56) References Cited

U.S. PATENT DOCUMENTS 1,581,341 A    4/1926   Guinness
1,862,057 A *  6/1932   Lewis .................... A47G 19/24
                                              220/532
(Continued)

FOREIGN PATENT DOCUMENTS

JP    2008506439 A    3/2008
JP    2010506802 A    3/2010
WO    2011004137 A1   1/2011

*Primary Examiner* — Bryon P Gehman
(74) *Attorney, Agent, or Firm* — The Webb Law Firm

(57) ABSTRACT

A syringe packaging system that includes a packaging member defining a first compartment, a second compartment, and a third compartment that are in gaseous communication theretogether is disclosed. The first compartment is structured to receive a syringe barrel therein, the second compartment is structured to receive a plunger rod therein, and the third compartment is structured to receive an oxygen absorber therein. With the packaging member enclosing the syringe barrel, the plunger rod, and the oxygen absorber, the oxygen absorber is adapted to draw oxygen from within the syringe barrel and to absorb oxygen contained within at least one of the first compartment, the second compartment, and the third compartment of the packaging member. The syringe packaging system of the present disclosure also allows for reduced storage space of a syringe assembly.

10 Claims, 50 Drawing Sheets

Related U.S. Application Data division of application No. 14/481,057, filed on Sep. 9, 2014, now Pat. No. 9,656,016.

(60) Provisional application No. 61/933,071, filed on Jan. 29, 2014.

(52) U.S. Cl.
CPC ............... *A61M 2005/3123* (2013.01); *A61M 2005/3142* (2013.01)

(58) Field of Classification Search
CPC ........ A61M 25/002; A61M 2005/3123; B65D 25/04; B65D 81/26; B65D 81/267; B65D 81/268; B65D 81/266
USPC ......... 206/204, 205, 210, 564, 571; 220/532
See application file for complete search history.

(56) References Cited

U.S. PATENT DOCUMENTS

| | | | |
|---|---|---|---|
| 2,283,867 A | 5/1942 | Flosdorf et al. | |
| 2,634,856 A | 4/1953 | Perkins | |
| 3,545,607 A | 12/1970 | Keller | |
| 3,746,155 A | 7/1973 | Seeley | |
| 3,869,062 A | 3/1975 | Jaeschke et al. | |
| 4,421,235 A | 12/1983 | Moriya | |
| 4,497,406 A | 2/1985 | Takanashi | |
| 4,537,305 A | 8/1985 | Takanashi | |
| 4,872,553 A | 10/1989 | Suzuki et al. | |
| 4,936,314 A | 6/1990 | Kasai et al. | |
| 5,551,557 A | 9/1996 | Brooks et al. | |
| 5,806,681 A * | 9/1998 | Frisk | B65D 51/244 206/524.3 |
| 5,806,708 A * | 9/1998 | Schwab | A45C 11/008 220/378 |
| 6,007,529 A | 12/1999 | Gustafsson et al. | |
| 6,660,295 B2 | 12/2003 | Watanabe et al. | |
| 6,682,791 B2 | 1/2004 | McKnight | |
| 6,726,652 B2 | 4/2004 | Eakins et al. | |
| 7,000,770 B2 | 2/2006 | Clarke et al. | |
| 7,631,760 B2 | 12/2009 | Guelzow et al. | |
| 7,708,719 B2 | 5/2010 | Wilmot et al. | |
| 7,762,044 B2 | 7/2010 | Clarke et al. | |
| 7,875,015 B2 | 1/2011 | Pahlberg et al. | |
| 9,248,229 B2 * | 2/2016 | Devouassoux | A61M 5/002 |
| 9,333,288 B2 * | 5/2016 | Hilliard | A61M 5/002 |
| 2003/0106824 A1 | 6/2003 | Wilmot et al. | |
| 2005/0072958 A1 | 4/2005 | Powers | |
| 2008/0072992 A1 | 3/2008 | Baleriaux et al. | |
| 2008/0289984 A1 * | 11/2008 | Raven | A61M 5/002 206/364 |
| 2009/0157008 A1 | 6/2009 | Vitral | |
| 2010/0174268 A1 | 7/2010 | Wilmot et al. | |
| 2011/0079525 A1 | 4/2011 | Peck et al. | |
| 2011/0155621 A1 | 6/2011 | Lindquist et al. | |
| 2011/0217430 A1 | 9/2011 | Chau et al. | |
| 2011/0272310 A1 | 11/2011 | Tennican | |
| 2012/0037526 A1 | 2/2012 | Mulone et al. | |
| 2012/0143144 A1 | 6/2012 | Young | |
| 2013/0081974 A1 | 4/2013 | Hilliard et al. | |
| 2014/0262883 A1 | 9/2014 | Devouassoux et al. | |
| 2015/0273133 A1 | 10/2015 | Kerschbaumer et al. | |

* cited by examiner

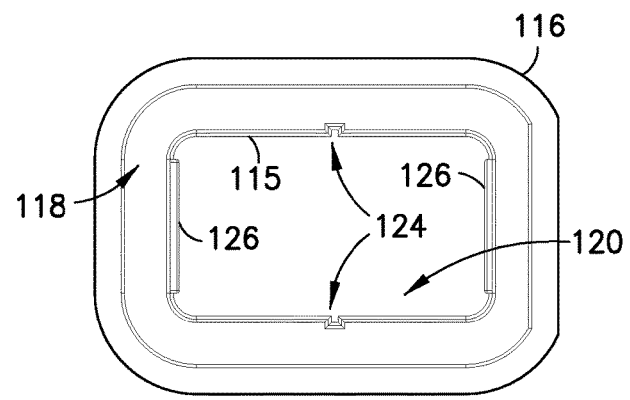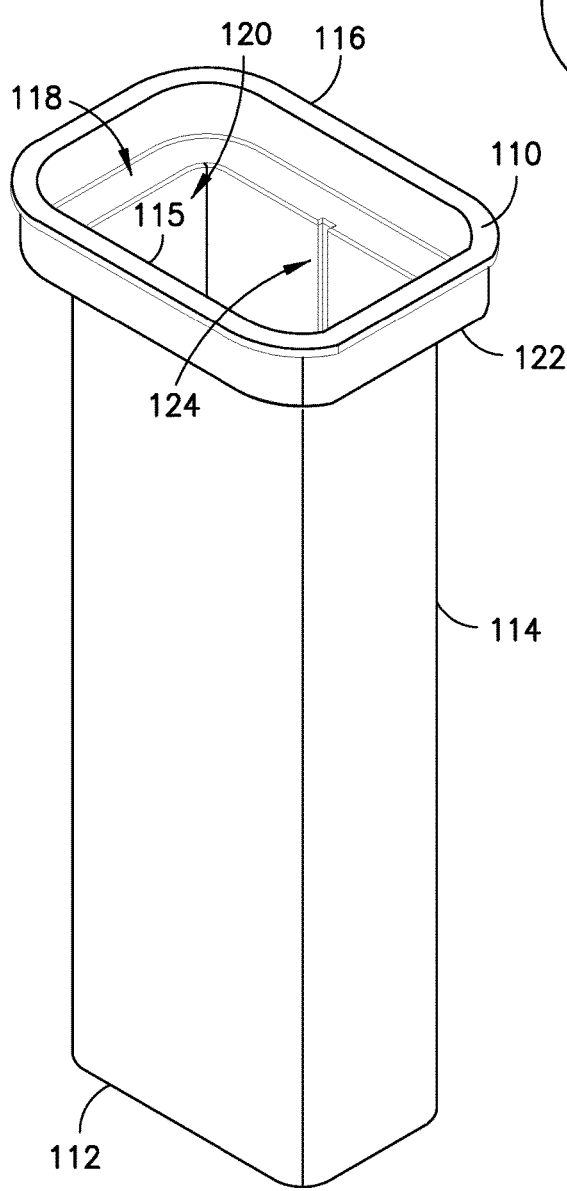

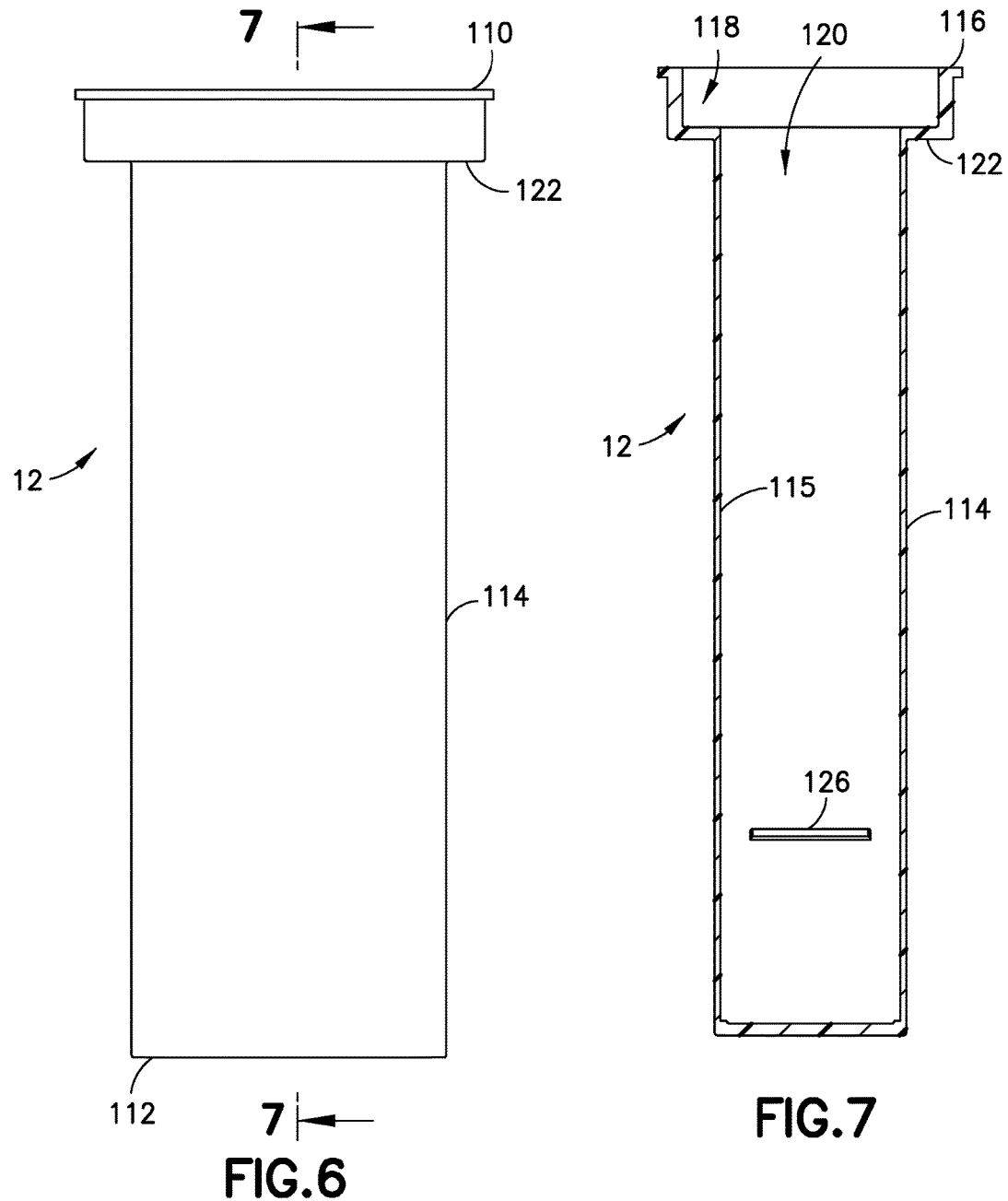

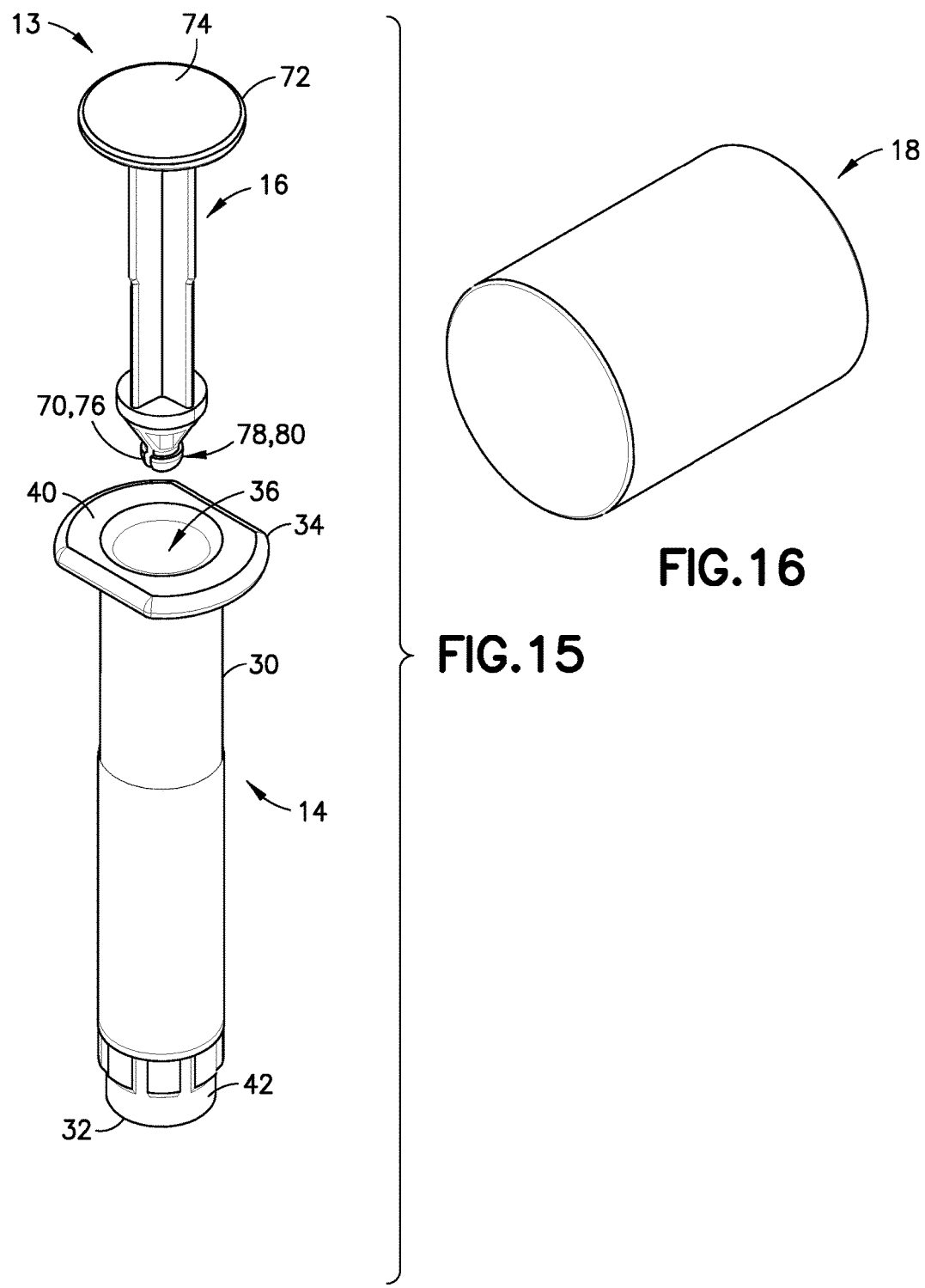

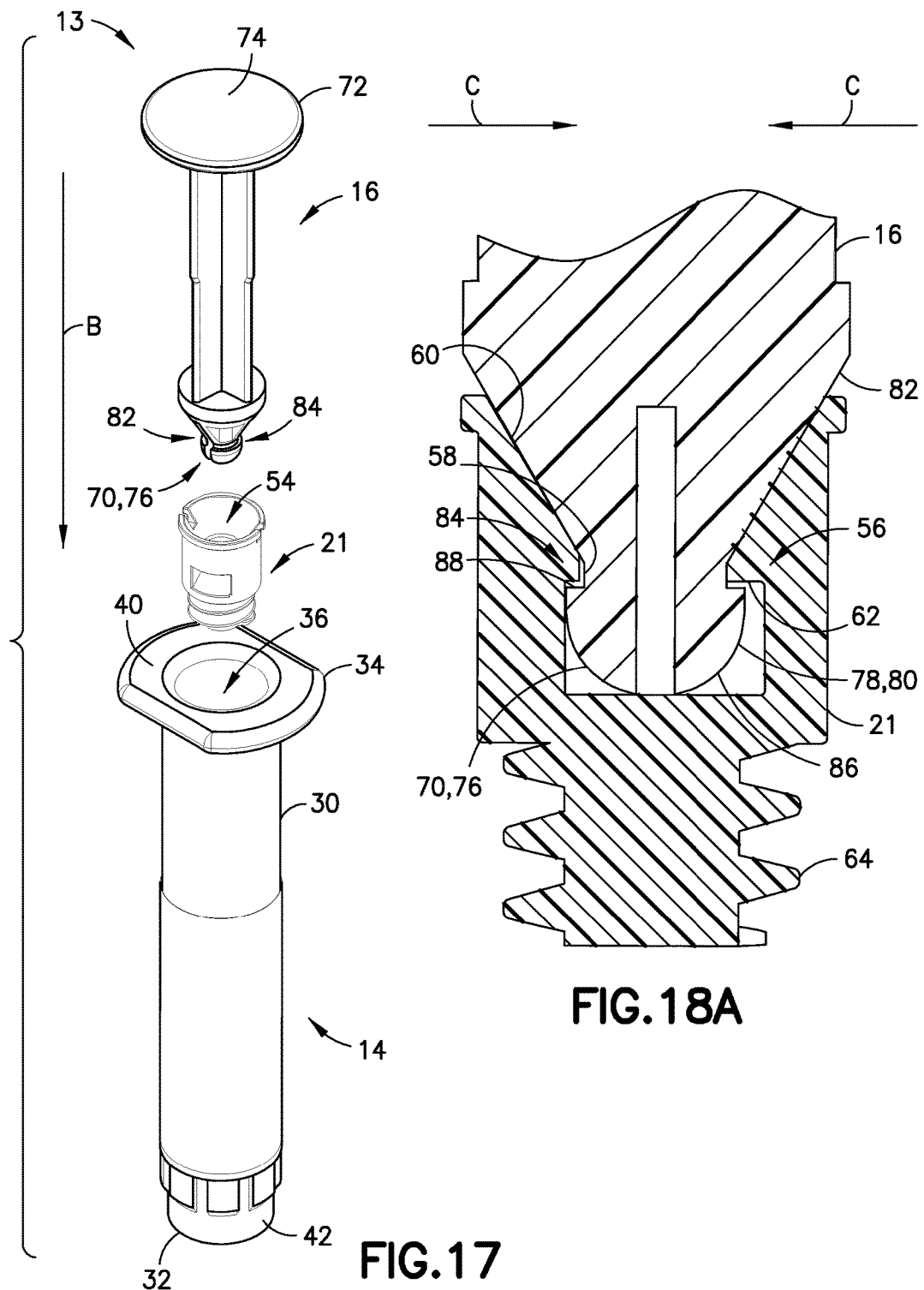

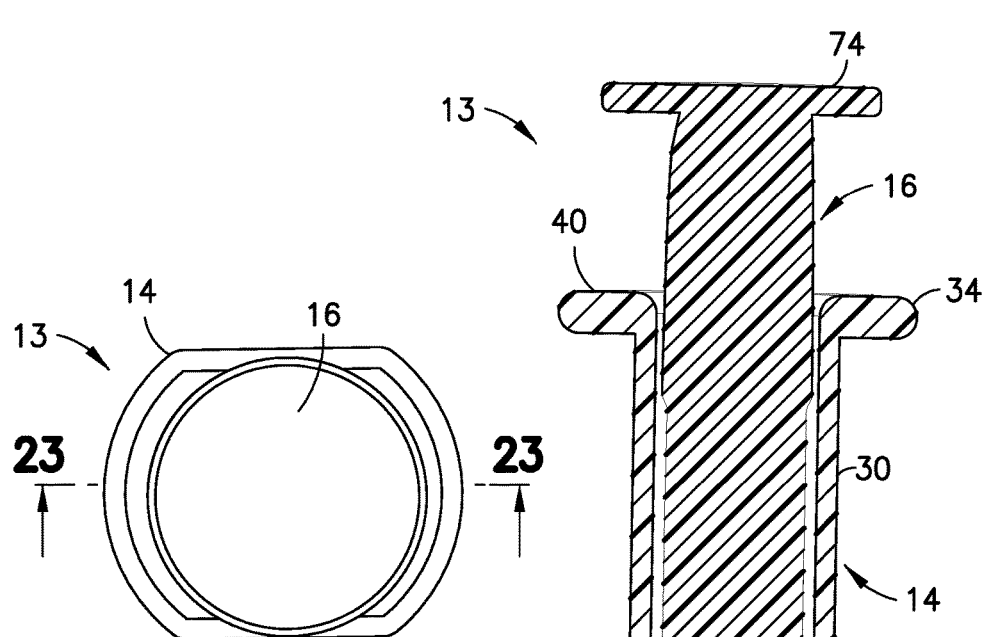
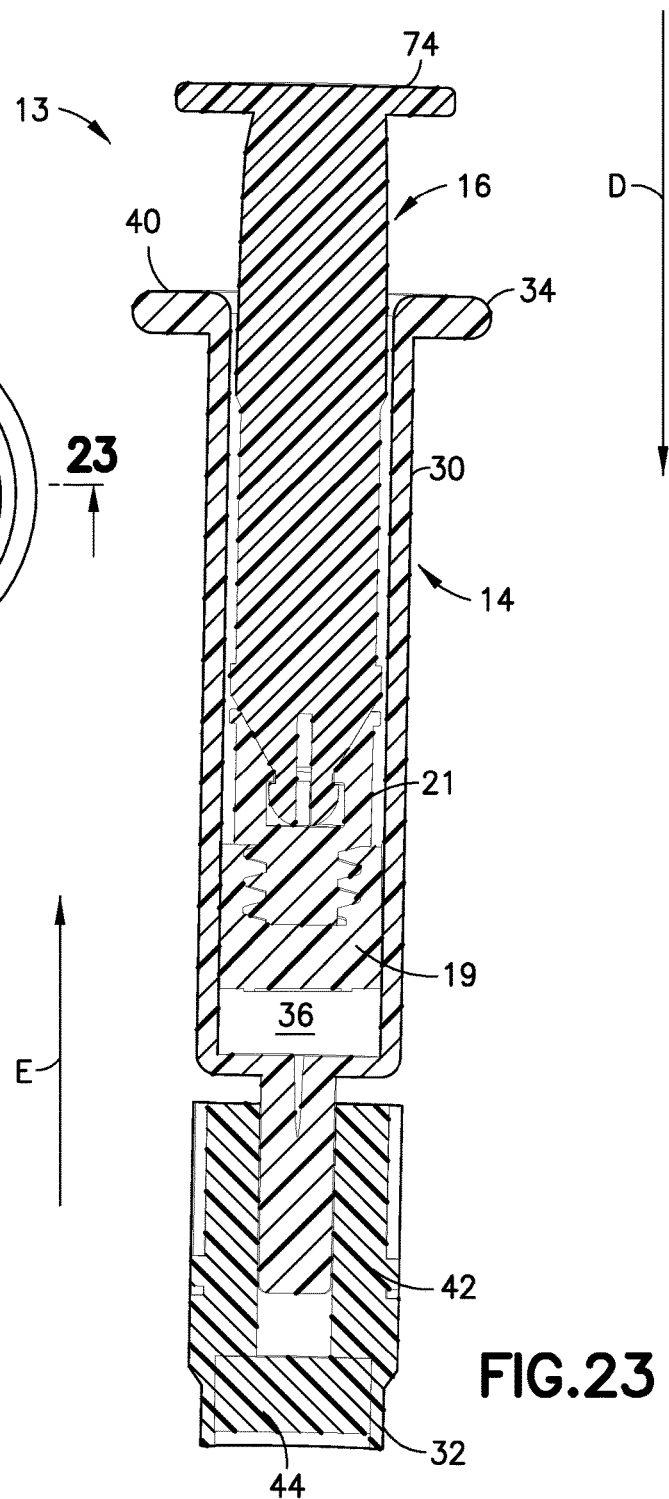
FIG.22
FIG.23

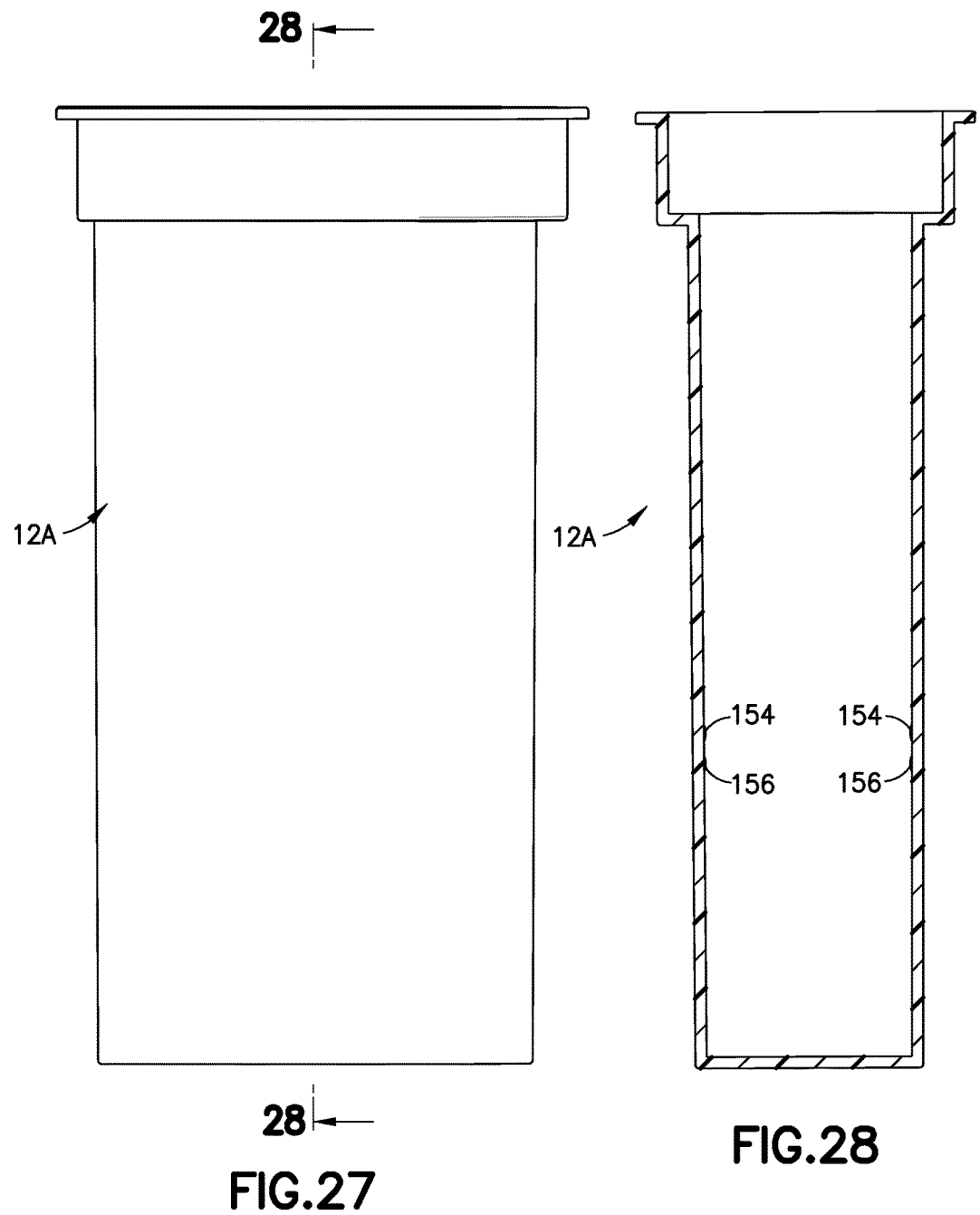

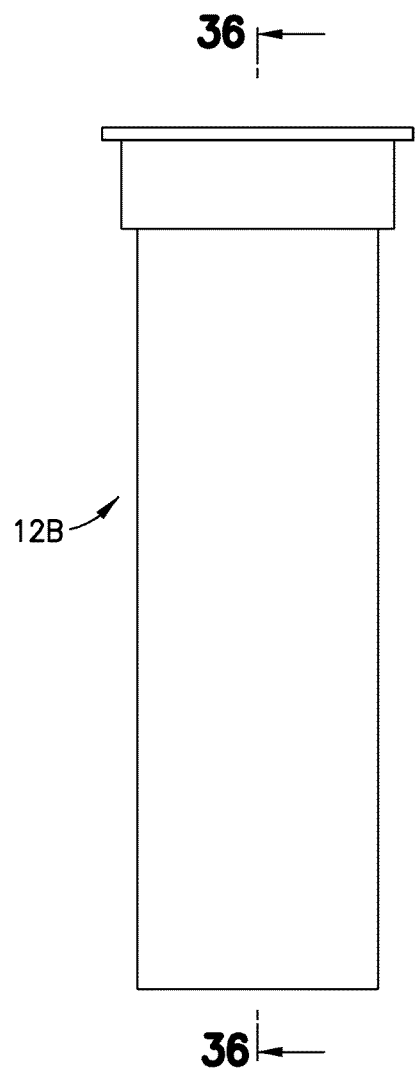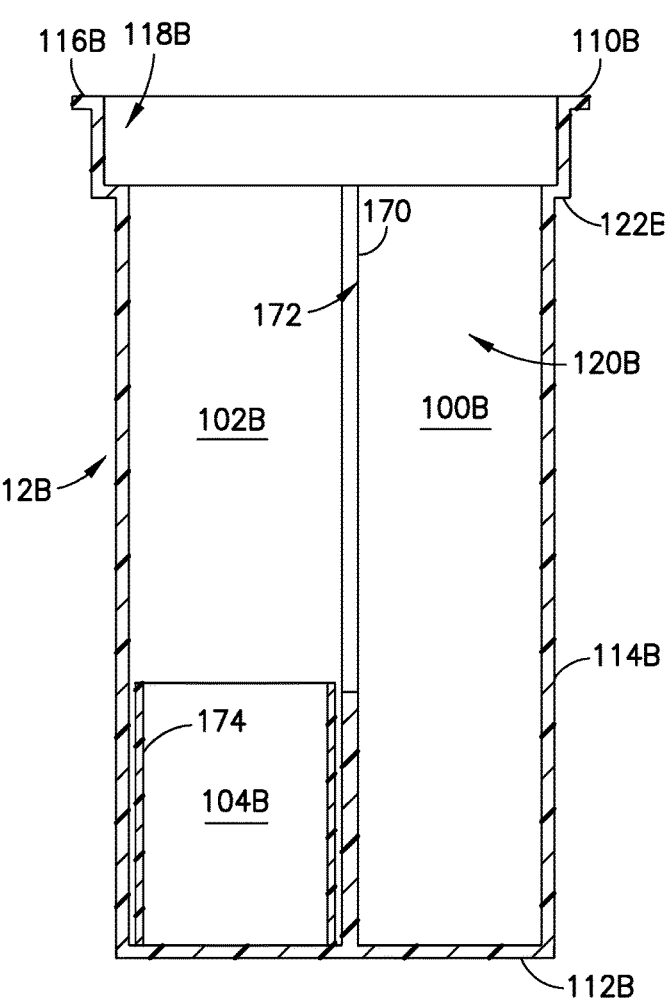
FIG.35
FIG.36

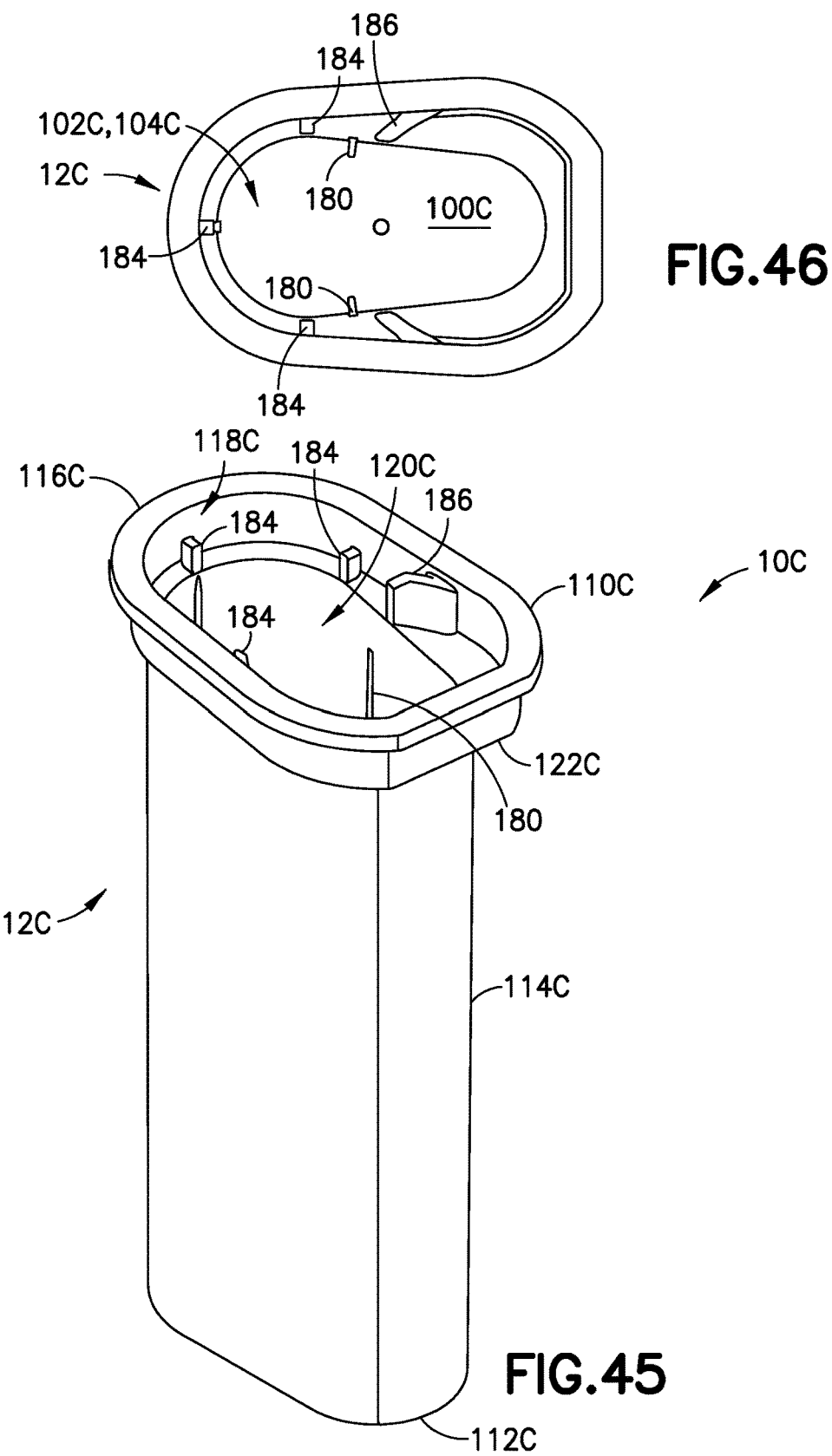

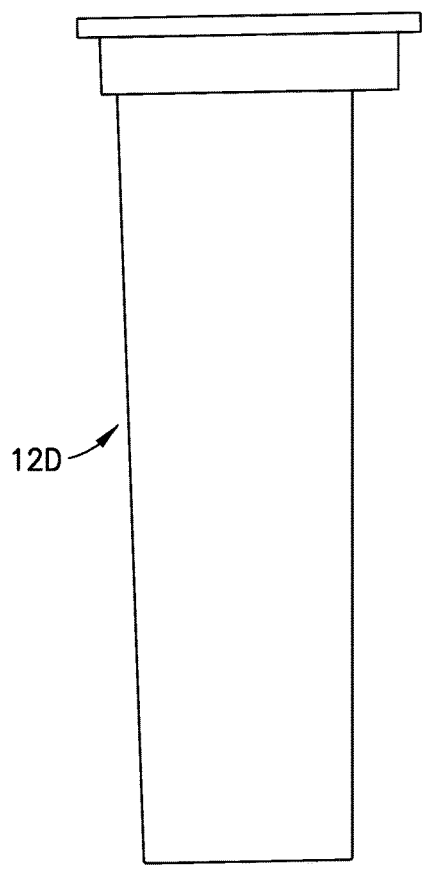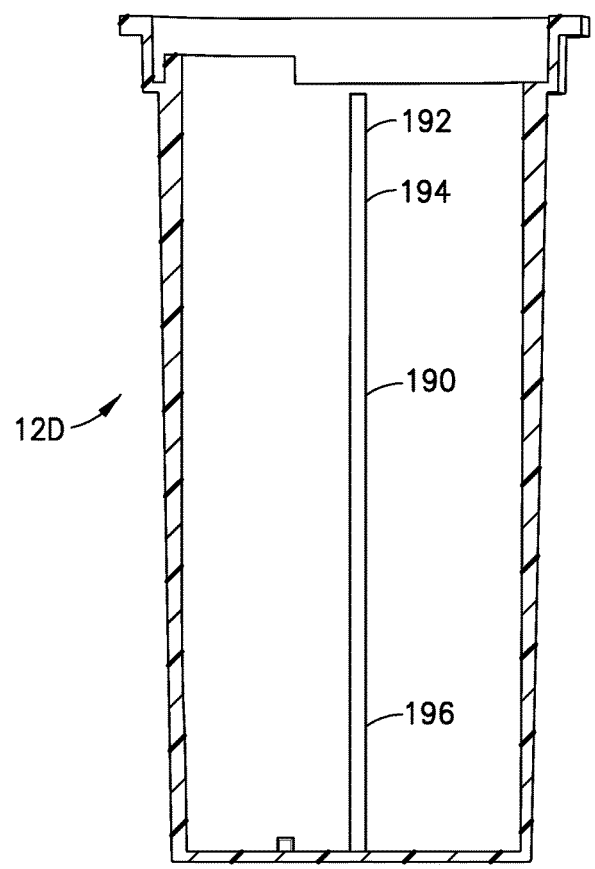
FIG.58
FIG.59

SYRINGE PACKAGING SYSTEM INCLUDING OXYGEN ABSORBER

CROSS-REFERENCE TO RELATED APPLICATION

This application is a continuation of U.S. application Ser. No. 15/486,601, filed on Apr. 13, 2017, which is a divisional of U.S. application Ser. No. 14/481,057, filed on Sep. 9, 2014 (now U.S. Pat. No. 9,656,016), which claims priority to U.S. Provisional Application No. 61/933,071, filed Jan. 29, 2014, the entire disclosure of each of which is hereby incorporated by reference.

BACKGROUND OF THE INVENTION

1. Field of the Disclosure

The present disclosure relates generally to a syringe assembly adapted for delivery of a fluid. More particularly, the present disclosure relates to a syringe assembly in which the plunger rod and the syringe barrel may be placed in a packaging enclosure in a manner that allows for reduced levels of oxygen within the packaging enclosure and reduced levels of oxygen contained in a fluid or drug disposed within the syringe barrel.

2. Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon application of a force to depress the plunger rod and stopper through the syringe barrel towards the front end of the syringe barrel, the contents of the syringe are thereby forced out of the syringe barrel through the opening at the front end for delivery to the patient.

Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery. However, packaging of such pre-filled syringes may include atmospheric gases such as oxygen within the packaging which can cause a medication or drug contained within the syringe barrel to degrade and which can reduce the shelf life of the pre-filled syringe assembly. Accordingly, there is a need for a syringe packaging that reduces oxygen levels therein.

SUMMARY OF THE INVENTION

In accordance with an embodiment of the present invention, a syringe packaging system includes a syringe barrel, a plunger rod, an oxygen absorber, and a packaging member. The packaging member defines a first compartment, a second compartment, and a third compartment, the first compartment, the second compartment, and the third compartment in gaseous communication. The first compartment is structured to receive the syringe barrel therein, the second compartment is structured to receive the plunger rod therein, and the third compartment is structured to receive the oxygen absorber therein. With the packaging member enclosing the syringe barrel, the plunger rod, and the oxygen absorber, the oxygen absorber is adapted to draw oxygen from within the syringe barrel and to absorb oxygen contained within at least one of the first compartment, the second compartment, and the third compartment of the packaging member.

In certain configurations, the syringe barrel includes a first end, a second end, and a sidewall extending therebetween and defining a chamber having an interior, the syringe barrel also includes a stopper slidably disposed within the interior of the chamber. The plunger rod may be engageable with a portion of the stopper. In certain configurations, the syringe packaging system includes a fluid disposed within the chamber of the syringe barrel.

With the packaging member enclosing the syringe barrel, the plunger rod, and the oxygen absorber, the oxygen absorber is adapted to draw oxygen from the fluid disposed within the chamber of the syringe barrel. In one configuration, the oxygen absorber is adapted to draw oxygen from the fluid disposed within the chamber through the stopper. In another configuration, the oxygen absorber is adapted to draw oxygen from the fluid disposed within the chamber through the syringe barrel.

The packaging member may also include a sealing member such that the packaging member and the sealing member enclose the syringe barrel, the plunger rod, and the oxygen absorber. The first compartment, the second compartment, and the third compartment may be formed as portions of a unitary compartment. In certain configurations, the syringe packaging system also includes a partition member receivable within the packaging member, the partition member and the packaging member defining the first compartment, the second compartment, and the third compartment. The partition member may define a plurality of gas holes allowing for gaseous communication between at least two of the first compartment, the second compartment, and the third compartment.

The packaging member may also include a sidewall defining opposing slots for receiving the partition member. The packaging member may optionally include at least one rib for engaging the oxygen absorber to secure the oxygen absorber within the packaging member. The packaging member may also include a support member for engaging the plunger rod to secure the plunger rod within the packaging member. Optionally, the packaging member may include a support member for engaging the syringe barrel to secure the syringe barrel within the packaging member.

In still other configurations, the packaging member may include a tapered portion of a sidewall for securing the oxygen absorber within the packaging member. The packaging member may also include a first protrusion and a second protrusion and the partition member may be at least partially receivable between the first protrusion and the second protrusion. The packaging member may also include a fin for engaging the oxygen absorber to secure the oxygen absorber within the packaging member. Optionally, the packaging member includes an internal wall for securing the oxygen absorber within the packaging member, and a lid having an aperture, with the lid securable to the internal wall. The oxygen absorber may include a polyolefin based material.

In accordance with another embodiment of the present invention, a syringe packaging system includes a syringe barrel having a first end, a second end, and a sidewall extending therebetween and defining a chamber having an interior. The syringe packaging system also includes a stopper slidably disposed within the interior of the chamber of the syringe barrel, and a fluid disposed within the chamber of the syringe barrel, wherein at least one of the syringe barrel and the stopper are formed of an oxygen permeable material. The syringe packaging system also includes a plunger rod engageable with a portion of the stopper and an oxygen absorber. The syringe packaging system further includes a packaging member formed of a generally oxygen impermeable material and defining a first compartment, a second compartment, and a third compartment, the first compartment, the second compartment, and the third compartment in gaseous communication. The first compartment is structured to receive the syringe barrel therein, the second compartment is structured to receive the plunger rod therein, and the third compartment is structured to receive the oxygen absorber therein. With the packaging member enclosing the syringe barrel, the plunger rod, and the oxygen absorber, the oxygen absorber is adapted to draw oxygen from the fluid disposed within the chamber of the syringe barrel and to absorb oxygen contained within the packaging member.

In certain configurations, the oxygen absorber is adapted to draw oxygen from the fluid disposed within the chamber through the stopper. In other configurations, the oxygen absorber is adapted to draw oxygen from the fluid disposed within the chamber through the syringe barrel.

The packaging member may include a sealing member, and the packaging member and the sealing member may enclose the syringe barrel, the plunger rod, and the oxygen absorber. The first compartment, the second compartment, and the third compartment may be formed as portions of a unitary compartment. Optionally, the packaging member may be formed of a polyester material or a polyamide material.

In accordance with yet another embodiment of the present invention, a syringe packaging system includes a syringe barrel, an oxygen absorber, and a packaging member defining a first compartment and a second compartment, with the first compartment and the second compartment in gaseous communication. The first compartment is structured to receive the syringe barrel therein and the second compartment is structured to receive the oxygen absorber therein. With the packaging member enclosing the syringe barrel and the oxygen absorber, the oxygen absorber is adapted to draw oxygen from within the syringe barrel.

In certain configurations, the syringe barrel includes a first end, a second end, and a sidewall extending therebetween and defining a chamber having an interior, the syringe barrel further includes a stopper slidably disposed within the interior of the chamber. In certain configurations, the syringe packaging system also includes a fluid disposed within the chamber of the syringe barrel. With the packaging member enclosing the syringe barrel and the oxygen absorber, the oxygen absorber may be adapted to draw oxygen from the fluid disposed within the chamber of the syringe barrel. The oxygen absorber may be adapted to draw oxygen from the fluid disposed within the chamber through the stopper. In other configurations, the oxygen absorber may be adapted to draw oxygen from the fluid disposed within the chamber through the syringe barrel.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 4 is a perspective view of a packaging member in accordance with an embodiment of the present invention.

FIG. 5 is a top view of a packaging member in accordance with an embodiment of the present invention.

FIG. 6 is a side elevation view of a packaging member in accordance with an embodiment of the present invention.

FIG. 7 is a cross-sectional view of a packaging member taken along line 7-7 of FIG. 6 in accordance with an embodiment of the present invention.

FIG. 15 is an exploded, perspective view of a syringe barrel and a plunger rod in accordance with an embodiment of the present invention.

FIG. 16 is a perspective view of an oxygen absorber in accordance with an embodiment of the present invention.

FIG. 17 is an exploded, perspective view of a syringe barrel, a stopper adapter, and a plunger rod in accordance with an embodiment of the present invention.

FIG. 18A is a fragmentary, cross-sectional view of the plunger rod and the stopper adapter in an engaged position in accordance with an embodiment of the present invention.

FIG. 22 is a top view of a syringe assembly in accordance with an embodiment of the present invention.

FIG. 23 is a cross-sectional view of a syringe assembly taken along line 23-23 of FIG. 22 in accordance with an embodiment of the present invention.

FIG. 27 is another side elevation view of a packaging member in accordance with an embodiment of the present invention.

FIG. 28 is a cross-sectional view of a packaging member taken along line 28-28 of FIG. 27 in accordance with an embodiment of the present invention.

FIG. 35 is a side elevation view of a packaging member in accordance with an embodiment of the present invention.

FIG. 36 is a cross-sectional view of a packaging member taken along line 36-36 of FIG. 35 in accordance with an embodiment of the present invention.

FIG. 45 is a perspective view of a packaging member in accordance with an embodiment of the present invention.

FIG. 46 is a top view of a packaging member in accordance with an embodiment of the present invention.

FIG. 58 is another side elevation view of a packaging member in accordance with an embodiment of the present invention.

FIG. 59 is a cross-sectional view of a packaging member taken along line 59-59 of FIG. 58 in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
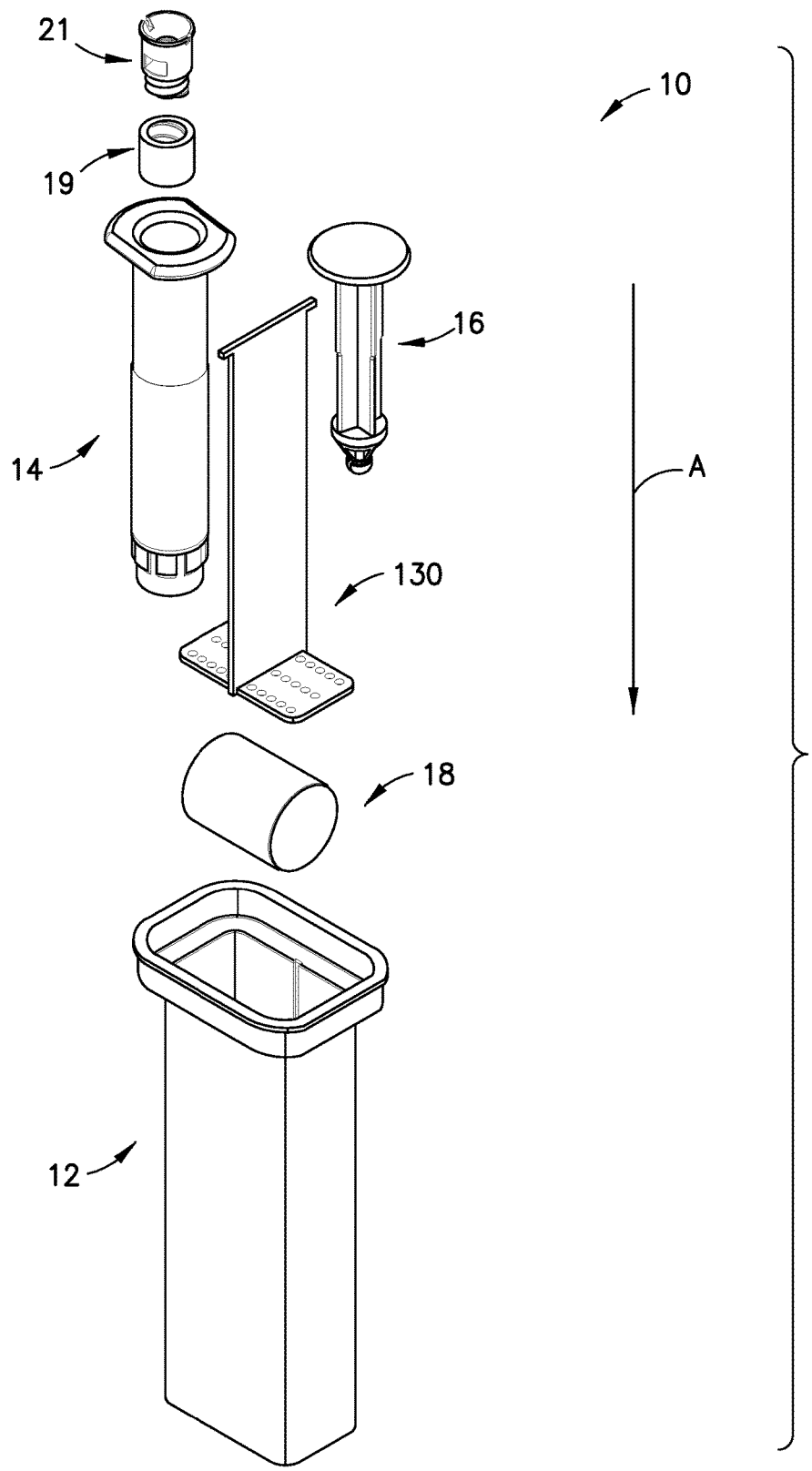
FIG. 1 is an exploded, perspective view of a syringe packaging system in accordance with an embodiment of the present invention.
Figure 2A:
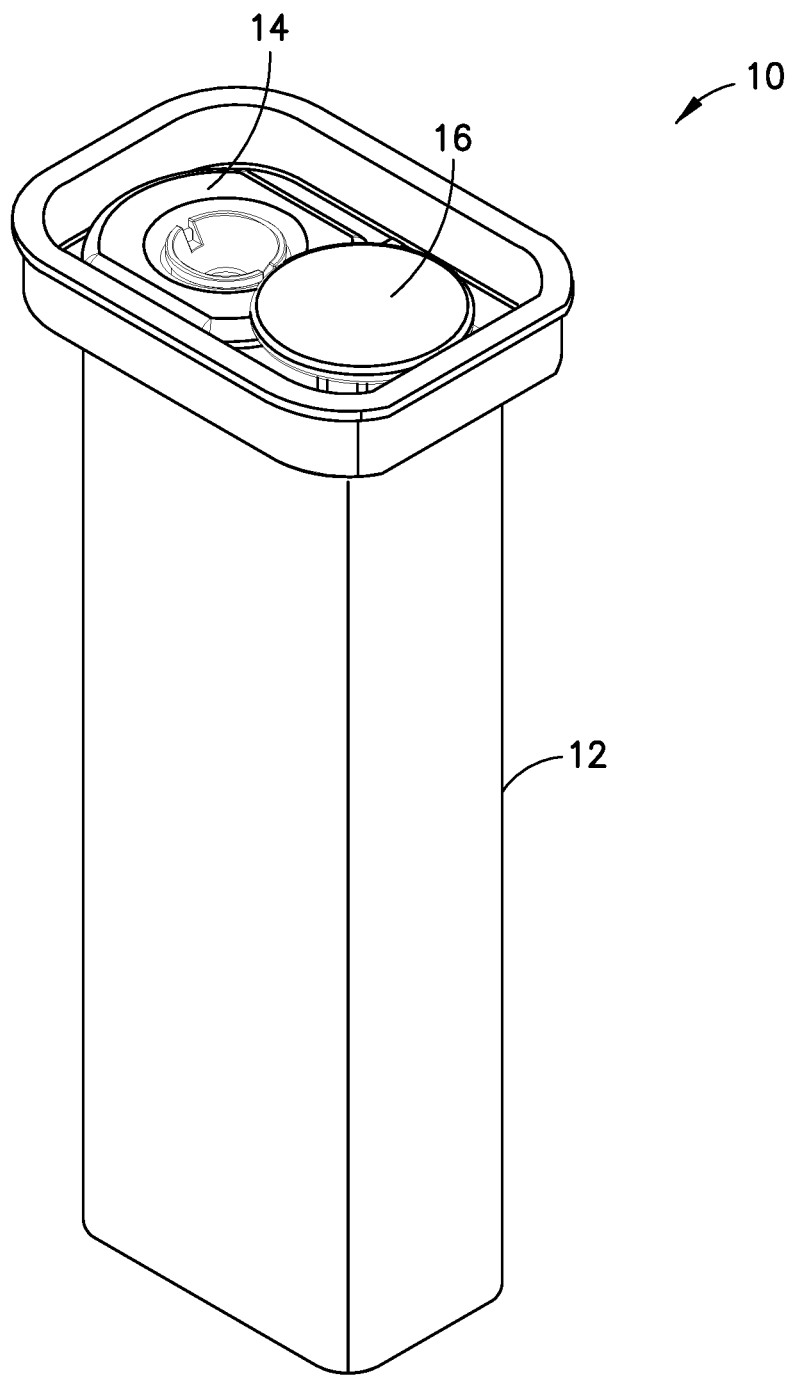
FIG. 2A is an assembled, perspective view of the syringe packaging system of FIG. 1 in accordance with an embodiment of the present invention.
Figure 2B:
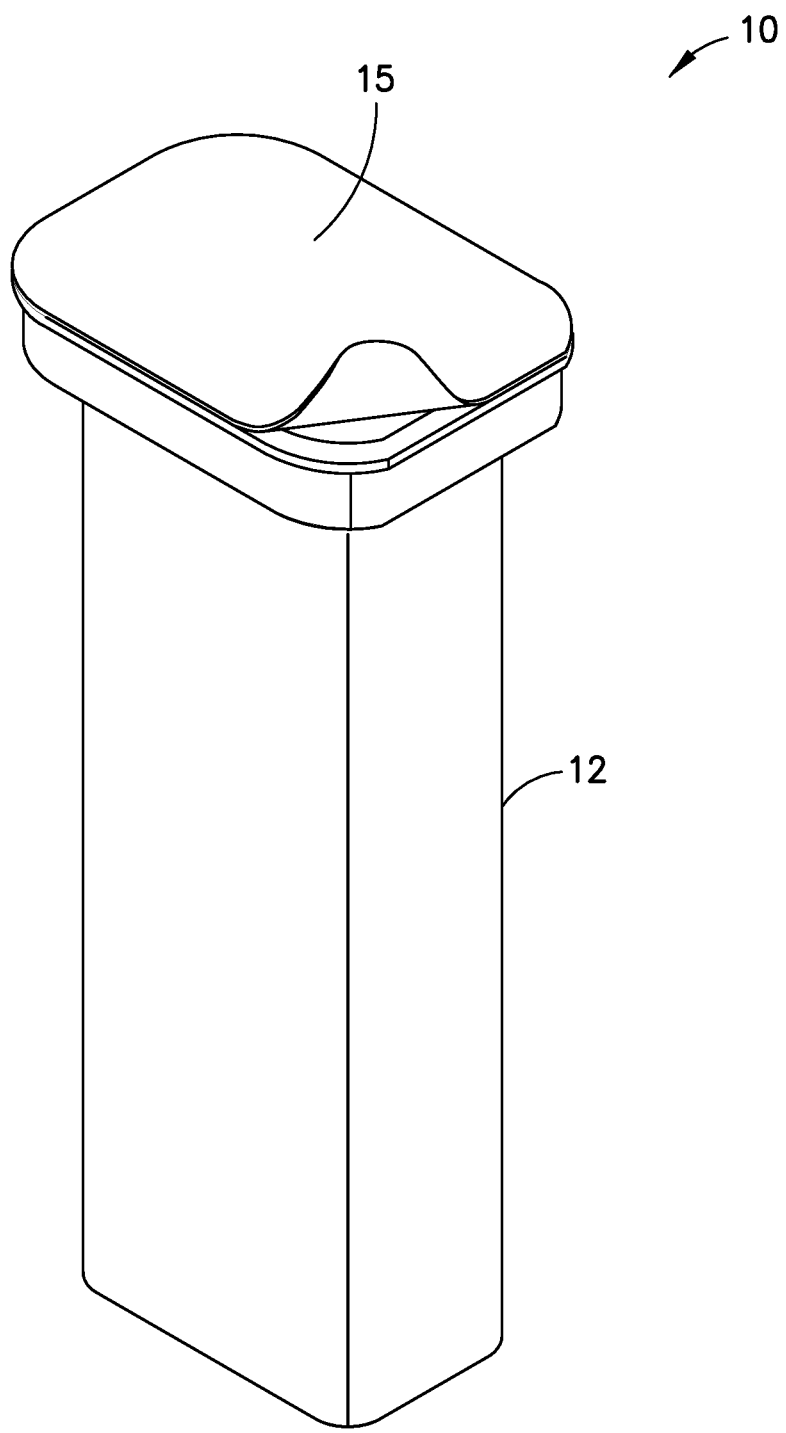
FIG. 2B is an assembled, perspective view of the syringe packaging system of FIG. 1, with a sealing member sealing the syringe packaging system in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

FIGS. 1-23 illustrate an exemplary embodiment of the present disclosure. Referring to FIGS. 1-9 and 15-23, a syringe packaging system 10 includes a packaging member 12, a syringe assembly 13 including a syringe barrel 14 and a detachable plunger rod 16, and an oxygen absorber 18. With the packaging member 12 enclosing the syringe barrel 14, the plunger rod 16, and the oxygen absorber 18, the oxygen absorber 18 is adapted to draw oxygen from the syringe barrel 14 and to absorb oxygen contained within the packaging member 12. The syringe packaging system 10 of the present disclosure also allows for reduced storage space of a syringe assembly.

Referring to FIGS. 1-3B, the packaging member 12 is sized and adapted to receive syringe barrel 14, plunger rod 16, and oxygen absorber 18 therein. Referring to FIGS. 15 and 17-23, in one embodiment, syringe assembly 13 includes syringe barrel 14, plunger rod 16, and a stopper assembly including a stopper 19 and a stopper adapter 21. Syringe assembly 13 may be adapted for dispensing and delivery of a fluid and/or collection of a fluid. For example, syringe assembly 13 may be used for injection or infusion of fluid such as a medication or drug into a patient. Syringe assembly 13 is contemplated for use in connection with a needle, such as by connecting syringe assembly 13 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

Referring to FIGS. 15 and 17-23, syringe barrel 14 generally includes a barrel body having a sidewall 30 extending between a first or distal end 32 and a second or proximal end 34. Sidewall 30 defines an elongate aperture or interior chamber 36 of syringe barrel 14. In one embodiment, interior chamber 36 may span the extent of syringe barrel 14 so that syringe barrel 14 is cannulated along its entire length. In one embodiment, syringe barrel 14 may be in the general form of an elongated cylindrical barrel as is known in the art in the general shape of a hypodermic syringe. In alternative embodiments, syringe barrel 14 may be in other forms for containing a fluid for delivery, such as in the general form of an elongated rectangular barrel, for example. Syringe barrel 14 may be formed of glass, or may be injection molded from thermoplastic material such as polypropylene and polyethylene according to techniques known to those of ordinary skill in the art, though it is to be appreciated that syringe barrel 14 may be made from other suitable materials and according to other applicable techniques. In certain configurations, syringe barrel 14 may include an outwardly extending flange 40 about at least a portion of proximal end 34. Flange 40 may be configured for easy grasping by a medical practitioner, as will be discussed herein.

Distal end 32 of syringe barrel 14 includes an outlet opening 38 (FIGS. 3A and 3B) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip for engagement with an optional separate tapered luer structure of such a separate device for attachment therewith (not shown). In one configuration, both the tapered luer tip and the separate tapered luer structure may be provided with the syringe assembly 13. In such a configuration, the separate tapered luer structure may be fitted with an attachment mechanism, such as a threaded engagement, for corresponding engagement with a separate device (not shown). In another configuration, the tapered luer tip may be provided for direct engagement with a separate device (not shown). In addition, a mechanism for locking engagement therebetween may also be provided with at least one of the tapered luer tip and/or the separate tapered luer structure, such as a luer collar or luer lock including interior threads. Such luer connections and luer locking mechanisms are well known in the art.

Proximal end 34 of syringe barrel 14 is generally open-ended, but is intended to be closed off to the external environment as discussed herein. Syringe barrel 14 may also include markings, such as graduations located on sidewall 30, for providing an indication as to the level or amount of fluid contained within interior chamber 36 of syringe barrel 14. Such markings may be provided on an external surface of sidewall 30, an internal surface of sidewall 30, or integrally formed or otherwise within sidewall 30 of syringe barrel 14. In other embodiments, alternatively, or in addition thereto, the markings may also provide a description of the contents of the syringe or other identifying information as may be known in the art, such as maximum and/or minimum fill lines.

Syringe barrel 14 may be useful as a pre-filled syringe, and, therefore, may be provided for end use with a fluid F (FIG. 3B), such as a medication or drug, contained within interior chamber 36 of syringe barrel 14, pre-filled by the manufacturer. In this manner, syringe barrel 14 can be manufactured, pre-filled with a medication, sterilized, and packaged in appropriate packaging such as packaging member 12 for delivery, storage, and use by the end user, without the need for the end user to fill the syringe with medication from a separate vial prior to use. In such an embodiment, syringe barrel 14 may include a tip cap or sealing cap member 42 including a seal 44 disposed at distal end 32 of syringe barrel 14 to seal a fluid F, such as a medication, within interior chamber 36 of syringe barrel 14.

As used herein, the term "drug" refers to a pharmaceutically active ingredient(s) and any pharmaceutical liquid composition containing the pharmaceutically active ingredient(s). Pharmaceutical liquid compositions include forms such as solutions, suspensions, emulsions, and the like. These pharmaceutical liquid compositions can be administered orally or by injection.

Any drug that is oxygen sensitive, i.e., can degrade as a result of exposure to oxygen, is suitable for incorporation into the pharmaceutical packaging systems described herein. Oxygen sensitive drugs include those that have amines either as salts or free bases, sulfides, allylic alcohols, phenols and other chemical groups that can have reactivity with oxygen. Non-limiting examples of oxygen sensitive drugs include morphine, hydromorphone, promethazine, dopamine, epinephrine, norepinephrine, esterified estrogen, ephedrine, pseudoephedrine, acetaminophen, ibuprofen, danofloxacin, erythromycin, penicillin, cyclosporine, methyldopate, cetirizine, diltiazem, verapamil, mexiletine, chlorothiazide, carbamazepine, selegiline, oxybutynin, vitamin A, vitamin B, vitamin C, L-cysteine, L-trytophan, and the like. In some embodiments, the packaging container, e.g., syringe barrel 14, of the pharmaceutical packaging systems described herein contain morphine. In other embodiments, the packaging container of the pharmaceutical packaging systems described herein contain hydromorphone. In further embodiments, the packaging container of the pharmaceutical packaging systems described herein contain promethazine.

The oxygen sensitive drugs in the pharmaceutical packaging systems described herein are stable in various storage conditions including ambient, intermediate, and accelerated conditions. Stability as used herein refers to a formulation meeting all stability criteria along its particular shelf life, as defined in the USP or equivalent monograph of the drug product (for the assay of the drug substance in particular) and the current stability criteria of the ICH Q3B guidance for impurities. All critical quality attributes need to stay in their acceptance range throughout the formulation's shelf life. As an example, for a morphine formulation to be stable, assay of the drug substance, i.e., morphine, is in the [90.0%-110.0%] range as per USP and per ICH Q3B guidelines, all known, i.e., identified, degradation products, such as pseudomorphine, hydroxymorphine, norphine-N-oxide, and the like, as well as unknown degradation products need to be no more than (NMT) 0.2%. Stability of the oxygen sensitive drugs in the pharmaceutical packaging systems described herein is assessed by HPLC, UPLC, or any other known analytical method.

In some embodiments an oxygen sensitive drug, when stored in the pharmaceutical packaging systems described herein, is stable in ambient conditions (e.g., 25° C./60% RH) for at least 12 months, at least 15 months, at least 18 months, or at least 24 months. In certain instances, an oxygen sensitive drug, when stored in the pharmaceutical packaging systems described herein, is stable in ambient conditions for at least 24 months. In other embodiments an oxygen sensitive drug, when stored in the pharmaceutical packaging systems described herein, is stable in intermediate conditions (e.g., 30° C./65% RH) for at least 6 months, at least 8 months, at least 10 months, or at least 12 months. In certain instances, an oxygen sensitive drug, when stored in the pharmaceutical packaging systems described herein, is stable in intermediate conditions for at least 12 months. In further embodiments, an oxygen sensitive drug, when stored in the pharmaceutical packaging systems described herein, is stable in accelerated conditions (e.g., 40° C./75% RH) for at least 4 months, at least 5 months, or at least 6 months. In certain instances, an oxygen sensitive drug, when stored in the pharmaceutical packaging systems described herein, is stable in accelerated conditions for at least 6 months.

The pharmaceutical packaging systems described herein are also suitable for pharmaceutical liquid compositions comprising an oxygen-sensitive excipient. Degradation of oxygen-sensitive excipients in a pharmaceutical composition can lead to a variety of effects ranging from discoloration of the composition, reduced performance or efficiency of the composition, and/or harmful reactivity with the active pharmaceutical ingredient. Nonexclusive examples of oxygen-sensitive excipients that benefit from the pharmaceutical packaging systems described herein include polyethylene oxide (PEO) or polyethylene glycol (PEG) and polyoxyethylene alkyl ethers.

In one embodiment, at least a portion of syringe barrel 14 such as sidewall 30, distal end 32, and/or proximal end 34 includes an oxygen permeable member such that oxygen may pass from chamber 36 of syringe barrel 14 to oxygen absorber 18 as will be described in more detail below. For example, in one embodiment, tip cap or cap member 42 may be formed of an oxygen permeable material so that oxygen may pass from chamber 36 of syringe barrel 14 to oxygen absorber 18. In one embodiment, cap member 42 may be formed of a cyclic olefin polymer which is oxygen permeable and appropriate for contact with fluid F. Further, it is contemplated that cap member 42 may be formed of other materials which are capable of allowing oxygen to pass from chamber 36 of syringe barrel 14 to oxygen absorber 18. In other embodiments, proximal end 34 or sidewall 30 of syringe barrel 14 may include and/or be formed of an oxygen permeable member so that oxygen may pass from chamber 36 of syringe barrel 14 to oxygen absorber 18.

Referring to FIGS. 17-23, syringe assembly 13 includes stopper 19 which is moveably or slidably disposed within interior chamber 36 of syringe barrel 14, and in sealing contact with the internal surface of sidewall 30 of syringe barrel 14. Stopper 19 is sized relative to syringe barrel 14 to provide sealing engagement with the interior surface of sidewall 30 of syringe barrel 14. Additionally, stopper 19 may include one or more annular ribs extending around the periphery of stopper 19 to increase the sealing engagement between stopper 19 and the interior surface of sidewall 30 of syringe barrel 14. In alternate embodiments, a singular O-ring or a plurality of O-rings may be circumferentially disposed about stopper 19 to increase the sealing engagement with the interior surface of sidewall 30 of syringe barrel 14.

Referring to FIGS. 17-23, in one embodiment, stopper 19 also includes a first or distal end 51 and a second or proximal end 53 defining a stopper adapter receiving aperture 55 formed therein and having a threaded portion 57 for securing stopper adapter 21 to stopper 19.

Referring to FIGS. 17-23, in one embodiment, stopper adapter 21 includes a first or distal end 50 and a second or proximal end 52 defining a plunger receiving aperture 54 formed therein and having a securement feature or engagement portion 56 for securing plunger rod 16 to stopper 19 via stopper adapter 21. In one embodiment, referring to FIGS. 17-23, the engagement portion 56 of stopper adapter 21 may include a protruding annular ring 58 having a tapered portion 60 and a locking end 62 as will be described in more detail below. In one embodiment, protruding annular ring 58 is formed of a rigid, unyielding material. In one embodiment, first end 50 of stopper adapter 21 includes a threaded portion 64.

Figure 18B:
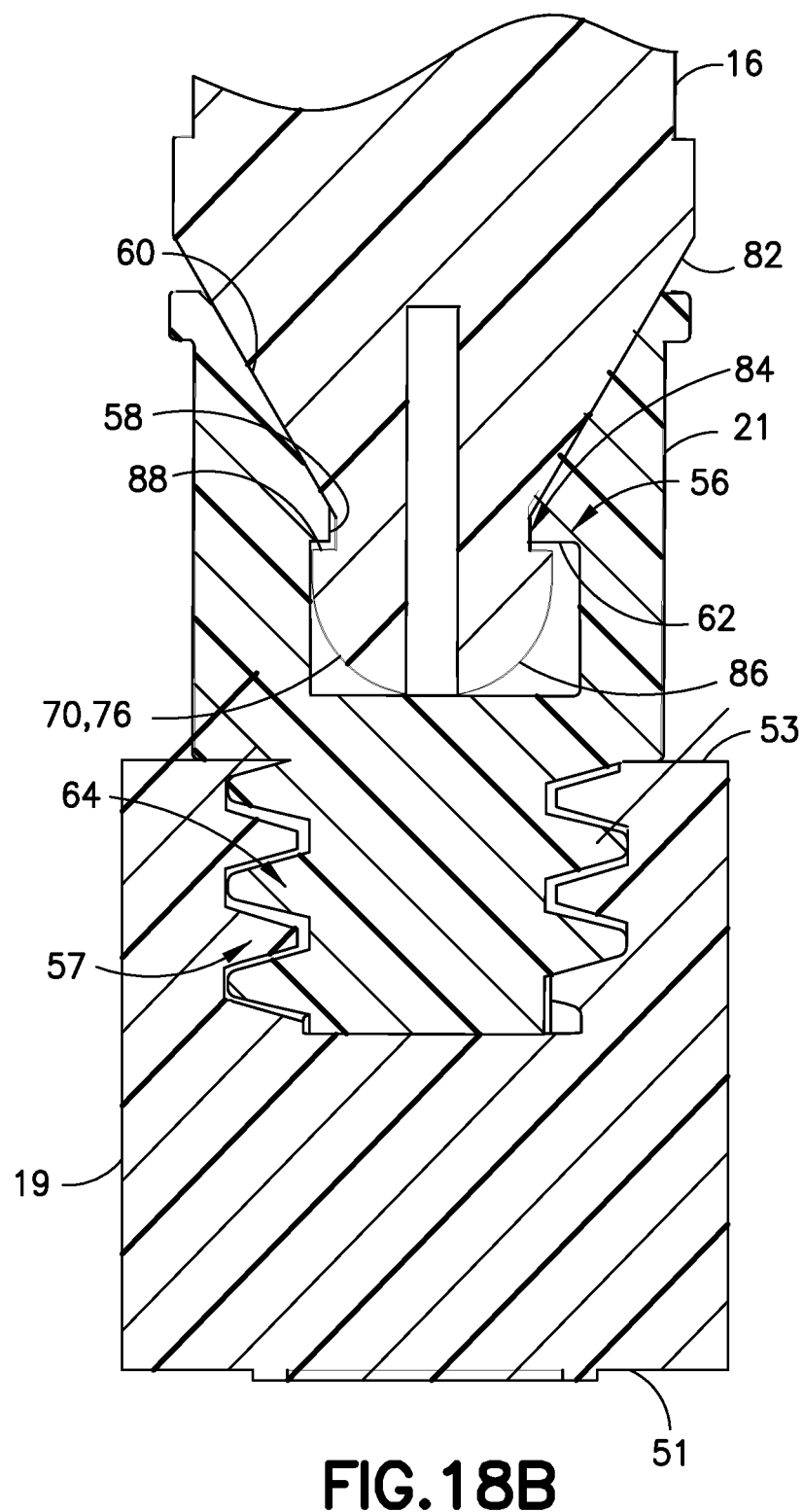
FIG. 18B is a fragmentary, cross-sectional view of the plunger rod and the stopper adapter in an engaged position and the stopper adapter and a stopper in an engaged position in accordance with an embodiment of the present invention.
Figure 19:
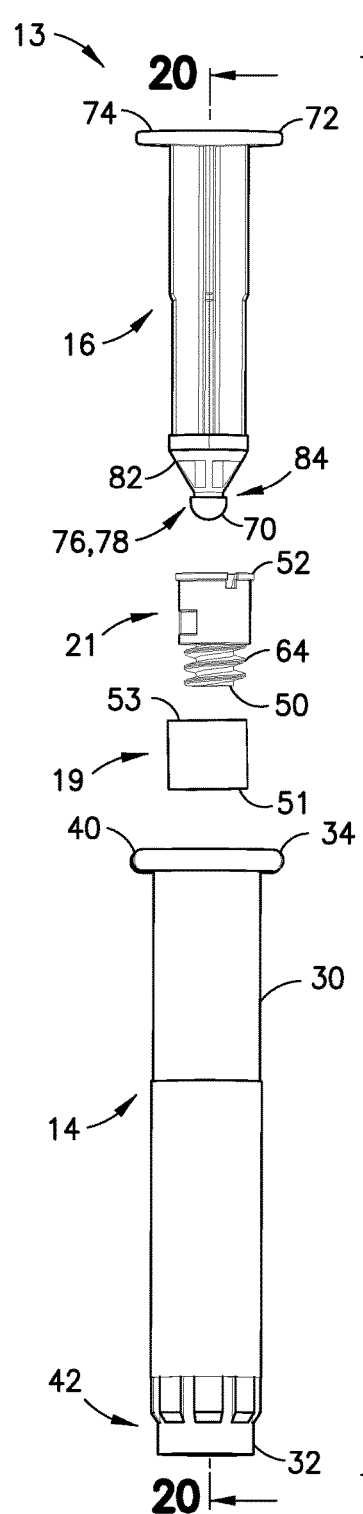
FIG. 19 is an exploded view of a syringe barrel, a stopper, a stopper adapter, and a plunger rod in accordance with an embodiment of the present invention.
Figure 20:
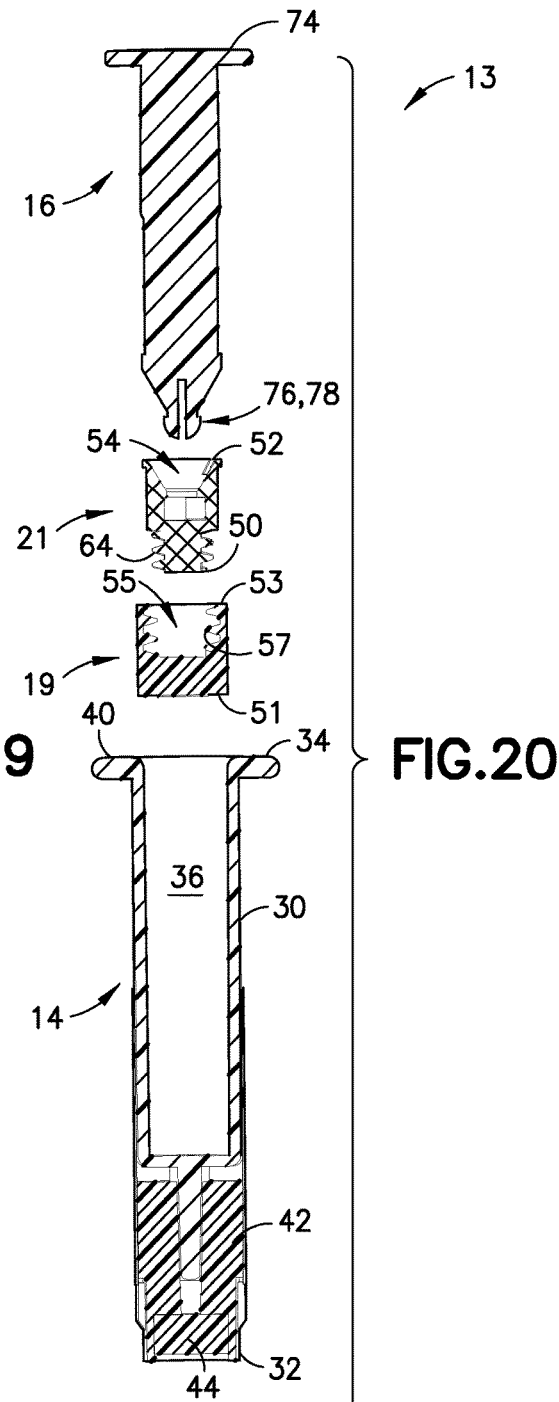
FIG. 20 is an exploded cross-sectional view of the syringe barrel, the stopper, the stopper adapter, and the plunger rod of FIG. 19 taken along line 20-20 in accordance with an embodiment of the present invention.

In one embodiment, stopper adapter 21 can be secured to stopper 19 by threadingly engaging threaded portion 64 of stopper adapter 21 to threaded portion 57 of stopper 19 as shown in FIG. 18B. In other embodiments, stopper adapter 21 can be secured to stopper 19 using a ball detent, locking tabs, spring loaded locking mechanism, latch, adhesive, or other similar mechanism. In all embodiments, stopper adapter 21 is locked, secured, or engaged to stopper 19, i.e., significant relative movement between stopper adapter 21 and stopper 19 is prevented. In other alternate embodiments, stopper adapter 21 and stopper 19 may be integrally formed and both form a stopper assembly.

In other embodiments, stopper adapter 21 and stopper 19 may be co-formed such as by co-extrusion. In alternate embodiments, stopper adapter 21 and stopper 19 may be integrally formed as a stopper assembly.

Referring to FIGS. 15 and 17-23, syringe assembly 13 further includes plunger rod 16 which provides a mechanism for dispensing fluid contained within interior chamber 36 of syringe barrel 14 through outlet opening 38 upon connection of plunger rod 16 to syringe barrel 14 via stopper adapter 21 as will be described in more detail below. Plunger rod 16 is adapted for advancing stopper 19. In one embodiment, plunger rod 16 is sized for movement within interior chamber 36 of syringe barrel 14 as will be discussed in more detail below, and generally includes a first or distal end 70, a second or proximal end 72, a flange 74 disposed adjacent second end 72, and a securement feature or engagement portion 76 for securing plunger rod 16 to stopper 19. In one embodiment, referring to FIGS. 17-23, the engagement portion 76 of plunger rod 16 may include a plunger rod head 78 having a deformable restraining member such as elastic fingers 80 and a neck 82 disposed adjacent plunger rod head 78. Plunger rod head 78 also includes an annular groove 84 located between elastic fingers 80 and neck 82. Elastic fingers 80 each include a tapered portion 86 and a locking end 88. Plunger rod head 78 will be described in more detail below.

In another embodiment, the engagement portion 56 of stopper adapter 21 may include a deformable restraining member, e.g., elastic fingers, for securing plunger rod 16 to stopper 19 via stopper adapter 21. In other embodiments, the engagement portion 56 of stopper adapter 21 may include a threaded portion, snap fit mechanism, a ball detent, locking tabs, spring loaded locking mechanism, latch, adhesive, or other similar mechanism for securing plunger rod 16 to stopper 19 via stopper adapter 21.

In another embodiment, the engagement portion 76 of plunger rod 16 may include a plunger rod head 78 formed of a rigid, unyielding material for securing plunger rod 16 to stopper 19 via stopper adapter 21. In other embodiments, the engagement portion 76 of plunger rod 16 may include a threaded portion, snap fit mechanism, a ball detent, locking tabs, spring loaded locking mechanism, latch, adhesive, or other similar mechanism for securing plunger rod 16 to stopper 19 via stopper adapter 21.

Referring to FIGS. 1-3B and 16, oxygen absorber 18 is included with the syringe packaging system 10 of the present disclosure. By disposing oxygen absorber 18 within packaging member 12, oxygen absorber 18 can reduce the oxygen levels within packaging member 12 and remove oxygen contained in fluid F (FIG. 3B) disposed within chamber 36 of syringe barrel 14. For example, any oxygen contained within packaging member 12 will be absorbed by oxygen absorber 18. Additionally, oxygen contained within chamber 36 of syringe barrel 14, and/or oxygen contained in fluid F disposed within chamber 36 of syringe barrel 14, will flow from chamber 36 of syringe barrel 14 to oxygen absorber 18 via the at least one portion of syringe barrel 14, such as sidewall 30, distal end 32, and/or proximal end 34 that includes an oxygen permeable member as described above. Reduction of oxygen levels within packaging member 12 is important because atmospheric gases such as oxygen contained in packaging member 12 and contained in fluid F disposed within chamber 36 of syringe barrel 14 can cause fluid F, such as a medication or drug in a pre-filled syringe, to degrade.

In one embodiment, oxygen absorber 18 may be formed of a polyolefin based material, e.g., a polypropylene material or a polyethylene material, or a similar material to allow for the desired oxygen absorption rate or kinetics. In one embodiment, oxygen absorber 18 may be formed of iron, low molecular weight organic compounds such as ascorbic acid and sodium ascorbate, and polymeric materials incorporating a resin and a catalyst. Further, it is contemplated that oxygen absorber 18 may be formed of other materials which are capable of absorbing oxygen contained within packaging member 12 and removing oxygen contained in fluid F disposed within chamber 36 of syringe barrel 14. In some embodiments, suitable materials for oxygen absorbers include metal-based substances that remove oxygen by reacting with it by chemical bonding, generally forming a metal oxide component. Example oxygen absorbers suitable for use in the present system are disclosed in U.S. application Ser. No. 14/207,207, the entire disclosure of which is hereby incorporated by reference herein. Metal-based substances include elemental iron as well as iron oxide, iron hydroxide, iron carbide, and the like. Other metals for use as oxygen absorbers include nickel, tin, copper, and zinc. Metal-based oxygen absorbers are typically in the form of a powder to increase surface area. Powder formation of the metal-based oxygen absorbers is by any known method including, but not limited to, atomization, milling, pulverization, and electrolysis. Additional materials for oxygen absorbers include low molecular weight organic compounds such as ascorbic acid, sodium ascorbate, catechol and phenol, activated carbon, and polymeric materials incorporating a resin and a catalyst. In some embodiments of the pharmaceutical packaging system, the oxygen absorber is a metal-based oxygen absorber. In certain instances of the pharmaceutical packaging system, the oxygen absorber is an iron-based oxygen absorber. In further instances of the pharmaceutical packaging system, the oxygen absorber is an iron-based oxygen absorber in the form of a canister.

In one embodiment, referring to FIGS. 1, 3A, 3B, and 16, oxygen absorber 18 is in the form of a canister. In other embodiments, oxygen absorber 18 may be in other forms such as in the form of a packet or sachet. In some embodiments, oxygen absorber 18 may be a cylindrical shape, a capsular shape, or a similar shape to allow for the desired absorption rate or kinetics. In this manner, the size, shape, cross-sectional area, and/or volume of oxygen absorber 18 and the position of oxygen absorber 18 within packaging member 12 may be varied so that oxygen absorber 18 is adapted to absorb oxygen contained within packaging member 12 and is also adapted to remove oxygen contained in fluid F disposed within chamber 36 of syringe barrel 14 to prevent fluid F from degrading and to increase the shelf life of syringe packaging system 10.

The packaging systems described herein are useful for enhancing stability and preventing oxidative degradation of oxygen sensitive drugs in liquid form thereby allowing for extended product shelf life and prolonged drug potency or efficiency.

"Oxygen-sensitive" or "oxygen-sensitivity" refers to the ability of a substance to react with oxygen under ambient temperature conditions (e.g., 5° C. to about 40° C.). The chemical reaction may involve the addition of an oxygen atom to the substance, removal of a hydrogen from the substance, or the loss or removal of one or more electrons from a molecular entity, with or without concomitant loss or removal of a proton or protons.

A feature of the pharmaceutical packaging systems herein is that the configuration allows the absorption and removal of oxygen in all the components of the system. In essence, the oxygen absorber in the pharmaceutical packaging system herein leads to the absorbance and removal of oxygen in the secondary packaging, e.g., packaging member 12, the primary packaging, e.g., syringe barrel 14, and the drug inside the primary packaging. The oxygen absorber further removes the low oxygen ingress through the secondary packaging over time. In this configuration, the residual oxygen amount that is present inside the primary and secondary packaging due to the pharmaceutical manufacturing process as well as the oxygen entering the packaging system from external environments over time, is reduced and even eliminated.

Another feature of the pharmaceutical packaging systems described herein is that the pharmaceutical packaging systems maintain zero % oxygen level after removal of the initial oxygen in the primary packaging container and secondary packaging for an extended period of time. As a result, the pharmaceutical packaging systems described herein offer increases in the shelf life of oxygen sensitive drugs past conventional packaging and methods such as from inert atmosphere packaging processes (e.g., nitrogen blanketing and/or degassing). In some embodiments, the pharmaceutical packaging systems described herein maintain zero % oxygen level in the primary and secondary packaging for at least about 12 months, at least about 15 months, at least about 18 months, at least about 24 months, at least about 30 months, at least about 36 months, at least about 48 months, or at least about 60 months. In certain instances, the pharmaceutical packaging systems described herein maintain zero % oxygen level in the primary and secondary packaging for at least 12 months. In certain instances, the pharmaceutical packaging systems described herein maintain zero % oxygen level in the primary and secondary packaging for at least 24 months. In certain instances, the pharmaceutical packaging systems described herein maintain zero % oxygen level in the primary and secondary packaging for at least 36 months.

In one embodiment, the oxygen absorber in the pharmaceutical packaging systems herein allows for the rapid uptake of oxygen present in the secondary packaging. Oxygen in air at ambient temperature and pressure (1 atm) is at a concentration of about 21%. When a pharmaceutical packaging system described herein is assembled in air in ambient conditions, the environment inside the secondary packaging is initially also at 21% oxygen level. The oxygen absorber in the pharmaceutical packaging system of the present disclosure quickly reduces the oxygen level in the secondary packaging to zero % in one to three days. Accordingly, in some embodiments, the oxygen absorber reduces oxygen to zero % in the secondary packaging in about seven days, in about six days, in about five days, in about four days, in about three days, in about two days, or in about one day after initial packaging of the assembly. In some embodiments, the oxygen absorber reduces oxygen to zero % in the secondary packaging in about one to seven days. In some embodiments, the oxygen absorber reduces oxygen to zero % in the secondary packaging in about one to three days. In some embodiments, the oxygen absorber reduces oxygen in the secondary packaging by about 35%, about 50%, about 60%, about 65%, about 70%, about 75%, about 80%, about 85%, about 90%, or about 95% of the total oxygen in the air per day after initial packaging of the assembly. In certain instances, the oxygen absorber reduces oxygen in the secondary packaging by about 50% per day. In other instances, the oxygen absorber reduces oxygen in the secondary packaging by about 75% per day. In further instances, the oxygen absorber reduces oxygen in the secondary packaging by about 90% per day. In other embodiments, the oxygen absorber reduces oxygen in the secondary packaging by about 35% to about 75%, about 50% to about 80%, or about 65% to about 90% per day after initial packaging of the assembly.

In further embodiments, the oxygen absorber reduces about 2 to about 10 cc of oxygen/day, atm; about 3 to about 8 cc of oxygen/day, atm; or about 4 to about 6 cc of oxygen/day, atm in the secondary packaging. In certain instances, the oxygen absorber reduces about 2, about 3, about 4, about 5, about 6, about 7, about 8, about 9, or about 10 cc of oxygen/day, atm in the secondary packaging. In some instances, the oxygen absorber reduces about 4 cc of oxygen/day, atm. In other instances, the oxygen absorber reduces about 6 cc of oxygen/day, atm. In further instances, the oxygen absorber reduces about 8 cc of oxygen/day, atm.

Another feature of the oxygen absorber is that it maintains zero % oxygen level after removal of the initial oxygen in the secondary packaging for an extended period of time. In some embodiments, the oxygen absorber maintains zero % oxygen level in the secondary packaging for the entire shelf life of the drug. In some embodiments, the oxygen absorber maintains zero % oxygen level in the secondary packaging for at least about 12 months, at least about 15 months, at least about 18 months, at least about 24 months, at least about 30 months, at least about 36 months, at least about 48 months, or least about 60 months. In certain instances, the oxygen absorber maintains zero % oxygen level in the secondary packaging for at least 12 months. In certain instances, the oxygen absorber maintains zero % oxygen level in the secondary packaging for at least 24 months. In certain instances, the oxygen absorber maintains zero % oxygen level in the secondary packaging for at least 36 months.

An advantageous feature of the oxygen absorber in the pharmaceutical packaging systems herein is the absorbance and removal of oxygen present in the primary packaging and in the liquid drug itself. It was found that the oxygen absorber in exemplary packaging systems also removed residual oxygen in the primary packaging and in the liquid over time to zero % oxygen level.

The oxygen absorber, in some embodiments, also maintains zero % oxygen level after removal of the initial oxygen in the primary packaging for an extended period of time. In some embodiments, the oxygen absorber maintains zero % oxygen level in the primary packaging for the entire shelf life of the drug. In some embodiments, the oxygen absorber maintains zero % oxygen level in the primary packaging for at least about 12 months, at least about 15 months, at least about 18 months, at least about 24 months, at least about 30 months, at least about 36 months, at least about 48 months, or at least about 60 months. In certain instances, the oxygen absorber maintains zero % oxygen level in the primary packaging for at least 12 months. In certain instances, the oxygen absorber maintains zero % oxygen level in the primary packaging for at least 24 months. In certain instances, the oxygen absorber maintains zero % oxygen level in the primary packaging for at least 36 months.

An interesting property of the pharmaceutical packaging systems herein is that after removal of oxygen in the primary and secondary packaging by the oxygen absorber, the air pressure in the secondary packaging environment achieves lower than atmospheric pressure, such that there is vacuum effect.

The capacity for absorbing oxygen for the oxygen absorbers of the pharmaceutical packaging systems described herein encompass the capacities sufficient to reduce the initial oxygen levels of the primary and secondary packaging to a zero % oxygen level at a rate as described in the previous embodiments and maintain the zero % oxygen level for a period of time as described in the previous embodiments. The oxygen absorbing capacity can be optimized according to the materials used in secondary packaging, the surface area of the secondary packaging and amount of initial oxygen in the secondary and primary packaging.

Referring to FIGS. 1-9, a syringe packaging system 10 includes a packaging member 12 formed of a generally oxygen impermeable material and a sealing member 15 (FIG. 2B) which may be removably attached to packaging member 12. Packaging member 12 is sized and adapted to receive each of syringe barrel 14, plunger rod 16, and oxygen absorber 18 therein as will be described in more detail below.

Sealing member 15 provides an additional mechanism to reduce oxygen levels within packaging member 12 by sealing syringe barrel 14, plunger rod 16, and oxygen absorber 18 within packaging member 12 as will be described in more detail below. In one embodiment, sealing member 15 may be formed of an aluminum based material to provide sufficient sealing with packaging member 12 as will be described below. In one embodiment, sealing member 15 may be formed of a generally oxygen impermeable material.

Referring to FIGS. 1-9, packaging member 12 is sized to receive syringe barrel 14, plunger rod 16, and oxygen absorber 18 therein. In one embodiment, packaging member 12 defines a first compartment 100, a second compartment 102, and a third compartment 104. The first compartment 100 is sized and adapted to receive syringe barrel 14 therein, the second compartment 102 is sized and adapted to receive plunger rod 16 therein, and the third compartment 104 is sized and adapted to receive oxygen absorber 18 therein. The first compartment 100, the second compartment 102, and the third compartment 104 are in gaseous communication theretogether. In this manner, with the packaging member 12 enclosing the syringe barrel 14, the plunger rod 16, and the oxygen absorber 18, the oxygen absorber 18 is adapted to draw oxygen from the syringe barrel 14 and to absorb oxygen contained within the first compartment 100, the second compartment 102, and the third compartment 104 of the packaging member 12.

Figures 8, 9:
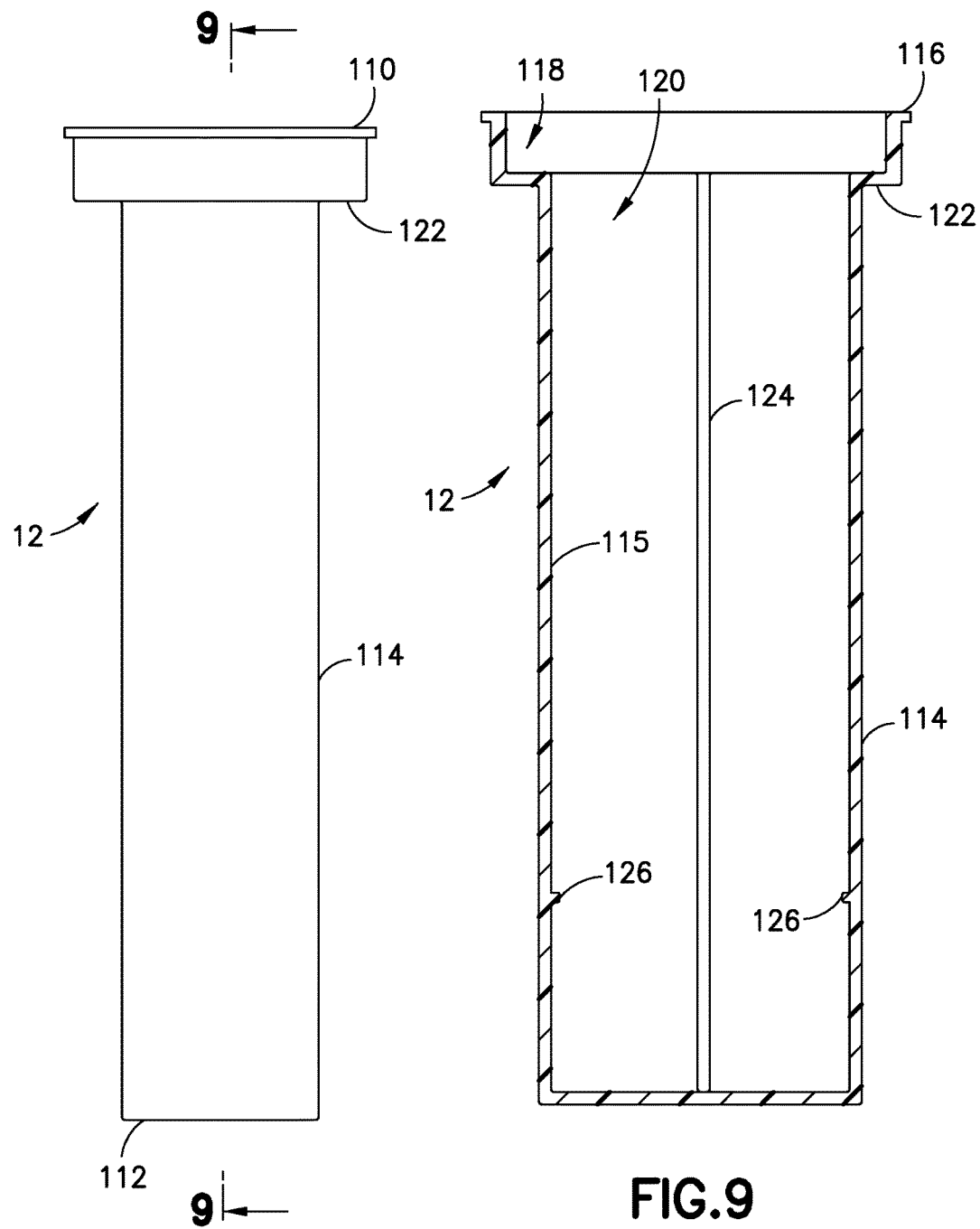
FIG. 8 is another side elevation view of a packaging member in accordance with an embodiment of the present invention.
FIG. 9 is a cross-sectional view of a packaging member taken along line 9-9 of FIG. 8 in accordance with an embodiment of the present invention.

Referring to FIGS. 1-9, packaging member 12 includes a first or top end 110, a second or bottom end 112, and a sidewall 114 extending between top end 110 and bottom end 112. Packaging member 12 includes a locking lip 116 at top end 110. Disposed below locking lip 116 is an upper tray portion 118 having a cross-section that has a greater area than a cross-section disposed below upper tray portion 118, i.e., a compartment portion 120, such that a shoulder 122 is defined therebetween. Upper tray portion 118 receives and supports flange 40 of syringe barrel 14 and flange 74 of plunger rod 16 as will be described in more detail below. Referring to FIG. 5, in one embodiment, an interior surface 115 of sidewall 114 of packaging member 12 defines opposing slots 124 extending along a longitudinal axis of packaging member 12. Referring to FIGS. 3A, 5, and 9, interior surface 115 of sidewall 114 of packaging member 12 includes opposing protrusions or locking ribs 126.

In one embodiment, packaging member 12 is formed of a generally oxygen impermeable material or a high oxygen barrier material, i.e., a low oxygen permeability material. For example, packaging member 12 may be formed of a polyester material or its derivative, a polyamide material or its derivative, or a blend from an extremely high oxygen barrier such as ethylene vinyl alcohol or similar material. In one embodiment, packaging member 12 may be formed of a single barrier material or a combination of barrier materials or multiple layers such that one or more of the layers provide the necessary barrier while the others are non-barrier materials providing necessary mechanical or other material properties. In one embodiment, multiple layers of the packaging member 12 may be formed by co-injection or two-shot injection or blending of an active oxygen material with a base resin, or a similar process with or without regard to the position of the barrier material or the non-barrier materials in the overall packaging structure. In one embodiment, the thickness of the packaging member 12 may be as low as 0.2 mm and as high as 1.2 mm as long as it provides the necessary mechanical strength and the oxygen barrier requirement is fulfilled.

In one embodiment, the surface properties, e.g., the coefficient of friction, of the materials for the oxygen absorber 18 and the packaging member 12 are such as to allow desirable and smooth movements between the oxygen absorber 18 and the packaging member 12 without causing any damage to any of the components of the syringe packaging system 10.

Figure 10:
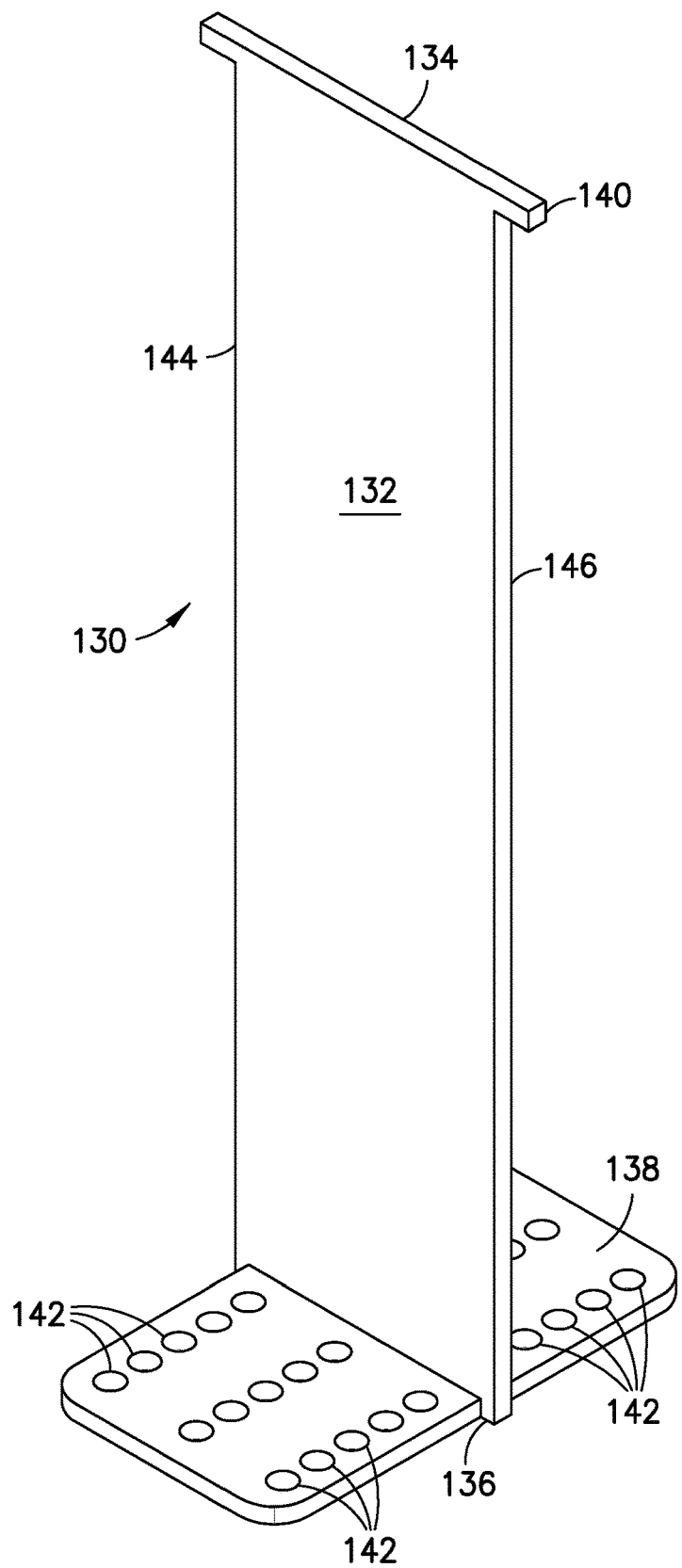
FIG. 10 is a perspective view of a partition member in accordance with an embodiment of the present invention.
Figures 11, 12:
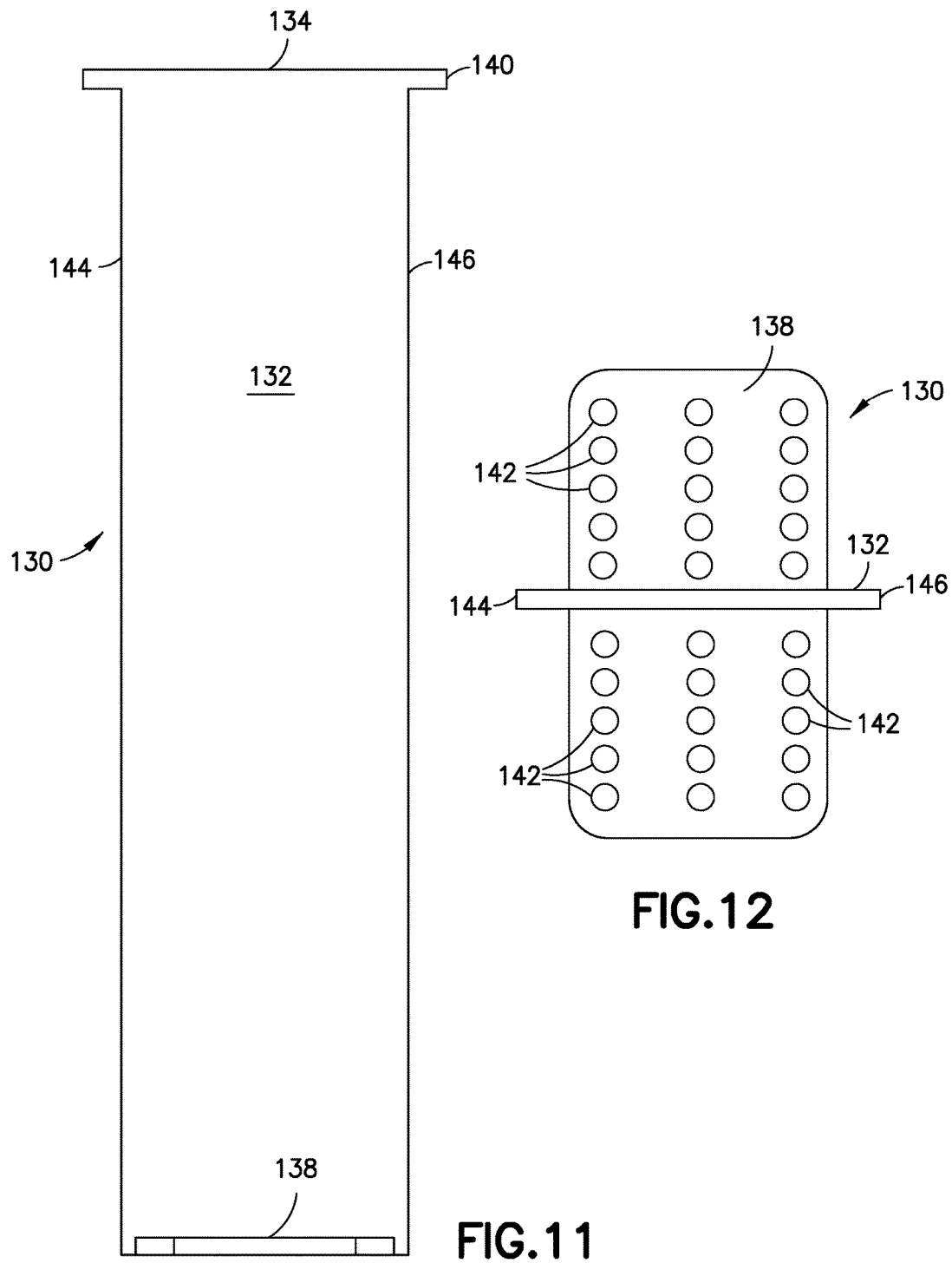
FIG. 11 is a side elevation view of a partition member in accordance with an embodiment of the present invention.
FIG. 12 is a top view of a partition member in accordance with an embodiment of the present invention.
Figure 14:
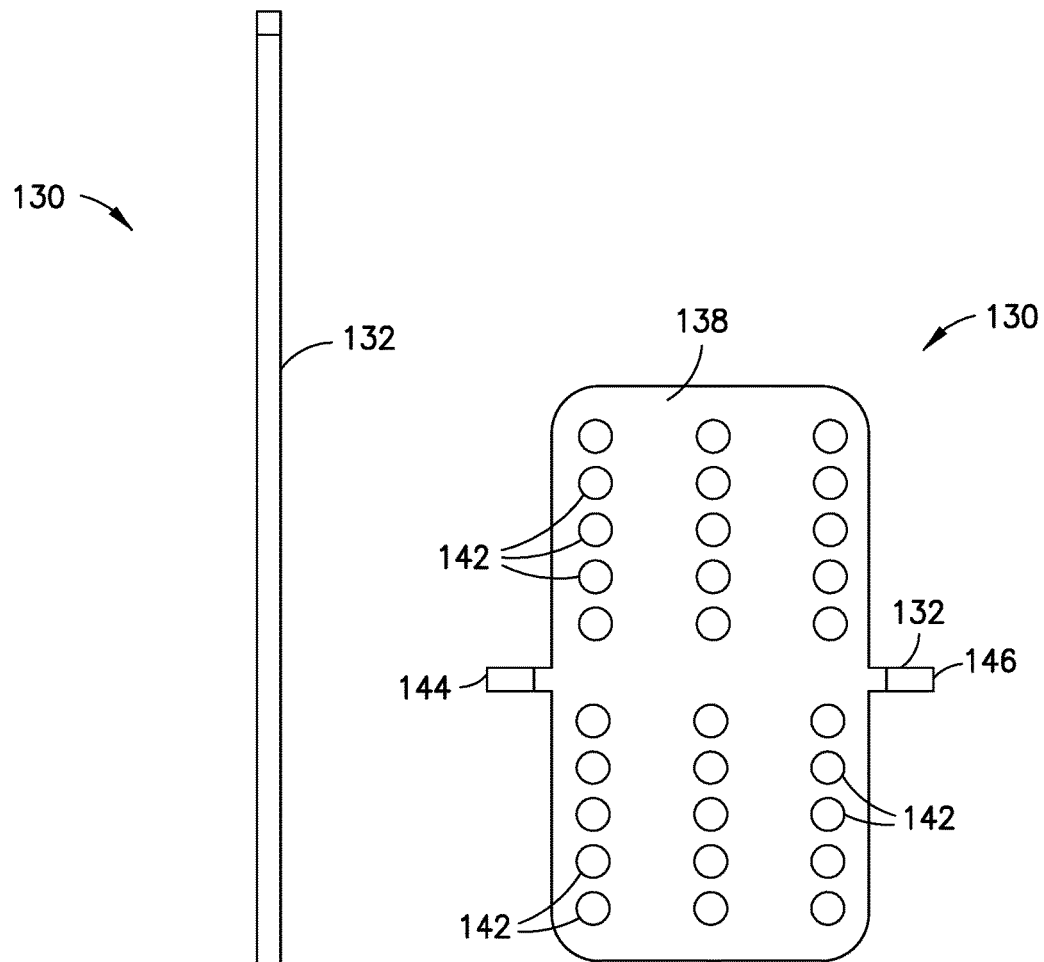
FIG. 14 is a bottom view of a partition member in accordance with an embodiment of the present invention.
Figure 13:
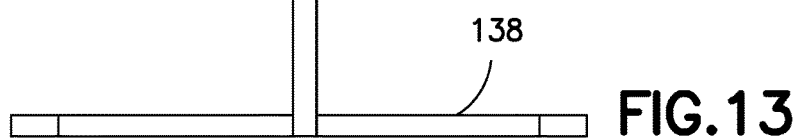
FIG. 13 is another side elevation view of a partition member in accordance with an embodiment of the present invention.

Referring to FIGS. 1-3B and 10-14, syringe packaging system 10 includes a partition member 130 that is receivable within the packaging member 12. The partition member 130 includes a vertical wall 132 having a first end 134 and a second end 136. The partition member 130 also includes a horizontal wall 138 located at second end 136 of vertical wall 132. In one embodiment, the vertical wall 132 and the horizontal wall 138 together generally form a T-shape. The first end 134 of the vertical wall 132 of partition member 130 includes a flange 140. The horizontal wall 138 of partition member 130 defines a plurality of gas holes 142. Referring to FIGS. 10-12, the width of vertical wall 132 is greater than the width of horizontal wall 138. In this manner, a first sidewall 144 and a second sidewall 146 of vertical wall 132 extend outward from horizontal wall 138 as shown in FIGS. 10-12.

All of the components of syringe packaging system 10 may be constructed of any known material, and are desirably constructed of medical-grade polymers.

Referring to FIGS. 1-14, packaging of syringe barrel 14, plunger rod 16, and oxygen absorber 18 within packaging member 12 will now be described. Initially, syringe barrel 14, plunger rod 16, and packaging member 12 are sterilized according to techniques known to those of ordinary skill in the art. In some embodiments, syringe barrel 14 may be pre-filled as described above.

Figure 3A:
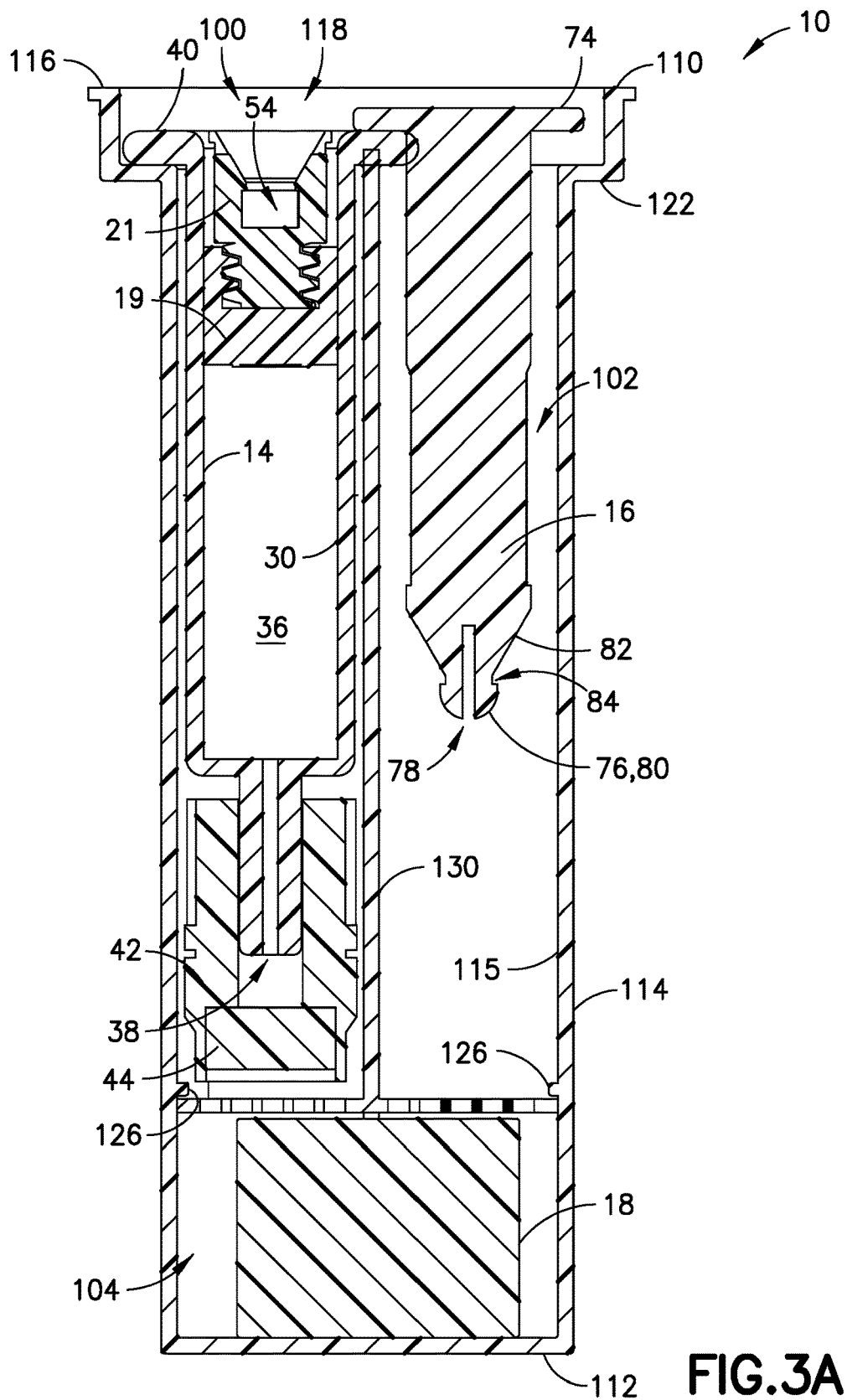
FIG. 3A is a cross-sectional view of the syringe packaging system of FIG. 2A in accordance with an embodiment of the present invention.
Figure 3B:
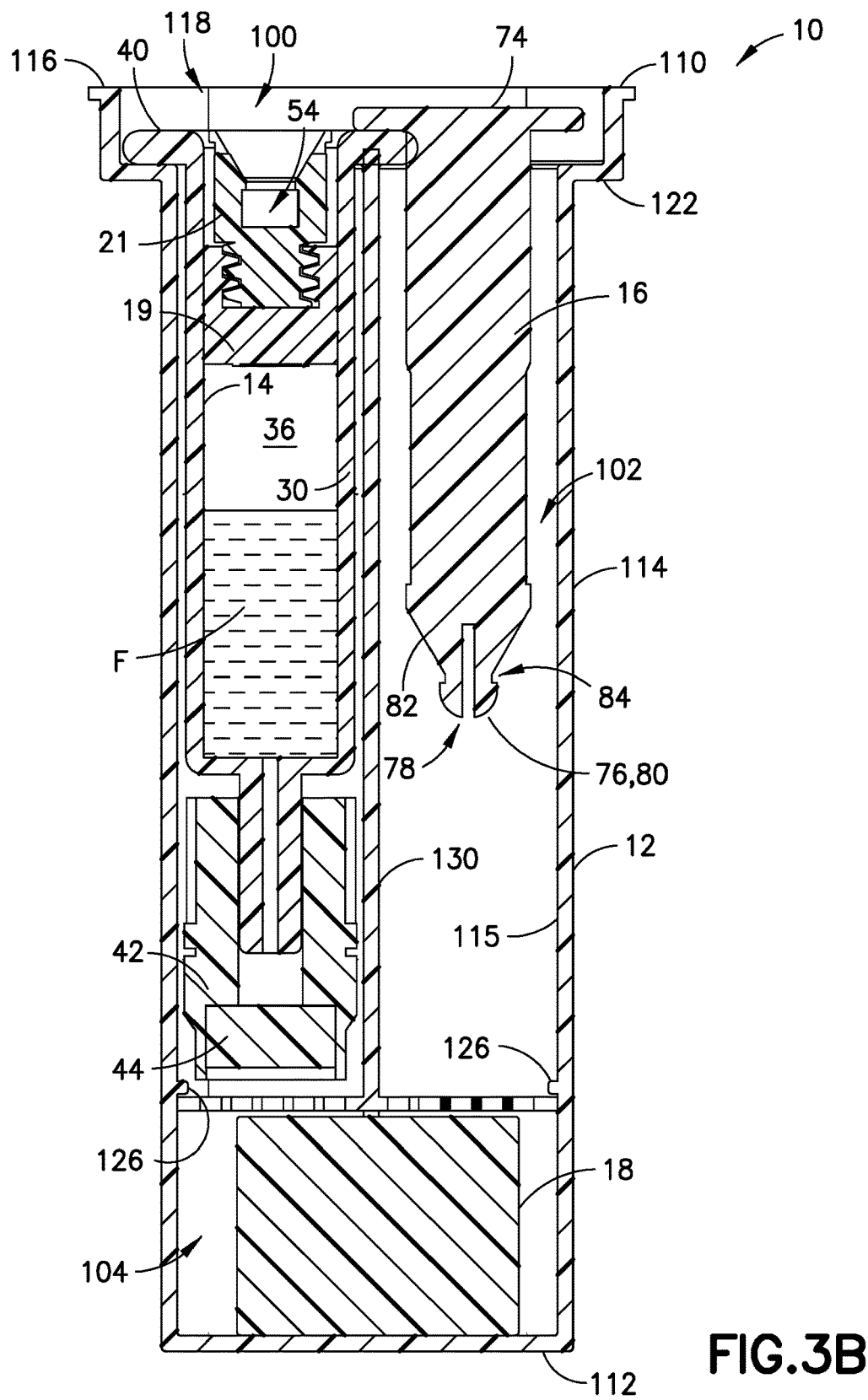
FIG. 3B is a cross-sectional view of the syringe packaging system of FIG. 2A with a fluid disposed within a chamber of a syringe barrel in accordance with an embodiment of the present invention.

Next, oxygen absorber 18 is inserted into compartment portion 120 of packaging member 12 such that oxygen absorber 18 is positioned horizontally within packaging member 12 adjacent bottom end 112 of packaging member 12 as shown in FIGS. 3A and 3B.

Next, partition member 130 is received within packaging member 12 as shown in FIGS. 2A-3B. To secure partition member 130 within packaging member 12, first sidewall 144 and second sidewall 146 of vertical wall 132 of partition member 130 are respectively positioned within opposing slots 124 of packaging member 12 and partition member 130 is inserted or moved axially into packaging member 12 in a direction generally along arrow A (FIG. 1). As additional force is exerted on partition member 130 to axially move partition member 130 in the direction generally along arrow A within packaging member 12, horizontal wall 138 of partition member 130 deforms locking ribs 126 of packaging member 12 outward until horizontal wall 138 of partition member 130 advances beyond, i.e., slides over and past, locking ribs 126 of packaging member 12 and locks partition member 130 to packaging member 12 as shown in FIGS. 3A and 3B. Once horizontal wall 138 of partition member 130 slides over and past locking ribs 126 of packaging member 12, locking ribs 126 return to their undeformed or original position as shown in FIGS. 3A and 3B. In this position, referring to FIGS. 3A and 3B, locking ribs 126 abut, contact, or engage horizontal wall 138 of partition member 130 and lock or secure partition member 130 to packaging member 12. This configuration ensures that partition member 130 is secured to packaging member 12, such that significant relative movement between partition member 130 and packaging member 12 is prevented. In this manner, partition member 130 and packaging member 12 define the first compartment 100, the second compartment 102, and the third compartment 104. The first compartment 100 is sized and adapted to receive syringe barrel 14 therein, the second compartment 102 is sized and adapted to receive plunger rod 16 therein, and the third compartment 104 is sized and adapted to receive oxygen absorber 18 therein. The first compartment 100, the second compartment 102, and the third compartment 104 are in gaseous communication theretogether. In one embodiment, gas holes 142 of horizontal wall 138 of partition member 130 provide gaseous communication between the third compartment 104 and the first compartment 100 and the second compartment 102. In this manner, with the packaging member 12 enclosing the syringe barrel 14, the plunger rod 16, and the oxygen absorber 18, the oxygen absorber 18 is adapted to draw oxygen from the syringe barrel 14 and to absorb oxygen contained within the first compartment 100, the second compartment 102, and the third compartment 104 of the packaging member 12.

Additionally, with partition member 130 secured to packaging member 12 as described above, such that, significant relative movement between partition member 130 and packaging member 12 is prevented, partition member 130 and packaging member 12 provide a third compartment 104 that secures oxygen absorber 18 within packaging member 12 such that oxygen absorber 18 is prevented from being removed from packaging member 12.

Next, referring to FIGS. 1-3B, syringe barrel 14 is inserted into first compartment 100 of packaging member 12 such that flange 40 of syringe barrel 14 abuts upper tray portion 118 as shown in FIGS. 3A and 3B. With syringe barrel 14 properly inserted into first compartment 100 of packaging member 12, plunger rod 16 is then inserted into second compartment 102 of packaging member 12 as shown in FIGS. 3A and 3B. In one embodiment, upper tray portion 118 of packaging member 12 may include a plunger rod support member such that with plunger rod 16 inserted into second compartment 102 of packaging member 12, flange 74 of plunger rod 16 abuts flange 40 of syringe barrel 14 on one side and abuts the plunger rod support member on another side.

As discussed above, after syringe packaging system 10 is properly sterilized, at least a portion of syringe barrel 14 may be properly inserted into first compartment 100 of packaging member 12; at least a portion of plunger rod 16 may be properly inserted into second compartment 102 of packaging member 12; and at least a portion of oxygen absorber 18 may be properly inserted into third compartment 104 of packaging member 12. Next, sealing member 15 (FIG. 2B) is used to cooperate with first end 110 of packaging member 12 to seal syringe barrel 14, plunger rod 16, and oxygen absorber 18 within packaging member 12, i.e., sealing member 15 and packaging member 12 together provide a substantially impermeable enclosure which provides a leak prevention and protection enclosure, protects the contents of syringe barrel 14, plunger rod 16, and oxygen absorber 18 contained within packaging member 12, and/or maintains a sealed, sterilized environment within packaging member 12. Additionally, sealing member 15 and packaging member 12 together provide an additional mechanism to reduce oxygen levels within packaging member 12 by sealing syringe barrel 14, plunger rod 16, and oxygen absorber 18 within packaging member 12 to prevent oxygen external to syringe packaging system 10 from entering the sealed packaging member 12. Sealing member 15 and packaging member 12 together provide a sufficient seal at a range of temperatures, pressures, and humidity levels.

As previously discussed, by disposing oxygen absorber 18 within the sealed packaging member 12, oxygen absorber 18 can reduce the oxygen levels within packaging member 12 and remove oxygen contained in fluid F (FIG. 3B) disposed within chamber 36 of syringe barrel 14. Any oxygen contained within packaging member 12 will be absorbed by oxygen absorber 18. Additionally, oxygen contained within chamber 36 of syringe barrel 14, and/or oxygen contained in fluid F disposed within chamber 36 of syringe barrel 14, will flow from chamber 36 of syringe barrel 14 to oxygen absorber 18 via the portion of syringe barrel 14 that includes an oxygen permeable member as described above. Reduction of oxygen levels within packaging member 12 is important because atmospheric gases such as oxygen contained in packaging member 12 and contained in the fluid F disposed within chamber 36 of syringe barrel 14 can cause fluid F, such as a medication or drug in a pre-filled syringe, to degrade.

The syringe packaging system of the present disclosure also allows for reduced storage space of a syringe assembly. By having syringe assembly 13 including plunger rod 16 separate and detached from syringe barrel 14, plunger rod 16 and syringe barrel 14 can be separately placed in packaging member 12 in a manner that allows for reduced storage space of syringe assembly 13. For example, a conventional pre-filled syringe is typically packaged with a plunger rod retracted out of a back or proximal end of a syringe barrel, with the fluid pre-filled within the syringe barrel. Accordingly, packaging of such pre-filled syringes is bulky and awkward for shipping and storage. For example, the overall length to be packaged of a conventional pre-filled syringe is equal to the length of the syringe barrel and the length that the plunger rod extends outwardly from the syringe barrel. By having syringe assembly 13 including plunger rod 16 separate and detached from syringe barrel 14, plunger rod 16 and syringe barrel 14 can be separately placed in packaging member 12 as shown in FIGS. 3A and 3B in a manner that allows for reduced storage space of syringe assembly 13. In this manner, the overall length to be packaged of a syringe assembly 13 of the present disclosure is equal to the length of the syringe barrel 14. Accordingly, a syringe assembly 13 in accordance with the present invention allows plunger rod 16 and syringe barrel 14 to be packaged in a manner that allows for reduced storage space.

Additionally, in accordance with a syringe assembly of the present invention, upon removal of plunger rod 16 and syringe barrel 14 from packaging member 12, plunger rod 16 can quickly and easily be secured to syringe barrel 14 for collecting a fluid and/or delivering a fluid.

Referring to FIGS. 3A and 3B, oxygen absorber 18 is positioned in the packaging member 12 underneath plunger rod 16, i.e., oxygen absorber 18 is positioned adjacent the closed bottom end 112 of packaging member 12 and plunger rod 16 is positioned above the oxygen absorber 18 as shown in FIGS. 3A and 3B. For example, the third compartment 104 which is sized and adapted to receive the oxygen absorber 18 therein is located underneath the second compartment 102 which is sized and adapted to receive the plunger rod 16 therein as shown in FIGS. 3A and 3B. In this manner, upon removal of plunger rod 16 and syringe barrel 14 from packaging member 12, oxygen absorber 18 is prevented from also being removed from packaging member 12. Referring to FIGS. 24-70, in other exemplary embodiments of the present disclosure, the oxygen absorber 18 is positioned in the packaging member underneath plunger rod 16, i.e., oxygen absorber 18 is positioned adjacent the closed bottom end of the packaging member and plunger rod 16 is positioned above the oxygen absorber 18.

Referring to FIGS. 1-3B, 15, and 17-23, removal of syringe barrel 14 and plunger rod 16 from packaging member 12 so that syringe barrel 14 and plunger rod 16 can be secured together to form a syringe assembly to expel a fluid, such as a medication, contained within chamber 36 of syringe barrel 14 will now be described. Initially, the user removes syringe barrel 14 and plunger rod 16 from packaging member 12. To remove syringe barrel 14 and plunger rod 16 from packaging member 12, in one embodiment, a user can first check to make sure a tear strip or other tamper evidence member has not been broken. Next, the user can remove the tamper evidence member and then break the above described seal between sealing member 15 (FIG. 2B) and packaging member 12.

With the seal between sealing member 15 and packaging member 12 broken, a user can grasp flange 74 of plunger rod 16 and pull flange 74 longitudinally to remove plunger rod 16 from second compartment 102 of packaging member 12. Next, a user can grasp flange 40 of syringe barrel 14 located in upper tray portion 118 of packaging member 12 and pull flange 40 longitudinally to remove syringe barrel 14 from first compartment 100 of packaging member 12. With plunger rod 16 and syringe barrel 14 removed from packaging member 12, plunger rod 16 and syringe barrel 14 can be secured together to form syringe assembly 13 adapted for dispensing and delivery of a fluid and/or collection of a fluid.

As described above, with partition member 130 secured to packaging member 12, such that significant relative movement between partition member 130 and packaging member 12 is prevented, partition member 130 and packaging member 12 provide a third compartment 104 that secures oxygen absorber 18 within packaging member 12 such that oxygen absorber 18 is prevented from being removed from packaging member 12 when syringe barrel 14 and plunger rod 16 are removed from packaging member 12.

Referring to FIGS. 17-23, an embodiment of a securement feature operable to secure plunger rod 16 to syringe barrel 14 via stopper adapter 21 will now be described. With plunger rod head 78 of plunger rod 16 positioned adjacent plunger receiving aperture 54 of stopper adapter 21, plunger rod 16 is inserted or moved axially into plunger receiving aperture 54 in a direction generally along arrow B (FIG. 17), such that elastic fingers 80 of plunger rod head 78 are disposed within plunger receiving aperture 54 of stopper adapter 21. As additional force is exerted on plunger rod 16 to axially move plunger rod head 78 in the direction generally along arrow B within plunger receiving aperture 54, elastic fingers 80 cooperate with tapered portion 60 of protruding annular ring 58 and protruding annular ring 58 pushes or compresses elastic fingers 80 of plunger rod head 78 inward in a direction generally along arrow C (FIG. 18A) until elastic fingers 80 of plunger rod head 78 slide over and past tapered portion 60 of protruding annular ring 58 and lock plunger rod 16 to stopper adapter 21 as shown in FIGS. 18A and 18B. Once elastic fingers 80 of plunger rod head 78 slide over and past tapered portion 60 of protruding annular ring 58, elastic fingers 80 return to their original position as shown in FIGS. 17 and 18A. In this position, referring to FIG. 18A, locking end 62 of protruding annular ring 58 abuts, contacts, or engages locking end 88 of elastic fingers 80 with protruding annular ring 58 disposed adjacent annular groove 84 of plunger rod head 78 and locks or secures plunger rod 16 to stopper adapter 21. This configuration ensures that with elastic fingers 80 mechanically locked over protruding annular ring 58, plunger rod 16 is secured to stopper adapter 21, such that significant relative movement between plunger rod 16 and stopper adapter 21 is prevented. In this manner, plunger rod 16 is adapted for advancing stopper 19 within syringe barrel 14.

In another embodiment, the engagement portion 56 of stopper adapter 21 may include a deformable restraining member, e.g., elastic fingers, and the engagement portion 76 of plunger rod 16 may include a plunger rod head 78 formed of a rigid, unyielding material for securing plunger rod 16 to stopper adapter 21. In another alternative embodiment, plunger rod 16 can be secured to syringe barrel 14 via stopper adapter 21 by threadingly engaging a threaded portion of plunger rod 16 to a threaded portion of stopper adapter 21. In other embodiments, plunger rod 16 can be secured to stopper adapter 21 using a ball detent, locking tabs, spring loaded locking mechanism, latch, adhesive, or other similar mechanism. In all embodiments, plunger rod 16 is locked, secured, or engaged to stopper adapter 21, i.e., significant relative movement between plunger rod 16 and stopper adapter 21 is prevented and movement of plunger rod 16 can be transferred to stopper 19 to slide stopper 19 between positions within syringe barrel 14. In other alternate embodiments, plunger rod 16 and stopper adapter 21 may be integrally formed and both form a plunger assembly positioned within second compartment 102 of packaging member 12 and the separate syringe barrel 14 positioned within first compartment 100 of packaging member 12.

In other embodiments, plunger rod 16 and stopper adapter 21 may be co-formed such as by co-extrusion. In alternate embodiments, plunger rod 16 and stopper adapter 21 may be integrally formed as a plunger assembly that is securable to syringe barrel 14.

Figure 21:
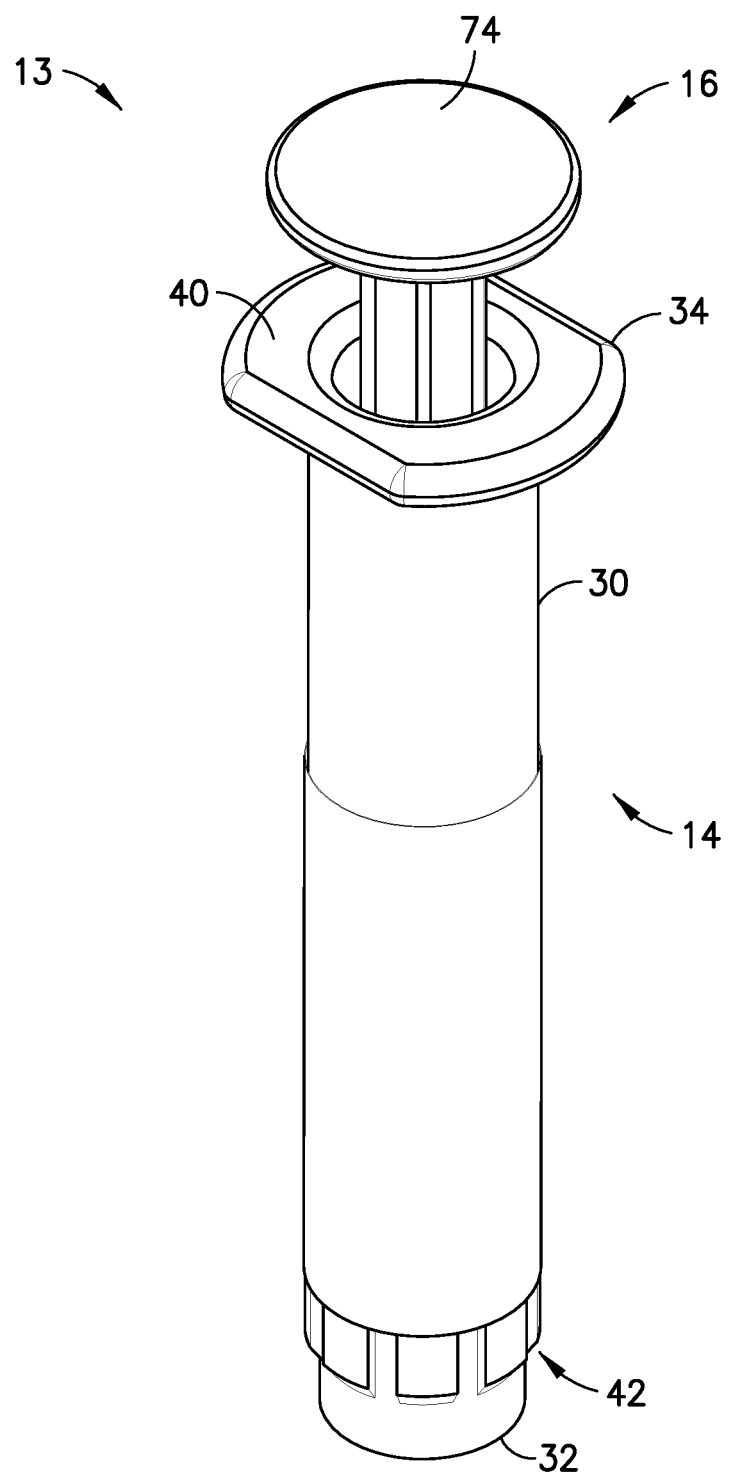
FIG. 21 is an assembled, perspective view of the syringe barrel, the stopper, and the plunger rod of FIG. 17 in accordance with an embodiment of the present invention.
Figure 24:
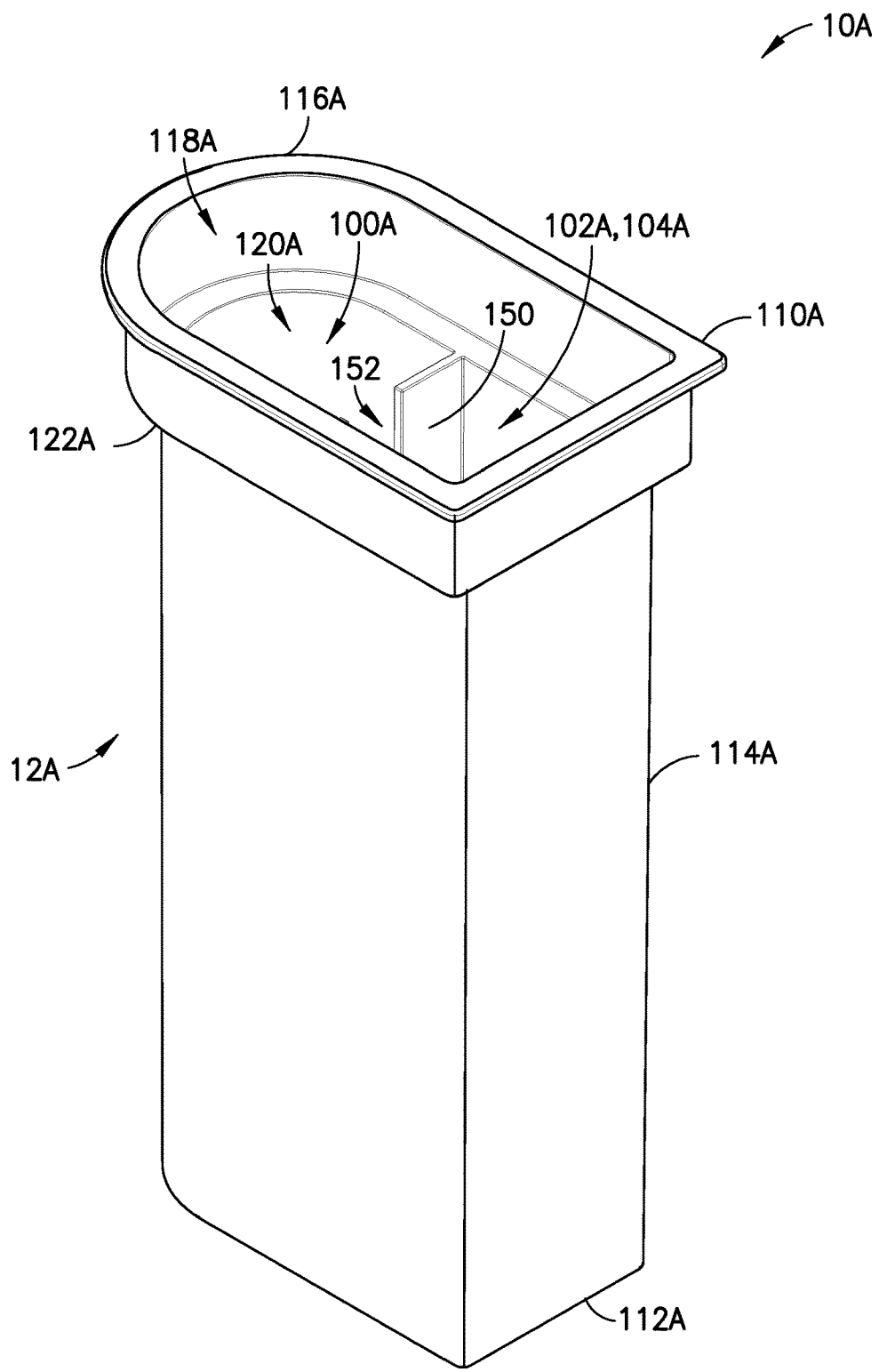
FIG. 24 is a perspective view of a packaging member in accordance with an embodiment of the present invention.
Figures 25, 26:
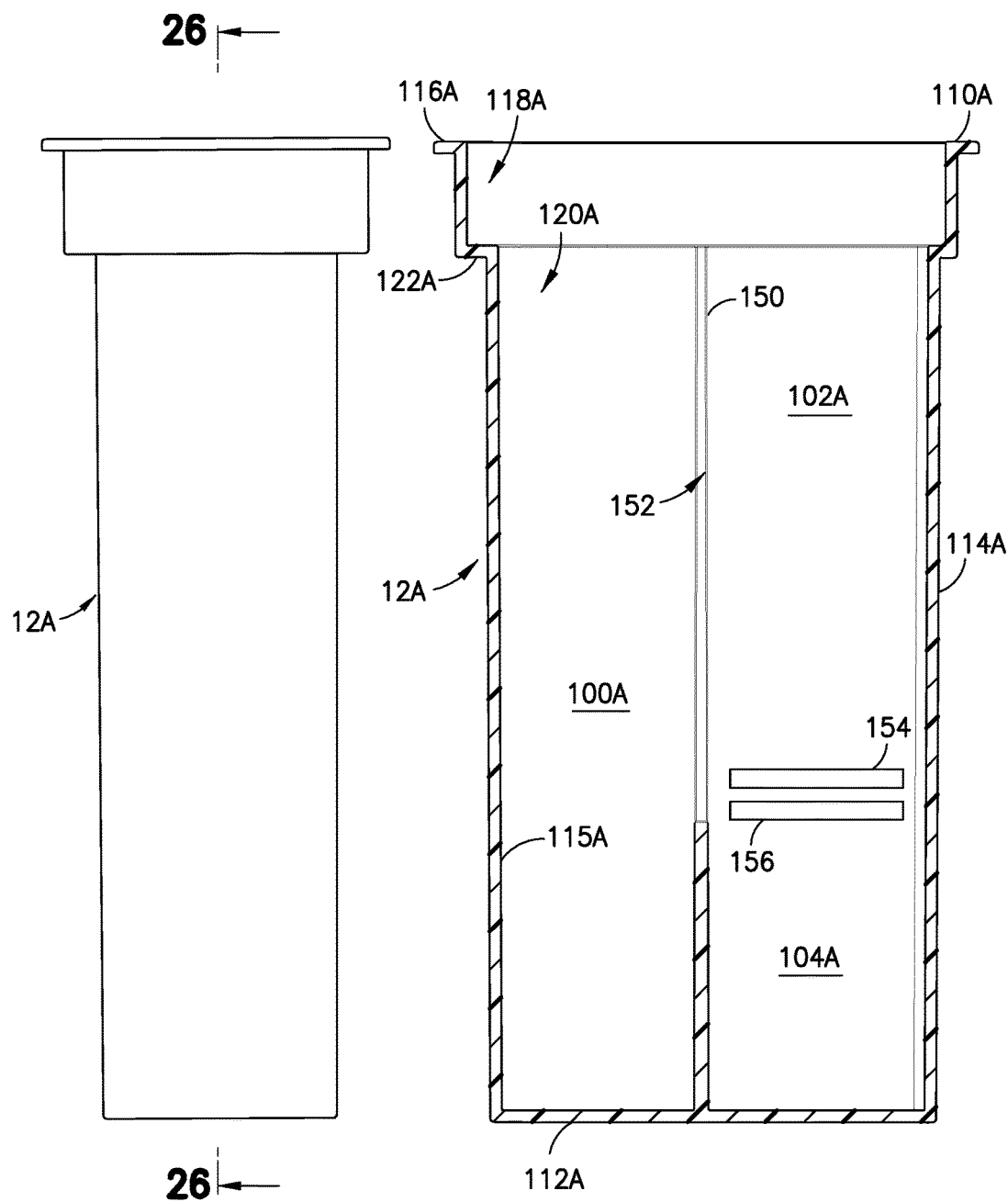
FIG. 25 is a side elevation view of a packaging member in accordance with an embodiment of the present invention.
FIG. 26 is a cross-sectional view of a packaging member taken along line 26-26 of FIG. 25 in accordance with an embodiment of the present invention.
Figure 29:
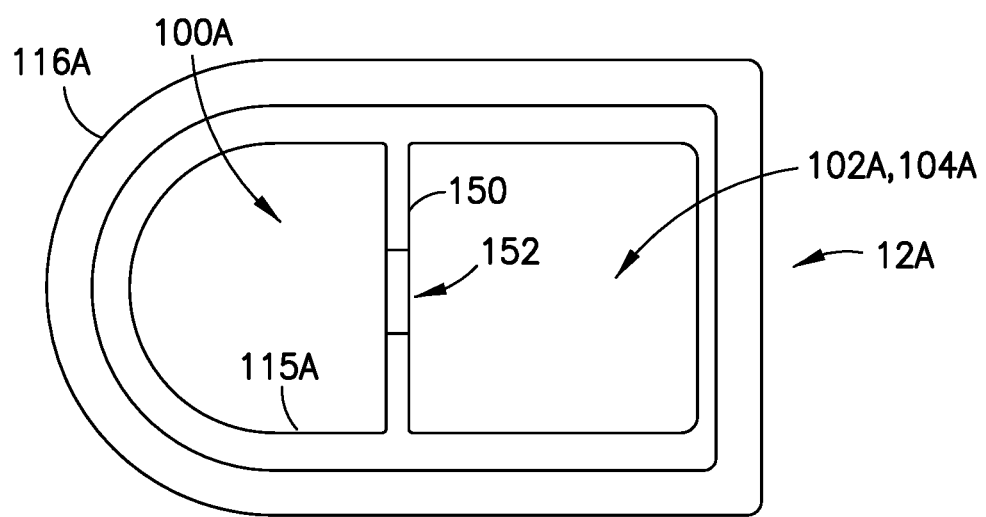
FIG. 29 is a top view of a packaging member in accordance with an embodiment of the present invention.

Next, referring to FIGS. 21-23, with plunger rod 16 and syringe barrel 14 secured together to form syringe assembly 13, a user can remove sealing cap member 42 from distal end 32 of syringe barrel 14. A user can then attach distal end 32 of syringe barrel 14 to a separate needle assembly or IV connection assembly and lockingly engage the needle assembly or IV connection assembly to distal end 32 of syringe barrel 14 in a known manner. Prior to dispensing any medication, any gas or air trapped within chamber 36 of syringe barrel 14 can be expelled in a known manner.

Referring to FIGS. 21-23, the use of syringe assembly 13 to expel a fluid, such as a medication, contained within chamber 36 of syringe barrel 14 will now be described. Movement of flange 74 of plunger rod 16 provides actuation means for moving or sliding stopper 19 between positions within syringe barrel 14. For example, flange 74 may have any shape that allows a user to grip and actuate flange 74 of plunger rod 16 in a back and forth direction.

When it is desired to expel or deliver the medication contained within syringe barrel 14, syringe assembly 13 is grasped with the user's thumb on flange 74 of plunger rod 16 and with the user's fingers grasping and extending around flange 40 of syringe barrel 14. In this manner, syringe assembly 13 is grasped by a user in a well-known and well recognized manner similar to the operation of a conventional hypodermic syringe. Next, the user effects a squeezing movement between the thumb on flange 74 of plunger rod 16 and four fingers grasping flange 40 of syringe barrel 14, thereby causing flange 74 of plunger rod 16 to move in a direction generally along arrow D (FIG. 23) toward proximal end 34 of syringe barrel 14. In this manner, movement of stopper 19 in the direction generally along arrow D forces the fluid F (FIG. 3B) contained within chamber 36 of syringe barrel 14 to be forced out outlet opening 38, i.e., movement of stopper 19 towards distal end 32 of syringe barrel 14 reduces the volume of chamber 36 and forces the fluid F from syringe barrel 14. The fluid F can be expelled from syringe barrel 14 through outlet opening 38 for contact with a patient and/or into a separate needle assembly or IV assembly and into the patient.

Referring now to FIGS. 21-23, the use of syringe assembly 13 to fill syringe barrel 14 with medication from a separate vial prior to use will now be described. With syringe assembly 13 in a position in which stopper 19 is located adjacent distal end 32 of syringe barrel 14 and with a needle assembly locked to distal end 32 of syringe barrel 14 and placed in a vial containing fluid, when it is desired to aspirate or pull the fluid, such as a medication, into chamber 36 of syringe barrel 14, a user moves flange 74 of plunger rod 16 in a direction generally along arrow E (FIG. 23) and away from proximal end 34 of syringe barrel 14 until the desired amount of the fluid is pulled into chamber 36 of syringe barrel 14.

In this manner, movement of stopper 19 in the direction generally along arrow E creates a vacuum inside chamber 36 of syringe barrel 14. As the user moves stopper 19, via plunger rod 16 in the direction generally along arrow E, the user actively increases the volume within chamber 36 of syringe barrel 14. Because the stopper is sized relative to syringe barrel 14 to provide sealing engagement with the interior wall of syringe barrel 14, as described above, and because the needle assembly locked to distal end 32 of syringe barrel 14 is placed in a vial containing fluid, no gas or air can enter into chamber 36 of syringe barrel 14 and, thus, the same number of gas or air molecules are located within chamber 36 as the user actively increases the volume within chamber 36. This decreases the pressure in chamber 36 of syringe barrel 14 relative to the air pressure outside of syringe barrel 14. Therefore, a vacuum, i.e., a space of lower air pressure, is created to pull the fluid, such as a medication, into chamber 36 of syringe barrel 14. Advantageously, syringe assembly 13 can be used to collect a fluid into chamber 36 of syringe barrel 14 or to expel a fluid out of chamber 36 of syringe barrel 14.

FIGS. 24-33 illustrate another exemplary embodiment of the present disclosure. Referring to FIGS. 24-33, a syringe packaging system 10A includes a packaging member 12A, a syringe assembly 13 including a syringe barrel 14 and a detachable plunger rod 16, an oxygen absorber 18, and a stopper 19. With the packaging member 12A enclosing the syringe barrel 14, the plunger rod 16, and the oxygen absorber 18, the oxygen absorber 18 is adapted to draw oxygen from the syringe barrel 14 and to absorb oxygen contained within the packaging member 12A. The syringe packaging system 10A of the present disclosure also allows for reduced storage space of a syringe assembly.

The exemplary embodiment illustrated in FIGS. 24-33 includes similar components to the embodiment illustrated in FIGS. 1-9. For the sake of brevity, these similar components and the similar steps of using syringe packaging system 10A will not all be discussed in conjunction with the embodiment illustrated in FIGS. 24-33. In one embodiment, syringe packaging system 10A is compatible with the syringe assembly 13 and the oxygen absorber 18 shown in FIGS. 15-23.

Referring to FIGS. 24-33, a syringe packaging system 10A includes a packaging member 12A formed of a generally oxygen impermeable material. In one embodiment, a sealing member 15 (FIG. 2B) may be removably attached to packaging member 12A. Packaging member 12A is sized and adapted to receive each of syringe barrel 14, plunger rod 16, and oxygen absorber 18 therein as will be described in more detail below.

Referring to FIGS. 24-33, packaging member 12A includes a first compartment 100A, a second compartment 102A, a third compartment 104A, a first or top end 110A, a second or bottom end 112A, and a sidewall 114A extending between top end 110A and bottom end 112A. Packaging member 12A includes a locking lip 116A at top end 110A. Disposed below locking lip 116A is an upper tray portion 118A having a cross-section that has a greater area than a cross-section disposed below upper tray portion 118A, i.e., a compartment portion 120A, such that a shoulder 122A is defined therebetween. The compartment portion 120A includes a separator wall 150 disposed therein such that separator wall 150 divides compartment portion 120A into first compartment 100A and second compartment 102A. The separator wall 150 defines a gas slot 152 which maintains first compartment 100A and second compartment 102A in gaseous communication theretogether. The second compartment 102A includes a first bump 154 and a second bump 156 spaced from first bump 154. In one embodiment, first bump 154 and second bump 156 are molded on an interior surface 115A of sidewall 114A of packaging member 12A.

Figure 30:
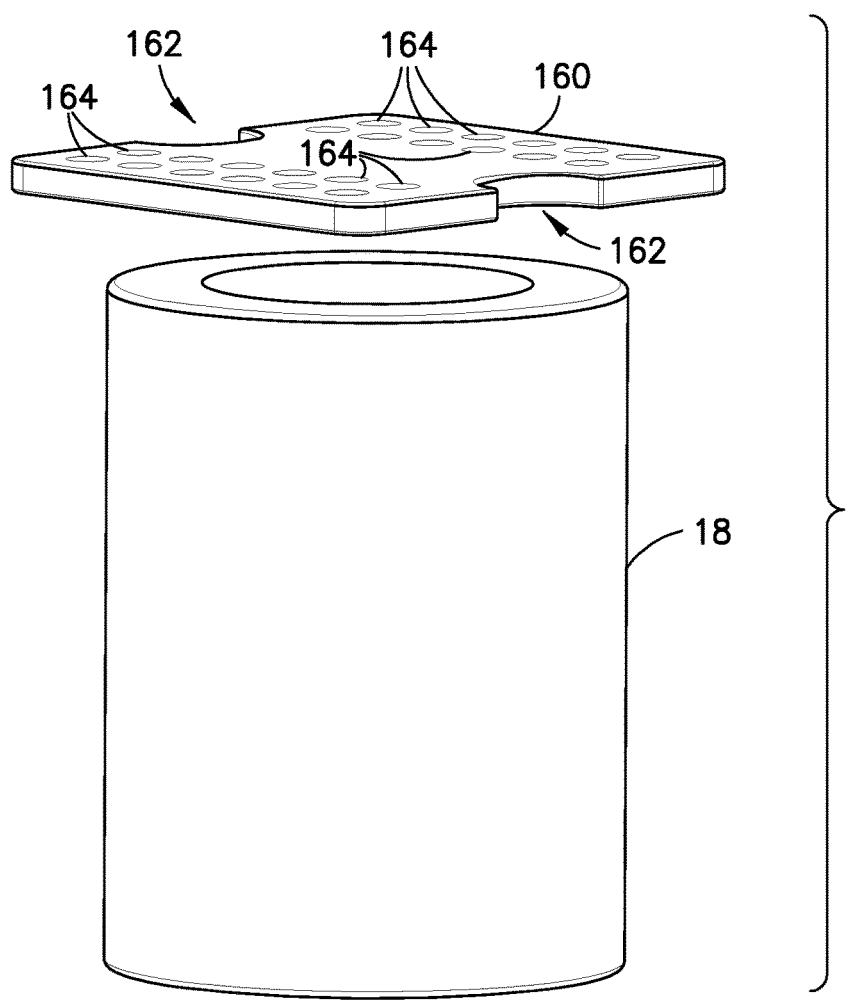
FIG. 30 is a perspective view of a partition member and an oxygen absorber in accordance with an embodiment of the present invention.

Referring to FIG. 30, syringe packaging system 10A includes a partition member 160 that is receivable within the packaging member 12A. The partition member 160 includes opposing notches 162 and defines a plurality of gas holes 164.

All of the components of syringe packaging system 10A may be constructed of any known material, and are desirably constructed of medical-grade polymers.

Figure 31:
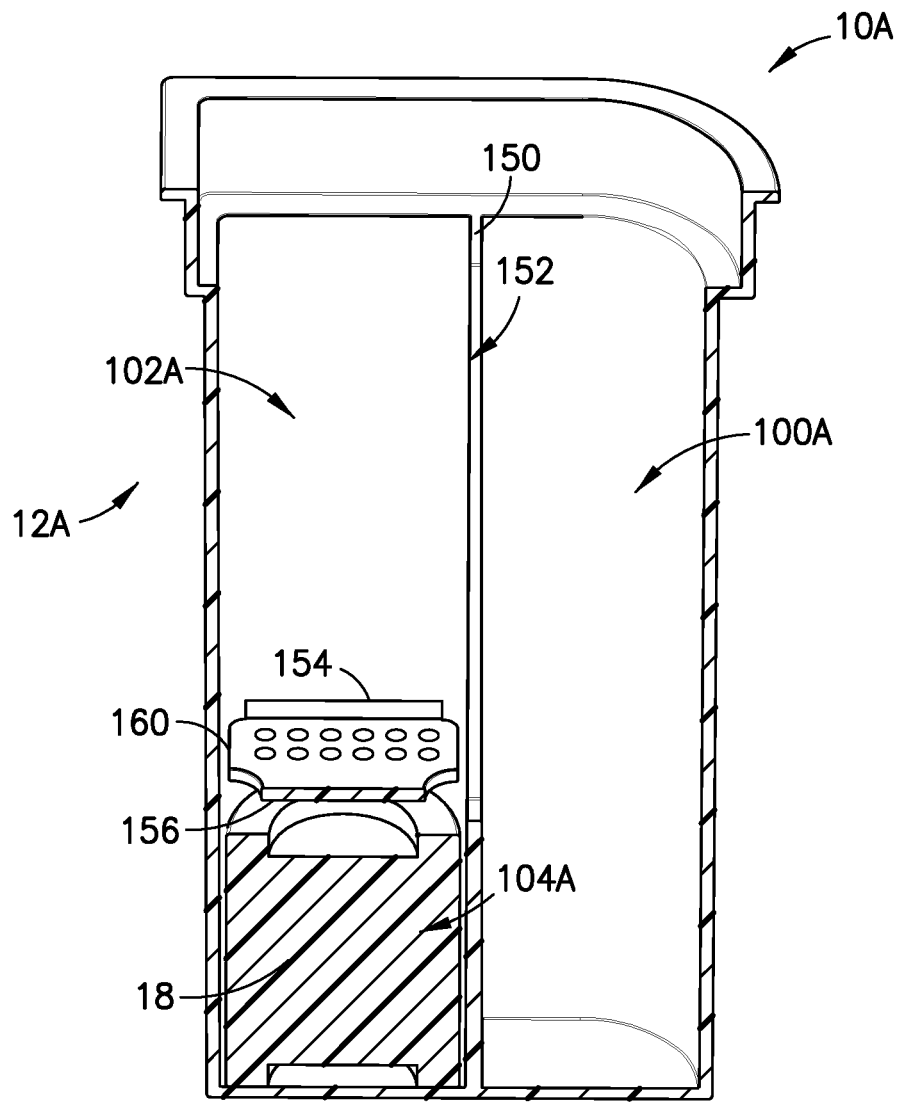
FIG. 31 is a schematic cross-sectional view of a syringe packaging system in accordance with an embodiment of the present invention.
Figure 32:
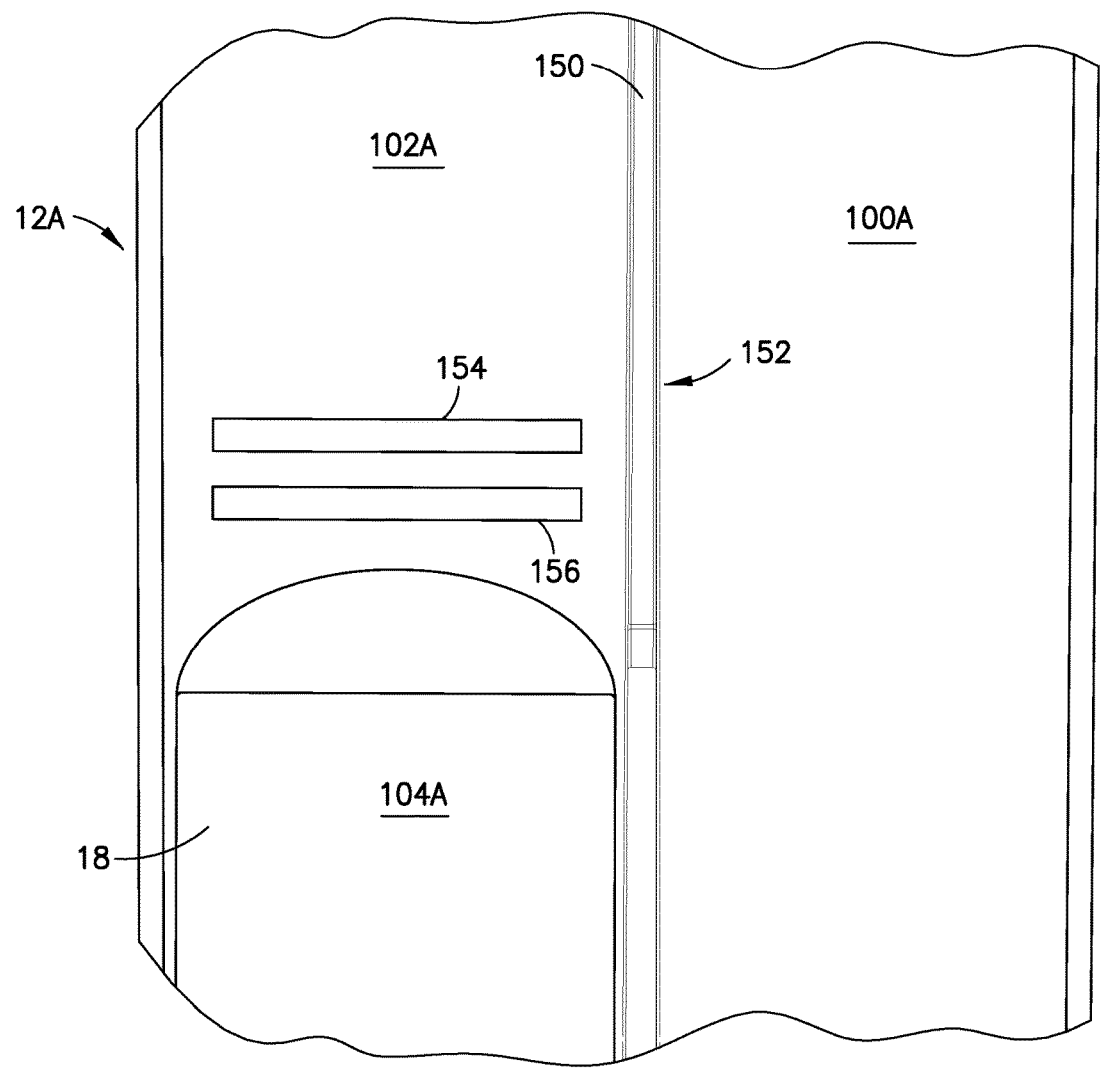
FIG. 32 is an enlarged partial view of the syringe packaging system of FIG. 31 in accordance with an embodiment of the present invention.

Referring to FIGS. 24-33, packaging of syringe barrel 14, plunger rod 16, and oxygen absorber 18 within packaging member 12A will now be described. Initially, syringe barrel 14, plunger rod 16, and packaging member 12A are sterilized according to techniques known to those of ordinary skill in the art as described above. In some embodiments, syringe barrel 14 may be pre-filled as described above. Next, oxygen absorber 18 is inserted into the third compartment 104A side of compartment portion 120A of packaging member 12A such that oxygen absorber 18 is positioned vertically within packaging member 12A adjacent bottom end 112A of packaging member 12A on the third compartment 104A side as shown in FIG. 31.

Figure 33:
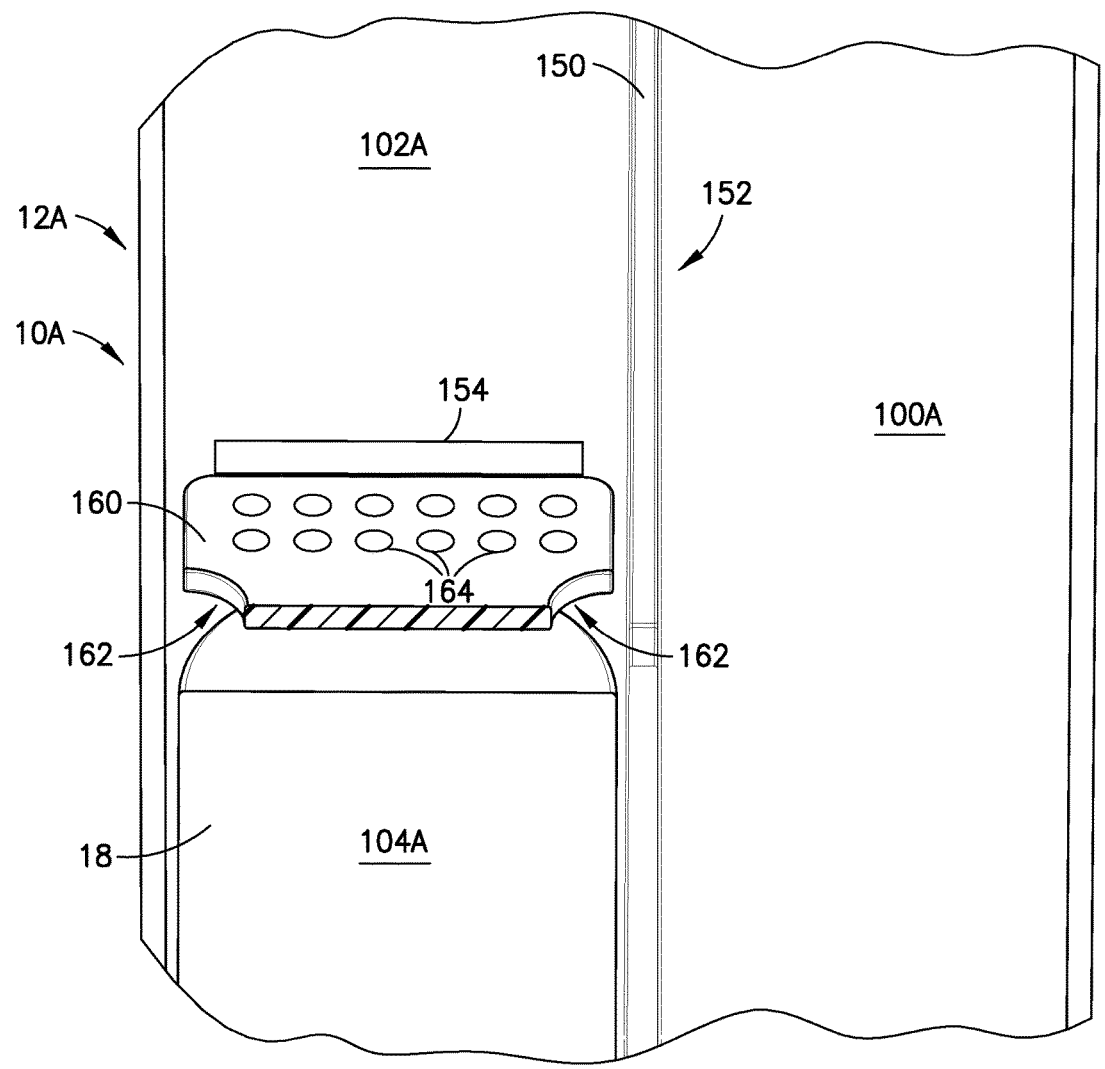
FIG. 33 is an enlarged partial cross-sectional view of the syringe packaging system of FIG. 31 with a partition member received between a first bump and a second bump in accordance with an embodiment of the present invention.
Figure 34:
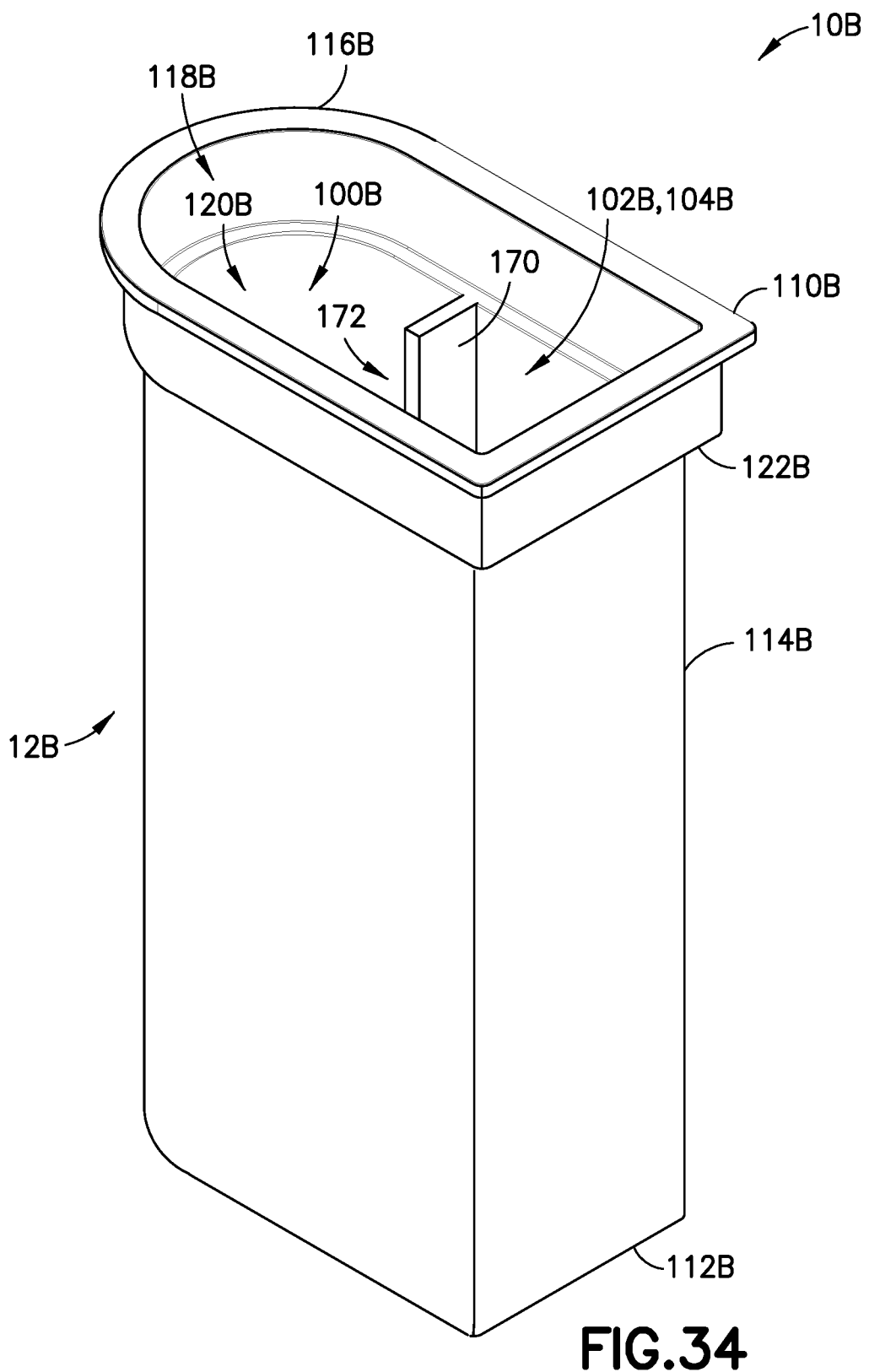
FIG. 34 is a perspective view of a packaging member in accordance with an embodiment of the present invention.
Figure 37:
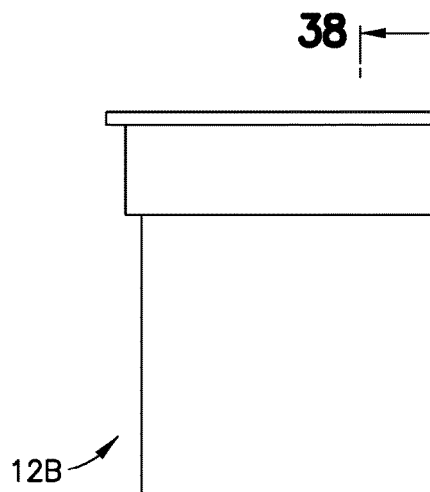
FIG. 37 is another side elevation view of a packaging member in accordance with an embodiment of the present invention.
Figure 38:
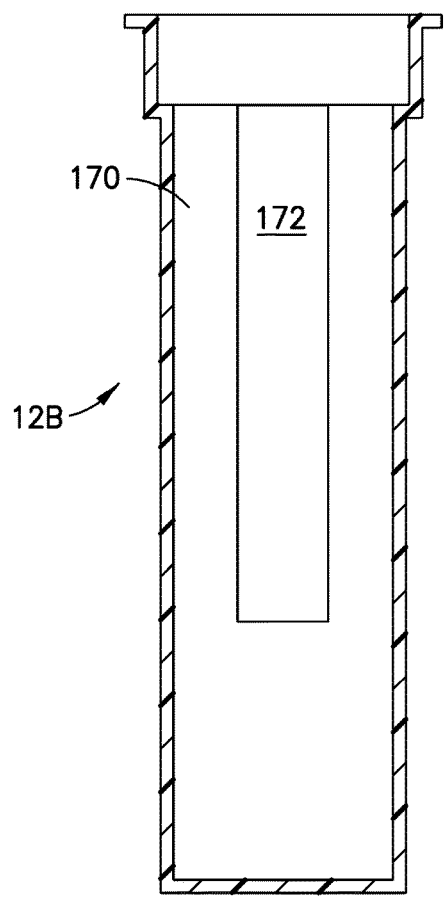
FIG. 38 is a cross-sectional view of a packaging member taken along line 38-38 of FIG. 37 in accordance with an embodiment of the present invention.
Figure 39:
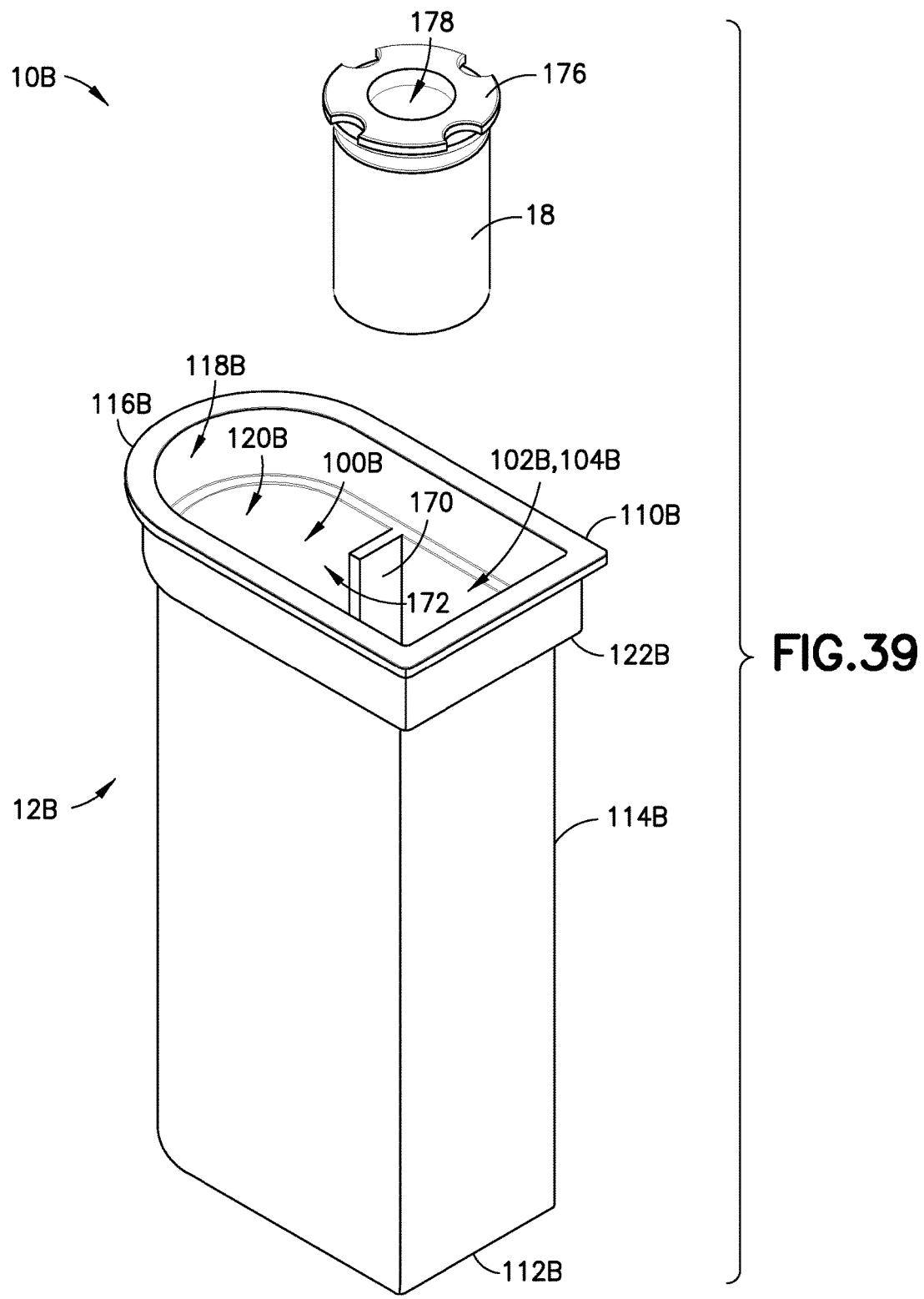
FIG. 39 is an exploded, perspective view of a syringe packaging system in accordance with an embodiment of the present invention.
Figure 40:
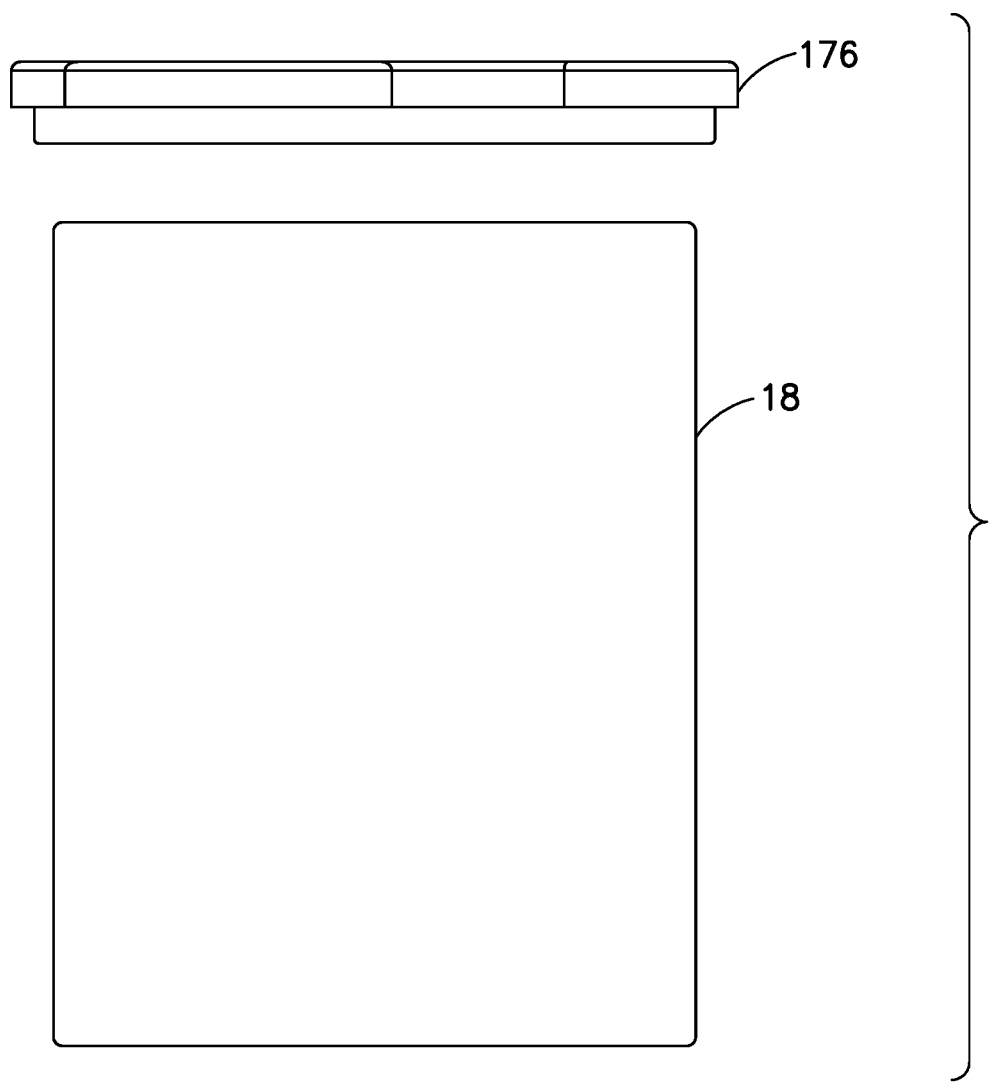
FIG. 40 is a side elevation view of a lid and an oxygen absorber in accordance with an embodiment of the present invention.
Figure 41:
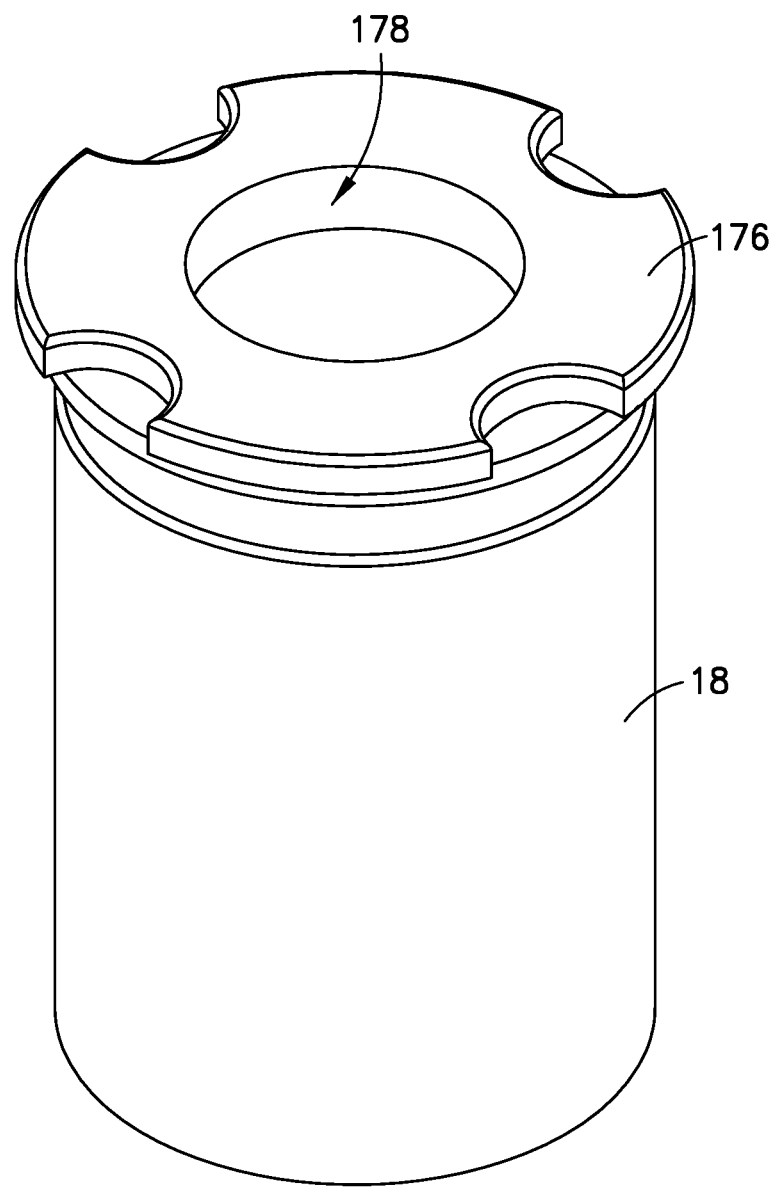
FIG. 41 is a perspective view of a lid and an oxygen absorber in accordance with an embodiment of the present invention.
Figure 42:
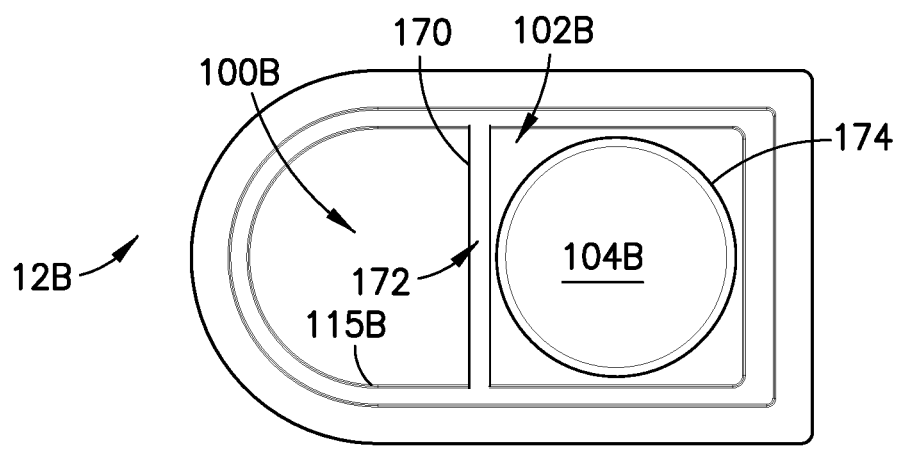
FIG. 42 is a top view of a packaging member in accordance with an embodiment of the present invention.
Figure 43:
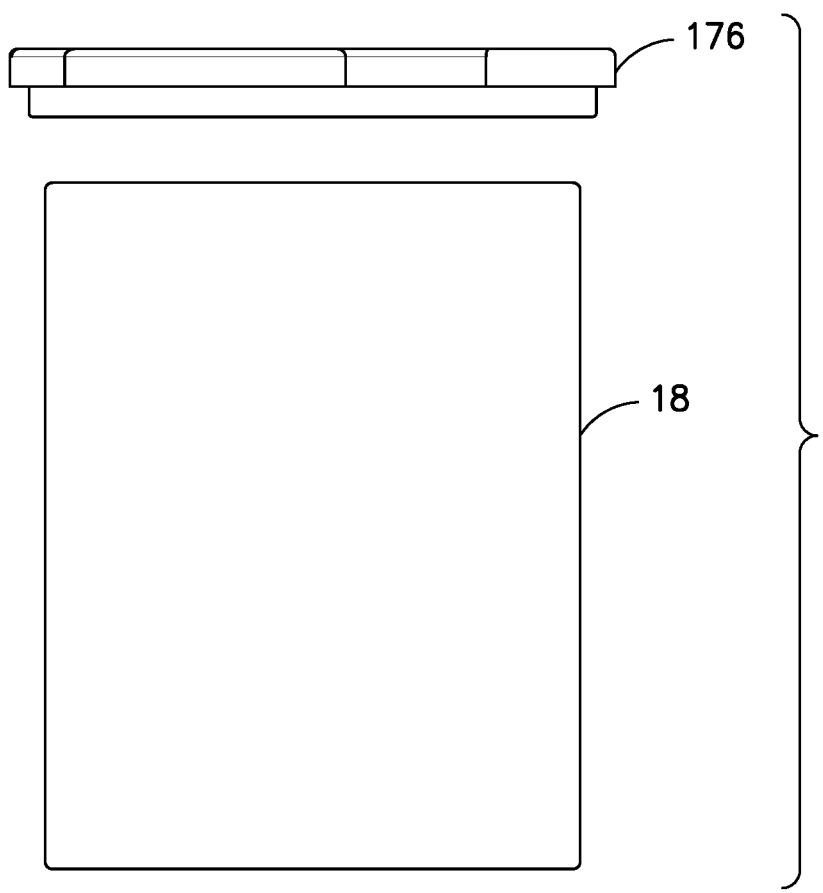
FIG. 43 is a side elevation view of a lid and an oxygen absorber in accordance with an embodiment of the present invention.

Next, partition member 160 is received within packaging member 12A as shown in FIGS. 31 and 33. To secure partition member 160 within packaging member 12A, partition member 160 is positioned within the second compartment 102A side of compartment portion 120A and partition member 160 is inserted or moved axially into packaging member 12A in a direction generally along arrow A (FIG. 1). In one embodiment, notches 162 of partition member 160 provide a feature to hold during placement of partition member 160 within packaging member 12A. As additional force is exerted on partition member 160 to axially move partition member 160 in the direction generally along arrow A within packaging member 12A, partition member 160 deforms first bump 154 of packaging member 12A outward until partition member 160 advances beyond, i.e., slides over and past, first bump 154 of packaging member 12A and locks partition member 160 between first bump 154 and second bump 156 as shown in FIGS. 31 and 33. Once partition member 160 slides over and past first bump 154 of packaging member 12A, first bump 154 returns to its undeformed or original position. In this position, referring to FIGS. 31 and 33, first bump 154 and second bump 156 abut, contact, or engage partition member 160 and lock or secure partition member 160 to packaging member 12A between first bump 154 and second bump 156 as shown in FIGS. 31 and 33. This configuration ensures that partition member 160 is secured to packaging member 12A, such that significant relative movement between partition member 160 and packaging member 12A is prevented. In this manner, partition member 160 and packaging member 12A define the second compartment 102A and the third compartment 104A. The first compartment 100A is sized and adapted to receive syringe barrel 14 therein, the second compartment 102A is sized and adapted to receive plunger rod 16 therein, and the third compartment 104A is sized and adapted to receive oxygen absorber 18 therein. The first compartment 100A, the second compartment 102A, and the third compartment 104A are in gaseous communication theretogether. In one embodiment, gas holes 164 of partition member 160 and gas slot 152 of separator wall 150 provide gaseous communication between the compartments 100A, 102A, and 104A. In this manner, with the packaging member 12A enclosing the syringe barrel 14, the plunger rod 16, and the oxygen absorber 18, the oxygen absorber 18 is adapted to draw oxygen from the syringe barrel 14 and to absorb oxygen contained within the first compartment 100A, the second compartment 102A, and the third compartment 104A of the packaging member 12A.

Additionally, with partition member 160 secured to packaging member 12A as described above, such that significant relative movement between partition member 160 and packaging member 12A is prevented, partition member 160 and packaging member 12A provide a third compartment 104A that secures oxygen absorber 18 within packaging member 12A such that oxygen absorber 18 is prevented from being removed from packaging member 12A.

Next, syringe barrel 14 is inserted into first compartment 100A of packaging member 12A as described above. With syringe barrel 14 properly inserted into first compartment 100A of packaging member 12A, plunger rod 16 is then inserted into second compartment 102A of packaging member 12A as described above.

As discussed above, after syringe packaging system 10A is properly sterilized, at least a portion of syringe barrel 14 may be properly inserted into first compartment 100A of packaging member 12A; at least a portion of plunger rod 16 may be properly inserted into second compartment 102A of packaging member 12A; and at least a portion of oxygen absorber 18 may be properly inserted into third compartment 104A of packaging member 12A. Next, sealing member 15 (FIG. 2B) is used to cooperate with packaging member 12A to seal syringe barrel 14, plunger rod 16, and oxygen absorber 18 within packaging member 12A, i.e., sealing member 15 and packaging member 12A together provide a substantially impermeable enclosure which provides a leak prevention and protection enclosure, protects the contents of syringe barrel 14, plunger rod 16, and oxygen absorber 18 contained within packaging member 12A, and/or maintains a sealed, sterilized environment within packaging member 12A. Additionally, sealing member 15 and packaging member 12A together provide an additional mechanism to reduce oxygen levels within packaging member 12A by sealing syringe barrel 14, plunger rod 16, and oxygen absorber 18 within packaging member 12A to prevent oxygen external to syringe packaging system 10A from entering the sealed packaging member 12A. Sealing member 15 and packaging member 12A together provide a sufficient seal at a range of temperatures, pressures, and humidity levels.

FIGS. 34-44 illustrate another exemplary embodiment of the present disclosure. Referring to FIGS. 15-23 and 34-44, a syringe packaging system 10B includes a packaging member 12B, a syringe assembly 13 including a syringe barrel 14 and a detachable plunger rod 16, an oxygen absorber 18, a stopper 19, and a stopper adapter 21. With the packaging member 12B enclosing the syringe barrel 14, the plunger rod 16, and the oxygen absorber 18, the oxygen absorber 18 is adapted to draw oxygen from the syringe barrel 14 and to absorb oxygen contained within the packaging member 12B. The syringe packaging system 10B of the present disclosure also allows for reduced storage space of a syringe assembly.

The exemplary embodiment illustrated in FIGS. 34-44 includes similar components to the embodiment illustrated in FIGS. 1-9. For the sake of brevity, these similar components and the similar steps of using syringe packaging system 10B will not all be discussed in conjunction with the embodiment illustrated in FIGS. 34-44. In one embodiment, syringe packaging system 10B is compatible with the syringe assembly 13 and the oxygen absorber 18 shown in FIGS. 15-23.

Referring to FIGS. 34-44, a syringe packaging system 10B includes a packaging member 12B formed of a generally oxygen impermeable material. In one embodiment, a sealing member 15 (FIG. 2B) may be removably attached to packaging member 12B. Packaging member 12B is sized and adapted to receive each of syringe barrel 14, plunger rod 16, and oxygen absorber 18 therein as will be described in more detail below.

Referring to FIGS. 34-44, packaging member 12B includes a first compartment 100B, a second compartment 102B, a third compartment 104B, a first or top end 110B, a second or bottom end 112B, and a sidewall 114B extending between top end 110B and bottom end 112B. Packaging member 12B includes a locking lip 116B at top end 110B. Disposed below locking lip 116B is an upper tray portion 118B having a cross-section that has a greater area than a cross-section disposed below upper tray portion 118B, i.e., a compartment portion 120B, such that a shoulder 122B is defined therebetween. The compartment portion 120B includes a separator wall 170 disposed therein such that separator wall 170 divides compartment portion 120B into first compartment 100B and second compartment 102B. The separator wall 170 defines a gas slot 172 which maintains first compartment 100B and second compartment 102B in gaseous communication theretogether. The second compartment 102B includes an internal wall or oxygen absorber chamber 174 adjacent bottom end 112B of packaging member 12B. Oxygen absorber chamber 174 forms third compartment 104B sized and adapted to receive the oxygen absorber 18 therein. In one embodiment, the first compartment 100B, the second compartment 102B, and the third compartment 104B of packaging member 12B are formed as a unitary packaging member component or compartment.

Referring to FIGS. 39-44, syringe packaging system 10B includes a lid 176 that is receivable within the oxygen absorber chamber 174 of packaging member 12B. The lid 176 defines an aperture 178. In one embodiment, lid 176 is sized and adapted to be securable to oxygen absorber chamber 174 by an interference fit. The aperture 178 of lid 176 provides for efficient performance of the oxygen absorber 18 contained within oxygen absorber chamber 174 and maintains the first compartment 100B, the second compartment 102B, and the third compartment 104B in gaseous communication theretogether.

All of the components of syringe packaging system 10B may be constructed of any known material, and are desirably constructed of medical-grade polymers.

Figure 44:
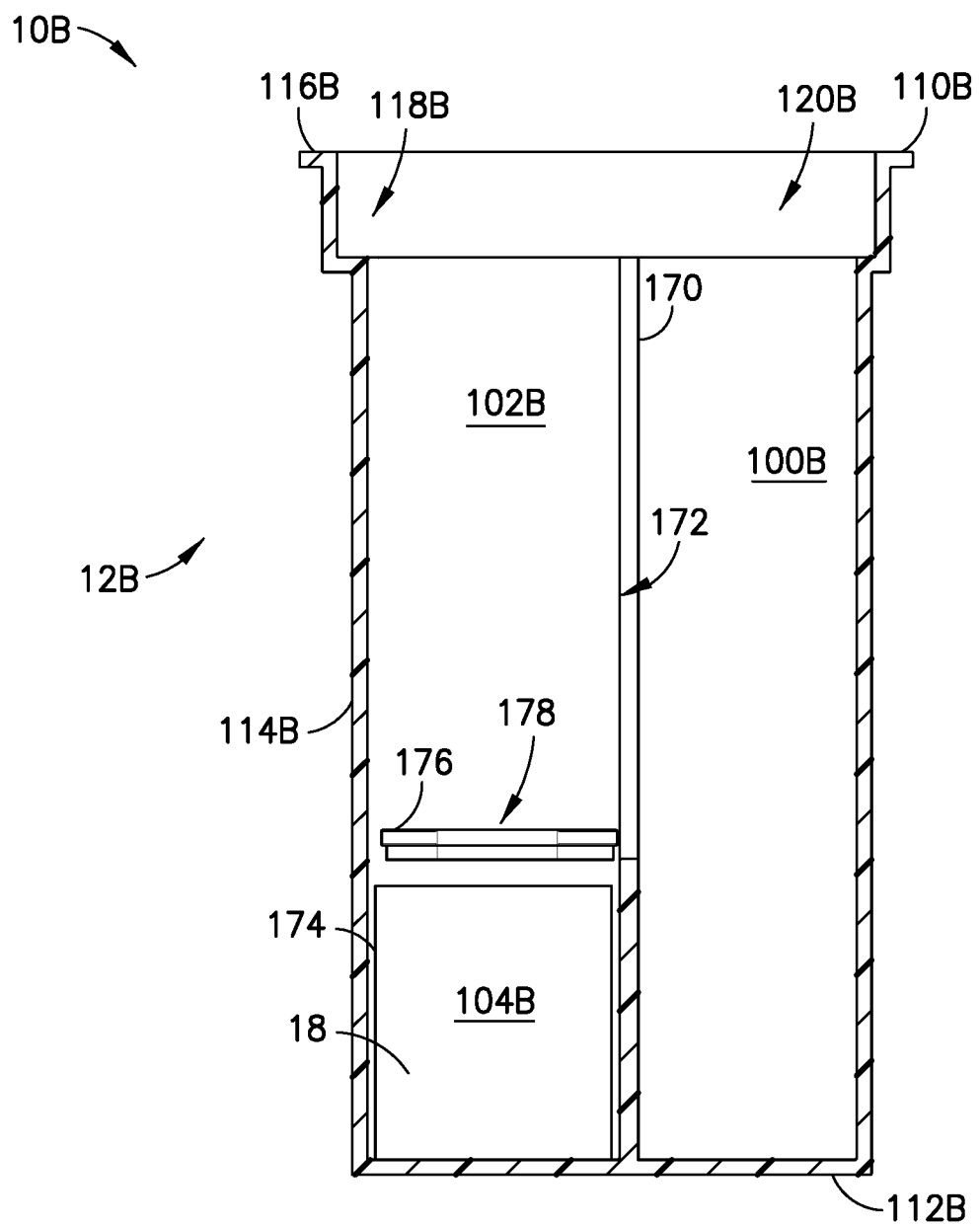
FIG. 44 is a schematic cross-sectional view of a syringe packaging system in accordance with an embodiment of the present invention.
Figure 47:
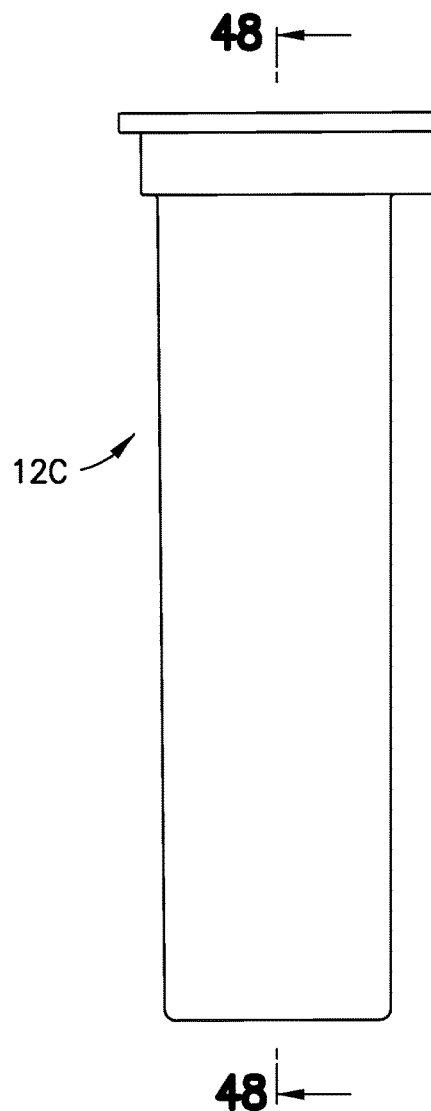
FIG. 47 is a side elevation view of a packaging member in accordance with an embodiment of the present invention.
Figure 48:
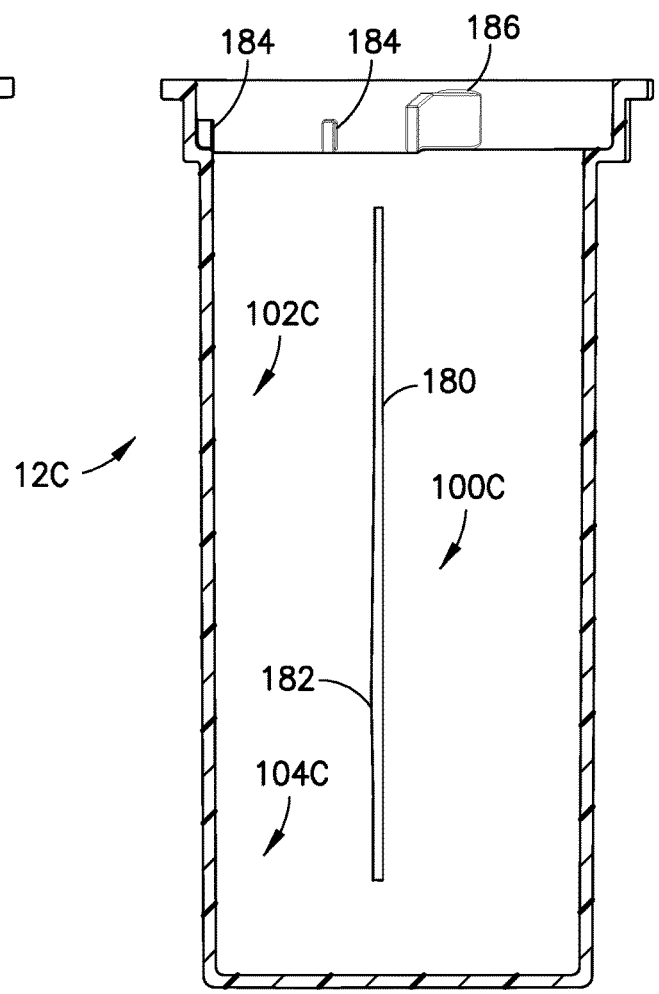
FIG. 48 is a cross-sectional view of a packaging member taken along line 48-48 of FIG. 47 in accordance with an embodiment of the present invention.

Referring to FIGS. 34-44, packaging of syringe barrel 14, plunger rod 16, and oxygen absorber 18 within packaging member 12B will now be described. Initially, syringe barrel 14, plunger rod 16, and packaging member 12B are sterilized according to techniques known to those of ordinary skill in the art as described above. In some embodiments, syringe barrel 14 may be pre-filled as described above. Next, oxygen absorber 18 is inserted into the third compartment 104B of packaging member 12B, i.e., oxygen absorber chamber 174, such that oxygen absorber 18 is positioned vertically within oxygen absorber chamber 174 as shown in FIG. 44.

Next, lid 176 is secured to oxygen absorber chamber 174 using an interference fit as shown in FIG. 44. This configuration ensures that lid 176 is secured to oxygen absorber chamber 174, such that significant relative movement between lid 176 and oxygen absorber chamber 174 is prevented. In this manner, lid 176 and oxygen absorber chamber 174 define the second compartment 102B and the third compartment 104B. The first compartment 100B is sized and adapted to receive syringe barrel 14 therein, the second compartment 102B is sized and adapted to receive plunger rod 16 therein, and the third compartment 104B is sized and adapted to receive oxygen absorber 18 therein. The first compartment 100B, the second compartment 102B, and the third compartment 104B are in gaseous communication theretogether. In this manner, with the packaging member 12B enclosing the syringe barrel 14, the plunger rod 16, and the oxygen absorber 18, the oxygen absorber 18 is adapted to draw oxygen from the syringe barrel 14 and to absorb oxygen contained within the first compartment 100B, the second compartment 102B, and the third compartment 104B of the packaging member 12B.

Additionally, with lid 176 secured to oxygen absorber chamber 174 as described above, such that significant relative movement between lid 176 and oxygen absorber chamber 174 is prevented, lid 176 and oxygen absorber chamber 174 provide a third compartment 104B that secures oxygen absorber 18 within packaging member 12B such that oxygen absorber 18 is prevented from being removed from packaging member 12B.

Next, syringe barrel 14 is inserted into first compartment 100B of packaging member 12B as described above. With syringe barrel 14 properly inserted into first compartment 100B of packaging member 12B, plunger rod 16 is then inserted into second compartment 102B of packaging member 12B as described above.

As discussed above, after syringe packaging system 10B is properly sterilized, at least a portion of syringe barrel 14 may be properly inserted into first compartment 100B of packaging member 12B; at least a portion of plunger rod 16 may be properly inserted into second compartment 102B of packaging member 12B; and at least a portion of oxygen absorber 18 may be properly inserted into third compartment 104B of packaging member 12B. Next, sealing member 15 (FIG. 2B) is used to cooperate with packaging member 12B to seal syringe barrel 14, plunger rod 16, and oxygen absorber 18 within packaging member 12B, i.e., sealing member 15 and packaging member 12B together provide a substantially impermeable enclosure which provides a leak prevention and protection enclosure, protects the contents of syringe barrel 14, plunger rod 16, and oxygen absorber 18 contained within packaging member 12B, and/or maintains a sealed, sterilized environment within packaging member 12B. Additionally, sealing member 15 and packaging member 12B together provide an additional mechanism to reduce oxygen levels within packaging member 12B by sealing syringe barrel 14, plunger rod 16, and oxygen absorber 18 within packaging member 12B to prevent oxygen external to syringe packaging system 10B from entering the sealed packaging member 12B. Sealing member 15 and packaging member 12B together provide a sufficient seal at a range of temperatures, pressures, and humidity levels.

FIGS. 45-53 illustrate another exemplary embodiment of the present disclosure. Referring to FIGS. 15-23 and 45-53, a syringe packaging system 10C includes a packaging member 12C, a syringe assembly 13 including a syringe barrel 14 and a detachable plunger rod 16, an oxygen absorber 18, a stopper 19, and a stopper adapter 21. With the packaging member 12C enclosing the syringe barrel 14, the plunger rod 16, and the oxygen absorber 18, the oxygen absorber 18 is adapted to draw oxygen from the syringe barrel 14 and to absorb oxygen contained within the packaging member 12C. The syringe packaging system 10C of the present disclosure also allows for reduced storage space of a syringe assembly.

The exemplary embodiment illustrated in FIGS. 45-53 includes similar components to the embodiment illustrated in FIGS. 1-9. For the sake of brevity, these similar components and the similar steps of using syringe packaging system 10C will not all be discussed in conjunction with the embodiment illustrated in FIGS. 45-53. In one embodiment, syringe packaging system 10C is compatible with the syringe assembly 13 and the oxygen absorber 18 shown in FIGS. 15-23.

Referring to FIGS. 45-53, a syringe packaging system 10C includes a packaging member 12C formed of a generally oxygen impermeable material. In one embodiment, a sealing member 15 (FIG. 2B) may be removably attached to packaging member 12C. Packaging member 12C is sized and adapted to receive each of syringe barrel 14, plunger rod 16, and oxygen absorber 18 therein as will be described in more detail below.

Figures 49, 50:
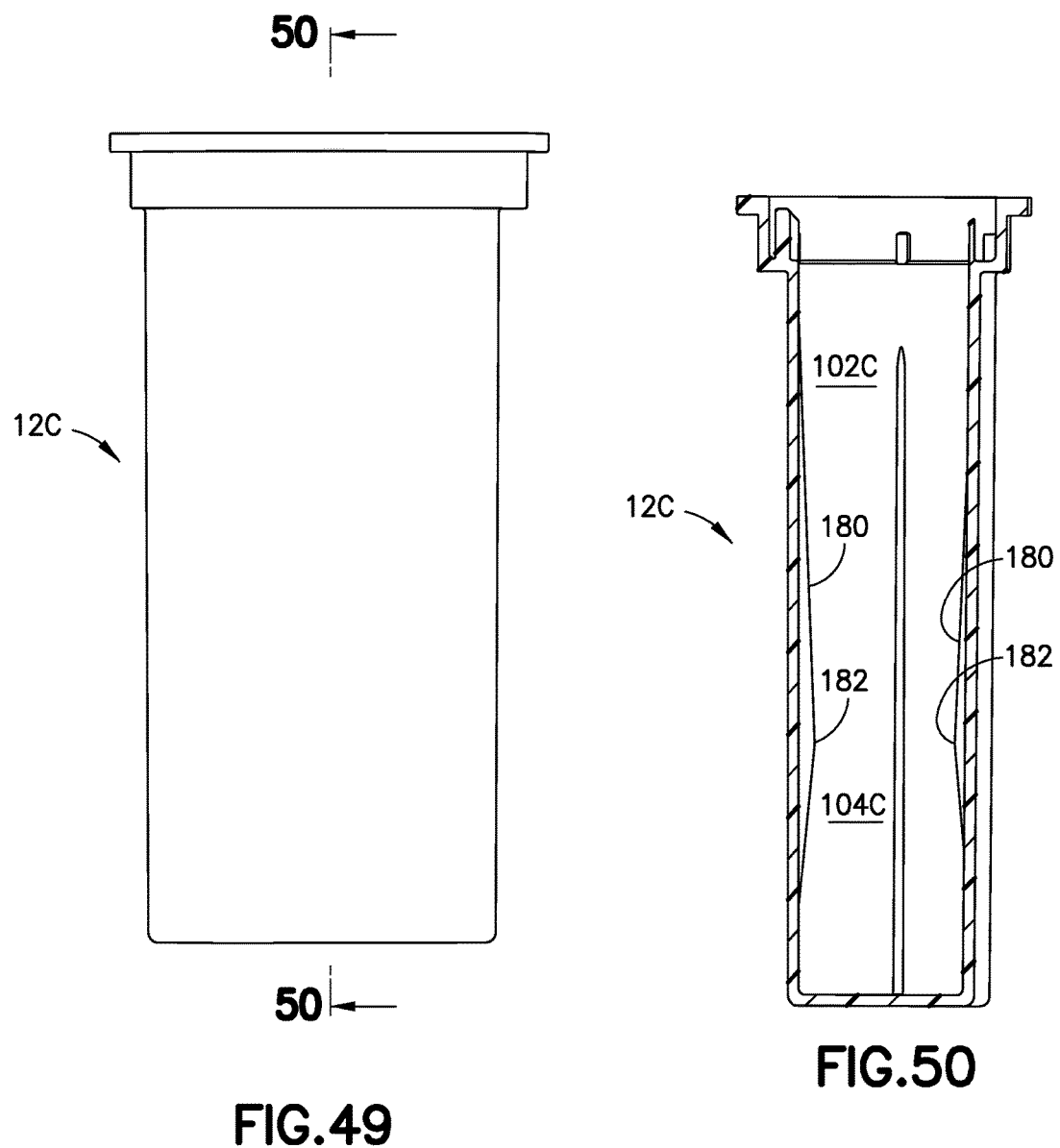
FIG. 49 is another side elevation view of a packaging member in accordance with an embodiment of the present invention.
FIG. 50 is a cross-sectional view of a packaging member taken along line 50-50 of FIG. 49 in accordance with an embodiment of the present invention.
Figure 51:
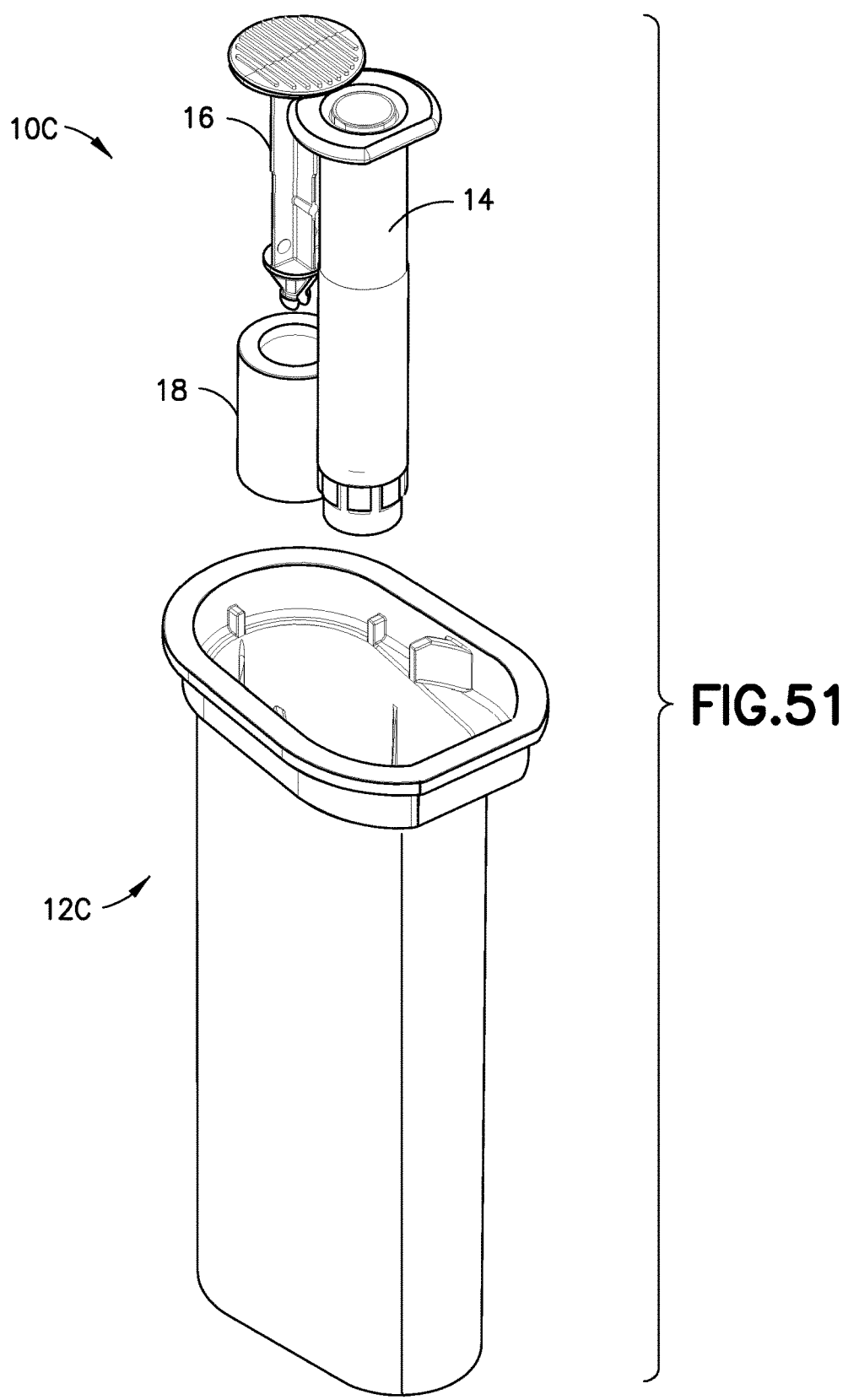
FIG. 51 is an exploded, perspective view of a syringe packaging system in accordance with an embodiment of the present invention.
Figure 52:
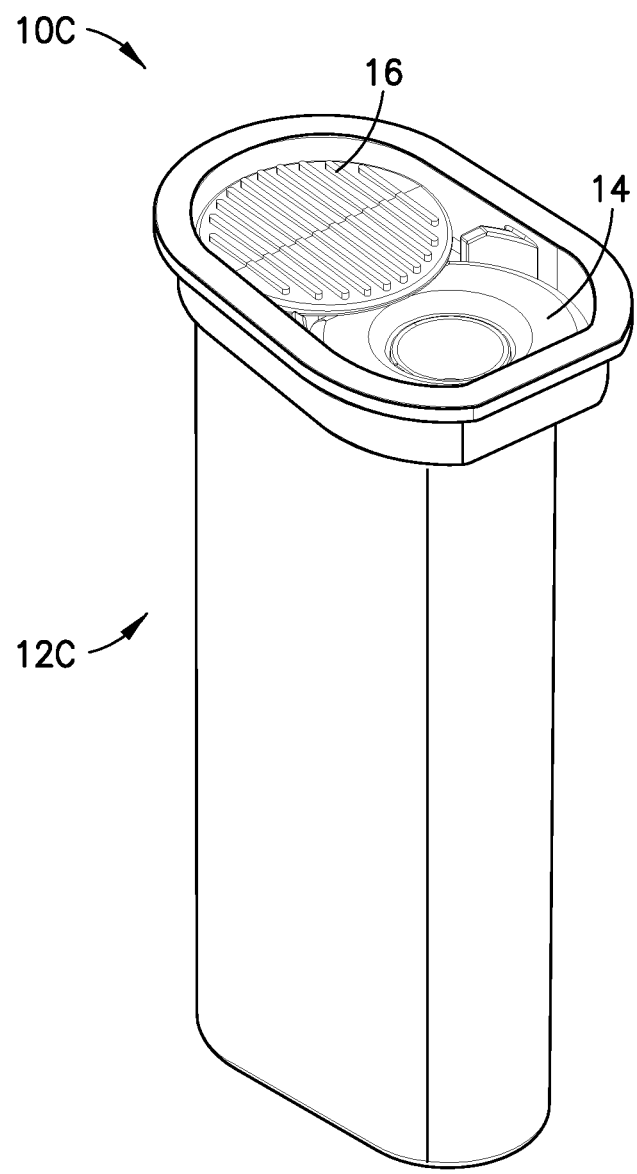
FIG. 52 is an assembled, perspective view of the syringe packaging system of FIG. 51 in accordance with an embodiment of the present invention.

Referring to FIGS. 45-53, packaging member 12C includes a first compartment 100C, a second compartment 102C, a third compartment 104C, a first or top end 110C, a second or bottom end 112C, and a sidewall 114C extending between top end 110C and bottom end 112C. Packaging member 12C includes a locking lip 116C at top end 110C. Disposed below locking lip 116C is an upper tray portion 118C having a cross-section that has a greater area than a cross-section disposed below upper tray portion 118C, i.e., a compartment portion 120C, such that a shoulder 122C is defined therebetween. Upper tray portion 118C receives and supports flange 40 of syringe barrel 14 and flange 74 of plunger rod 16 as will be described in more detail below. An interior surface of sidewall 114C of packaging member 12C includes opposing angled ribs 180 extending along a longitudinal axis of packaging member 12C. The opposing angled ribs 180 define peaks 182 as shown in FIG. 50.

In one embodiment, the angled ribs 180 divide compartment portion 120C into the first compartment 100C and the second compartment 102C as shown in FIG. 46. In one embodiment, the peaks 182 of the angled ribs 180 divide compartment portion 120C into the second compartment 102C and the third compartment 104C as shown in FIG. 50. The first compartment 100C, the second compartment 102C, and the third compartment 104C are in gaseous communication theretogether. In one embodiment, the first compartment 100C, the second compartment 102C, and the third compartment 104C of packaging member 12C are formed as a unitary packaging member component or compartment.

Referring to FIGS. 45 and 46, upper tray portion 118C includes plunger rod support members 184 around a periphery of second compartment 102C and syringe barrel support members 186 around a periphery of first compartment 100C. Plunger rod support members 184 provide a further securement mechanism for engaging the plunger rod 16 to secure the plunger rod 16 within second compartment 102C of packaging member 12C. For example, referring to FIGS. 51 and 52, in one embodiment, as plunger rod 16 is inserted into second compartment 102C, the underside surface of flange 74 of plunger rod 16 engages plunger rod support members 184 to secure plunger rod 16 within packaging member 12C in a stable manner. Syringe barrel support members 186 provide a further securement mechanism for engaging the syringe barrel 14 to secure the syringe barrel 14 within first compartment 100C of packaging member 12C. For example, referring to FIGS. 51 and 52, in one embodiment, as syringe barrel 14 is inserted into first compartment 100C, the flange 40 of syringe barrel 14 engages syringe barrel support members 186 to secure syringe barrel 14 within packaging member 12C. In one embodiment, syringe barrel support members 186 provide a mechanism that allows the syringe barrel 14 to be positioned within packaging member 12C such that the flat end of flange 40 can be along one direction. In one embodiment, syringe barrel support members 186 serve as an anti-nesting mechanism during bulk packaging.

Referring to FIGS. 45 and 46, the bottom portion or bottom end 112C of packaging member 12C tapers from third compartment 104C side to first compartment 100C side. In this manner, the overall size of packaging member 12C is reduced.

All of the components of syringe packaging system 10C may be constructed of any known material, and are desirably constructed of medical-grade polymers.

Referring to FIGS. 45-53, packaging of syringe barrel 14, plunger rod 16, and oxygen absorber 18 within packaging member 12C will now be described. Initially, syringe barrel 14, plunger rod 16, and packaging member 12C are sterilized according to techniques known to those of ordinary skill in the art as described above. In some embodiments, syringe barrel 14 may be pre-filled as described above.

Figure 53:
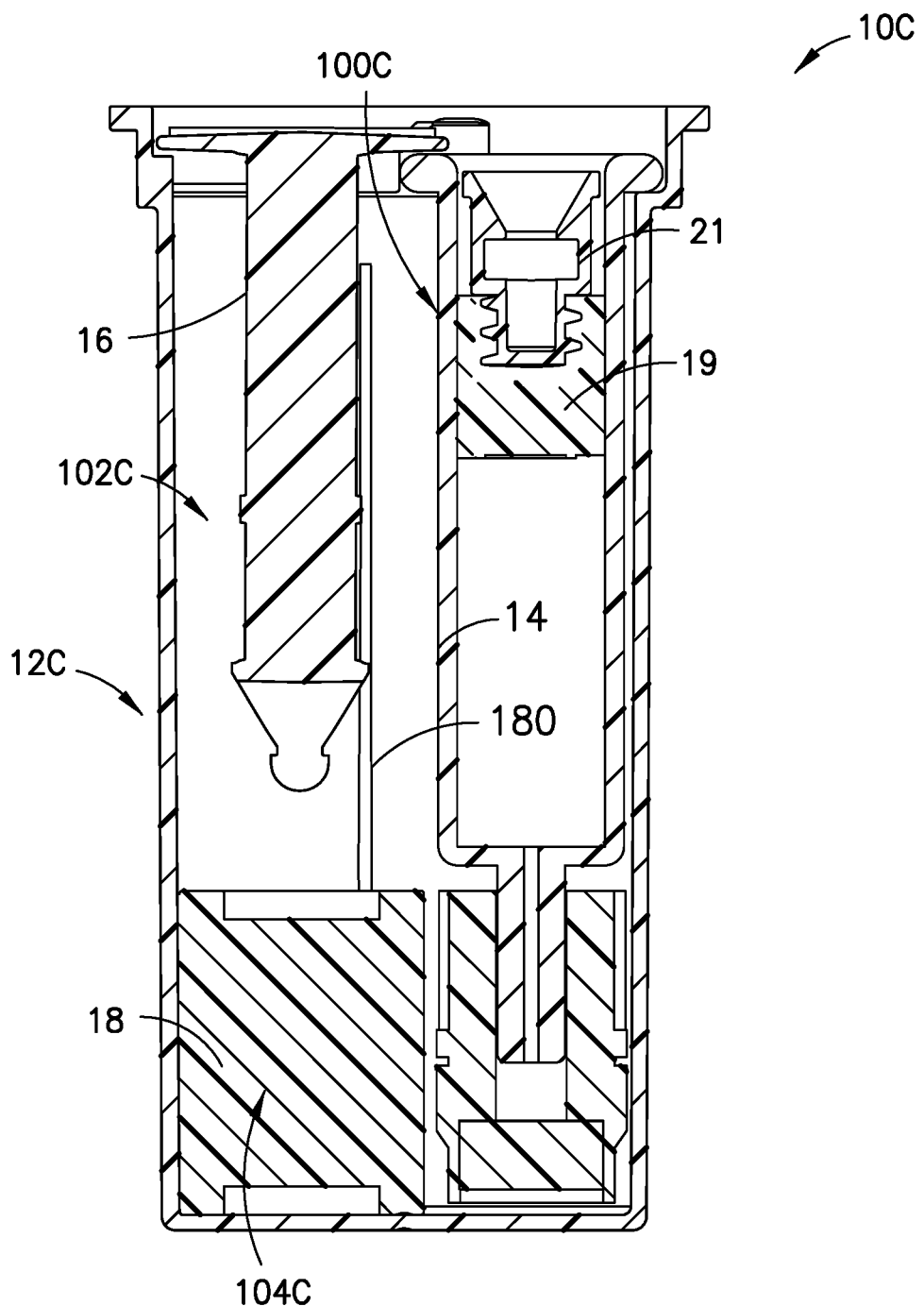
FIG. 53 is a cross-sectional view of the syringe packaging system of FIG. 52 in accordance with an embodiment of the present invention.

Next, oxygen absorber 18 is received within third compartment 104C of packaging member 12C such that oxygen absorber 18 is positioned vertically within third compartment 104C as shown in FIG. 53. To secure oxygen absorber 18 within third compartment 104C of packaging member 12C, oxygen absorber 18 is inserted or moved axially into packaging member 12C in a direction generally along arrow A (FIG. 1). As additional force is exerted on oxygen absorber 18 to axially move oxygen absorber 18 in the direction generally along arrow A within packaging member 12C, oxygen absorber 18 deforms peaks 182 of angled ribs 180 of packaging member 12C outward until oxygen absorber 18 advances beyond, i.e., slides over and past, peaks 182 of angled ribs 180 of packaging member 12C and locks oxygen absorber 18 within third compartment 104C of packaging member 12C as shown in FIG. 53. Once oxygen absorber 18 slides over and past peaks 182 of angled ribs 180 of packaging member 12C, peaks 182 of angled ribs 180 return to their undeformed or original position. In this position, peaks 182 of angled ribs 180 may abut, contact, or engage oxygen absorber 18 and lock or secure oxygen absorber 18 within third compartment 104C of packaging member 12C. This configuration ensures that packaging member 12C provides a third compartment 104C that secures oxygen absorber 18 within packaging member 12C such that oxygen absorber 18 is prevented from being removed from packaging member 12C. This configuration also ensures that the oxygen absorber 18 is maintained within the third compartment 104C and is not able to slide towards the first compartment 100C.

Syringe packaging system 10C provides a system that has minimal or no interference between packaging member 12C and oxygen absorber 18 once oxygen absorber 18 is properly positioned within third compartment 104C. In this manner, there is very minimal or no stress exerted on the packaging member 12C and/or the oxygen absorber 18.

Next, syringe barrel 14 is inserted into first compartment 100C of packaging member 12C as described above. With syringe barrel 14 properly inserted into first compartment 100C of packaging member 12C, plunger rod 16 is then inserted into second compartment 102C of packaging member 12C as described above.

In this manner, with the packaging member 12C enclosing the syringe barrel 14, the plunger rod 16, and the oxygen absorber 18, the oxygen absorber 18 is adapted to draw oxygen from the syringe barrel 14 and to absorb oxygen contained within the first compartment 100C, the second compartment 102C, and the third compartment 104C of the packaging member 12C.

As discussed above, after syringe packaging system 10C is properly sterilized, at least a portion of syringe barrel 14 may be properly inserted into first compartment 100C of packaging member 12C; at least a portion of plunger rod 16 may be properly inserted into second compartment 102C of packaging member 12C; and at least a portion of oxygen absorber 18 may be properly inserted into third compartment 104C of packaging member 12C. Next, sealing member 15 (FIG. 2B) is used to cooperate with packaging member 12C to seal syringe barrel 14, plunger rod 16, and oxygen absorber 18 within packaging member 12C, i.e., sealing member 15 and packaging member 12C together provide a substantially impermeable enclosure which provides a leak prevention and protection enclosure, protects the contents of syringe barrel 14, plunger rod 16, and oxygen absorber 18 contained within packaging member 12C, and/or maintains a sealed, sterilized environment within packaging member 12C. Additionally, sealing member 15 and packaging member 12C together provide an additional mechanism to reduce oxygen levels within packaging member 12C by sealing syringe barrel 14, plunger rod 16, and oxygen absorber 18 within packaging member 12C to prevent oxygen external to syringe packaging system 10C from entering the sealed packaging member 12C. Sealing member 15 and packaging member 12C together provide a sufficient seal at a range of temperatures, pressures, and humidity levels.

FIGS. 54-61 illustrate another exemplary embodiment of the present disclosure. Referring to FIGS. 15-23 and 54-61, a syringe packaging system 10D includes a packaging member 12D, a syringe assembly 13 including a syringe barrel 14 and a detachable plunger rod 16, an oxygen absorber 18, a stopper 19, and a stopper adapter 21. With the packaging member 12D enclosing the syringe barrel 14, the plunger rod 16, and the oxygen absorber 18, the oxygen absorber 18 is adapted to draw oxygen from the syringe barrel 14 and to absorb oxygen contained within the packaging member 12D. The syringe packaging system 10D of the present disclosure also allows for reduced storage space of a syringe assembly.

The exemplary embodiment illustrated in FIGS. 54-61 includes similar components to the embodiment illustrated in FIGS. 1-9. For the sake of brevity, these similar components and the similar steps of using syringe packaging system 10D will not all be discussed in conjunction with the embodiment illustrated in FIGS. 54-61. In one embodiment, syringe packaging system 10D is compatible with the syringe assembly 13 and the oxygen absorber 18 shown in FIGS. 15-23.

Referring to FIGS. 54-61, a syringe packaging system 10D includes a packaging member 12D formed of a generally oxygen impermeable material. In one embodiment, a sealing member 15 (FIG. 2B) may be removably attached to packaging member 12D. Packaging member 12D is sized and adapted to receive each of syringe barrel 14, plunger rod 16, and oxygen absorber 18 therein as will be described in more detail below.

Referring to FIGS. 54-61, packaging member 12D includes a first compartment 100D, a second compartment 102D, a third compartment 104D, a first or top end 110D, a second or bottom end 112D, and a sidewall 114D extending between top end 110D and bottom end 112D. Packaging member 12D includes a locking lip 116D at top end 110D. Disposed below locking lip 116D is an upper tray portion 118D having a cross-section that has a greater area than a cross-section disposed below upper tray portion 118D, i.e., a compartment portion 120D, such that a shoulder 122D is defined therebetween. Upper tray portion 118D receives and supports flange 40 of syringe barrel 14 and flange 74 of plunger rod 16. An interior surface of sidewall 114D of packaging member 12D includes opposing fin elements 190 extending along a longitudinal axis of packaging member 12D. The opposing fin elements 190 include a lead-in portion 192, a top portion 194, and a bottom portion 196.

Figures 54, 55:
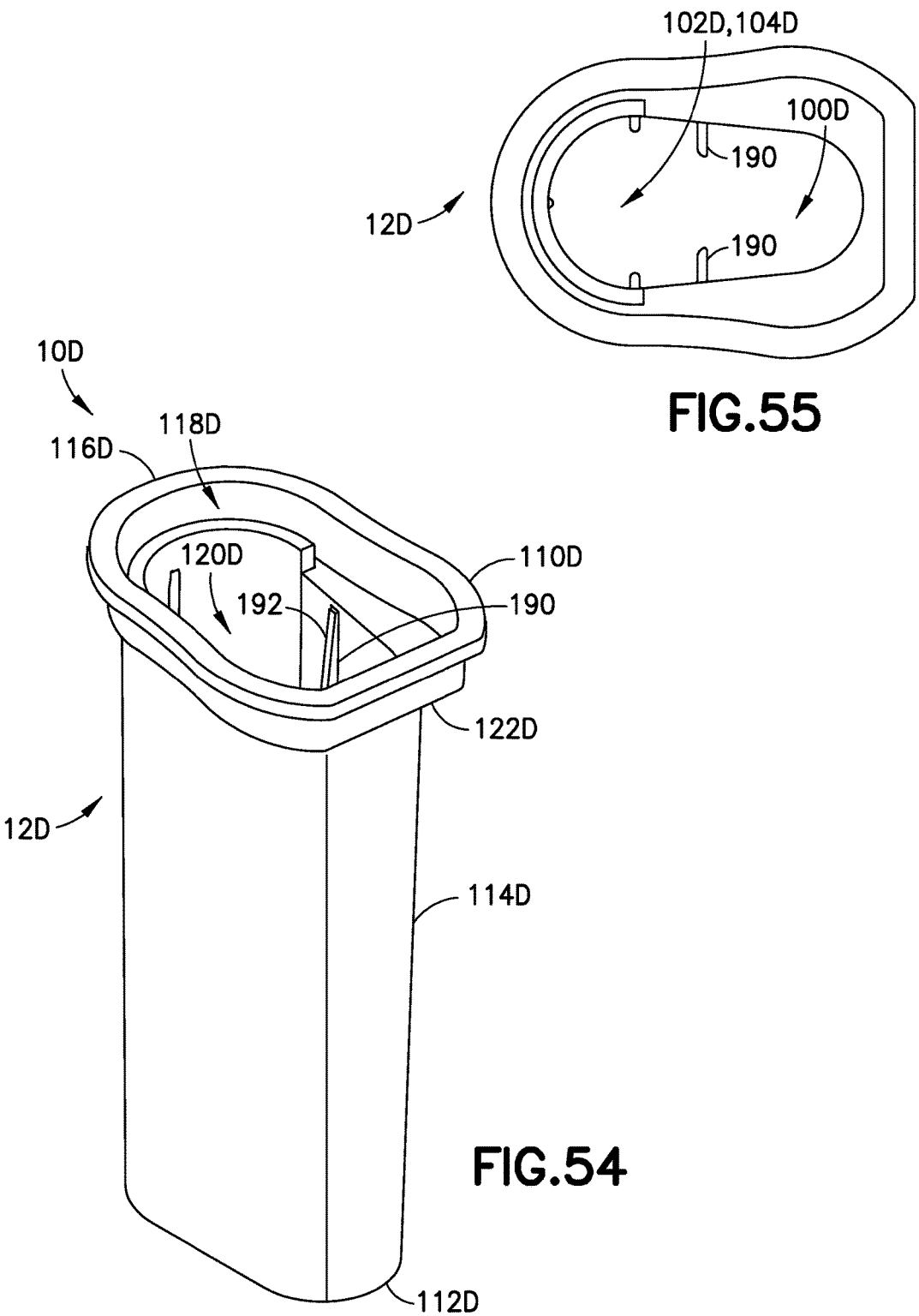
FIG. 54 is a perspective view of a packaging member in accordance with an embodiment of the present invention.
FIG. 55 is a top view of a packaging member in accordance with an embodiment of the present invention.
Figure 56:
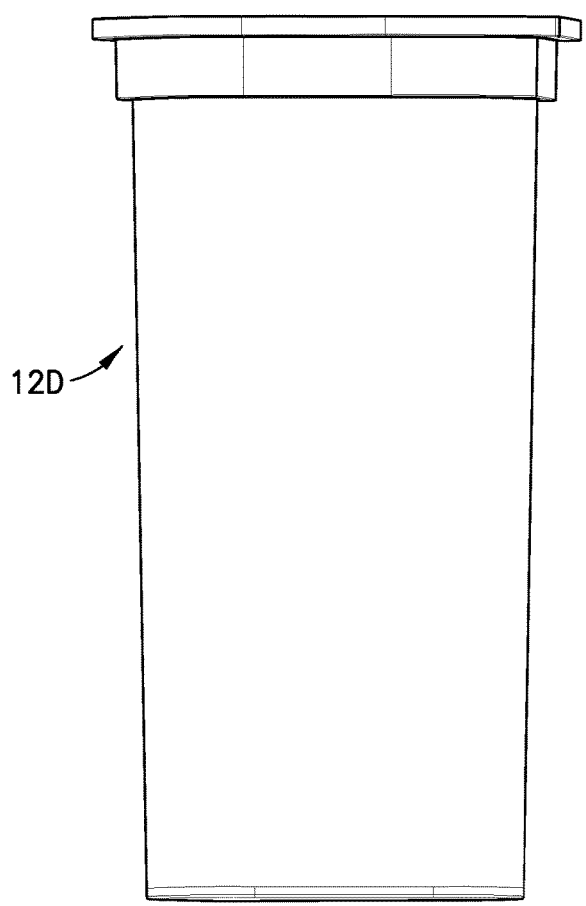
FIG. 56 is a side elevation view of a packaging member in accordance with an embodiment of the present invention.
Figure 57:
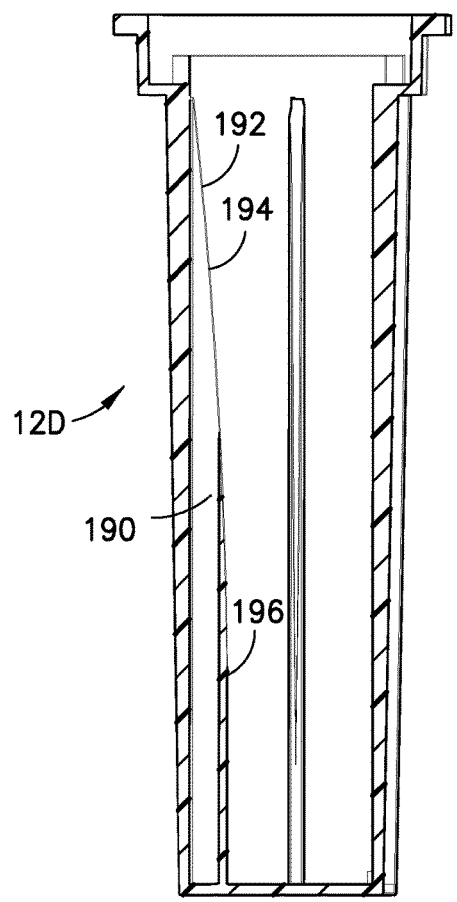
FIG. 57 is a cross-sectional view of a packaging member taken along line 57-57 of FIG. 56 in accordance with an embodiment of the present invention.
Figure 60:
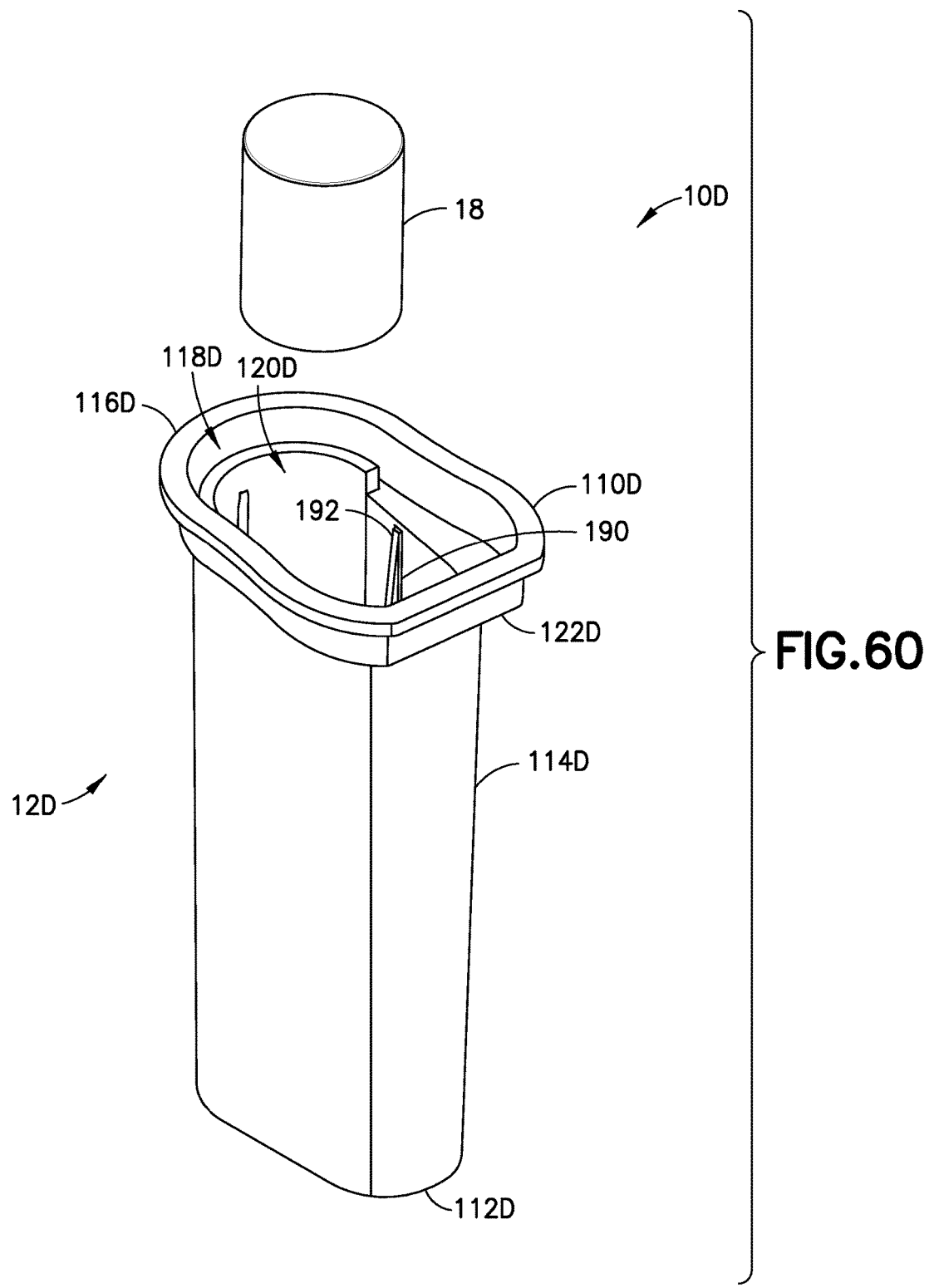
FIG. 60 is an exploded, perspective view of a syringe packaging system in accordance with an embodiment of the present invention.
Figure 61:
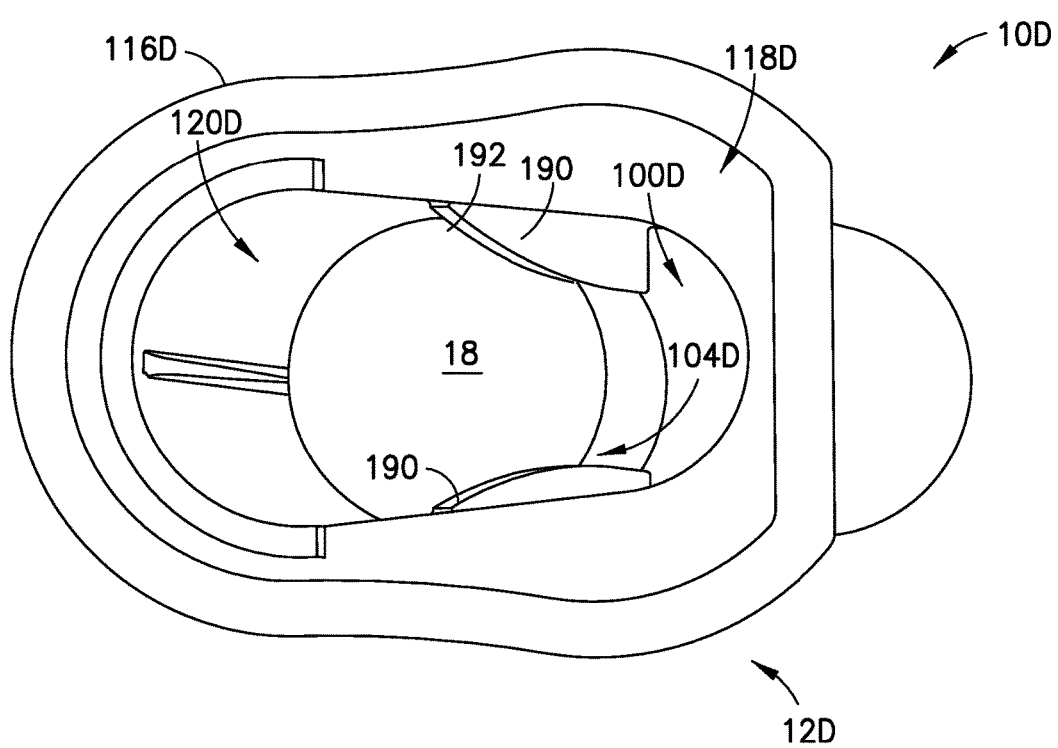
FIG. 61 is an assembled, top view of the syringe packaging system of FIG. 60 in accordance with an embodiment of the present invention.
Figures 62, 63:
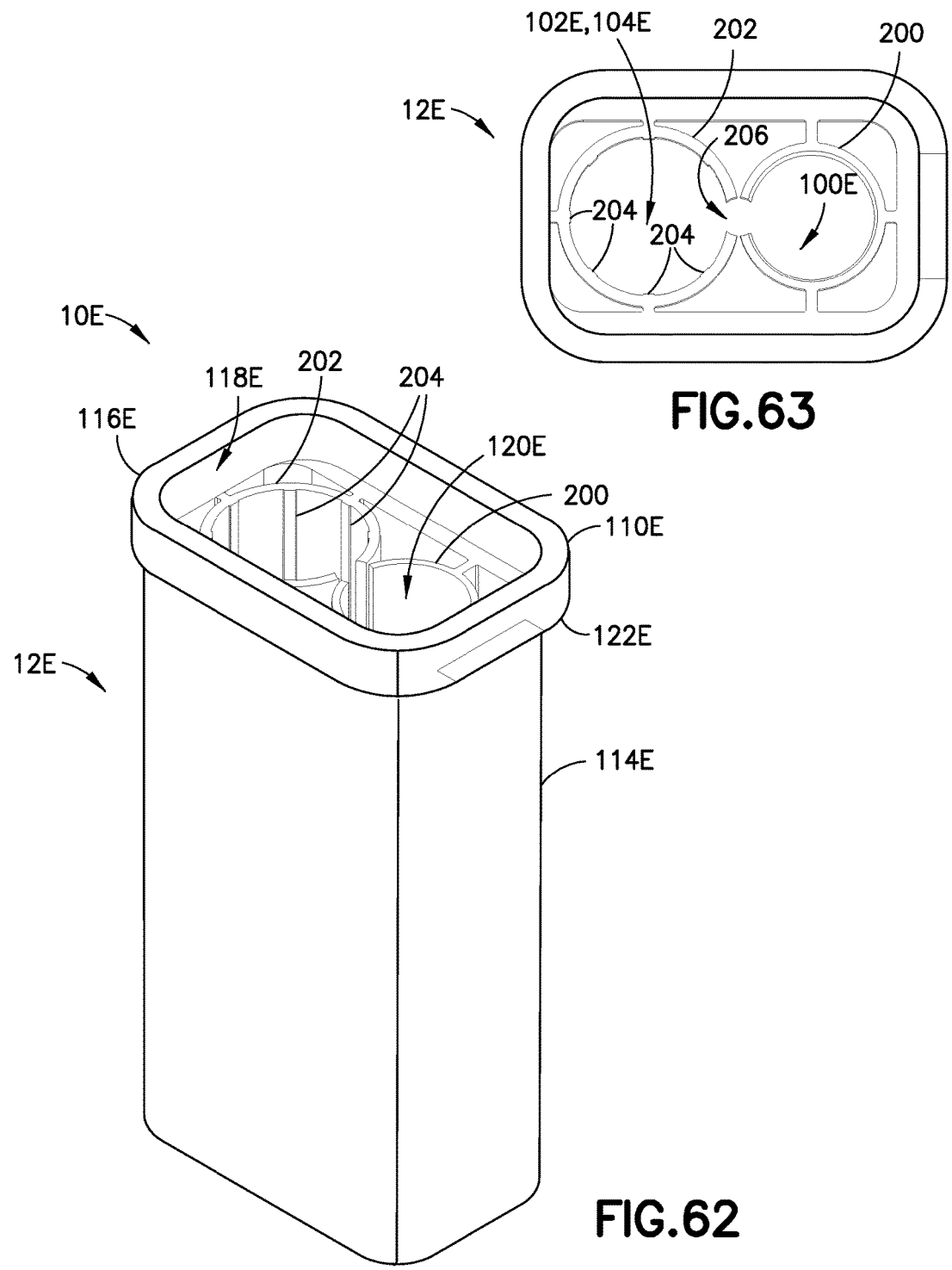
FIG. 62 is a perspective view of a packaging member in accordance with an embodiment of the present invention.
FIG. 63 is a top view of a packaging member in accordance with an embodiment of the present invention.
Figures 64, 65:
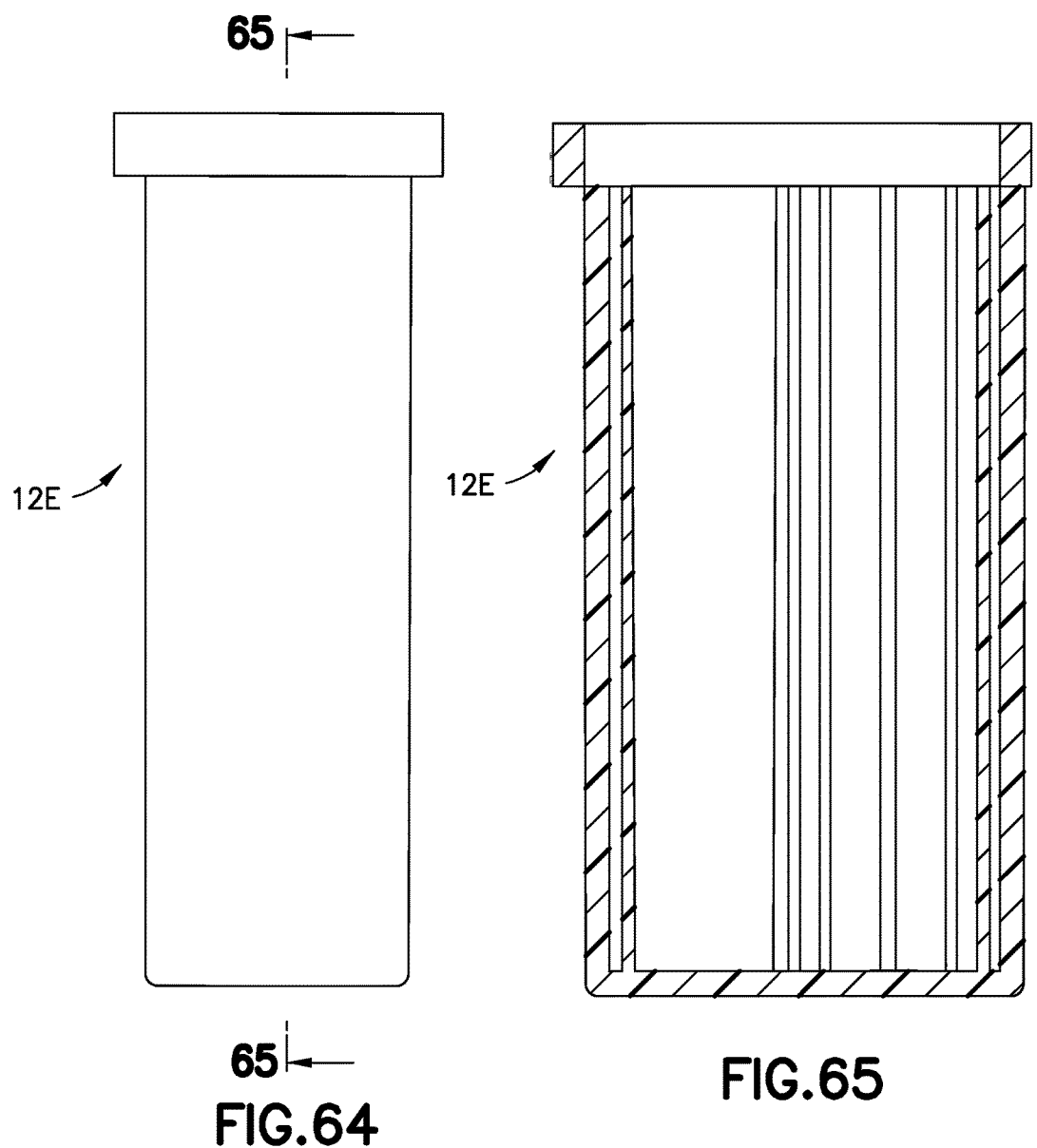
FIG. 64 is a side elevation view of a packaging member in accordance with an embodiment of the present invention.
FIG. 65 is a cross-sectional view of a packaging member taken along line 65-65 of FIG. 64 in accordance with an embodiment of the present invention.
Figure 66:
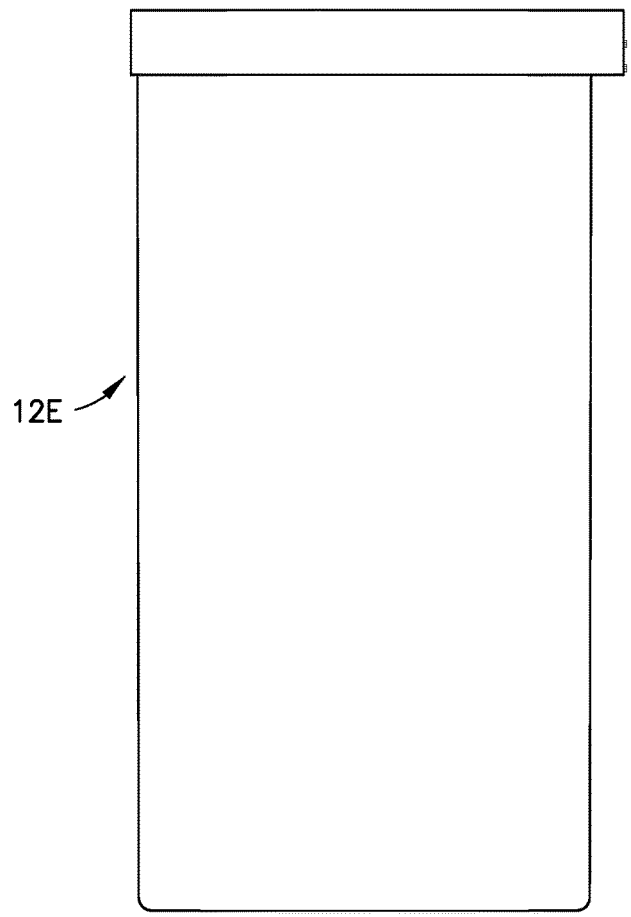
FIG. 66 is another side elevation view of a packaging member in accordance with an embodiment of the present invention.
Figure 67:
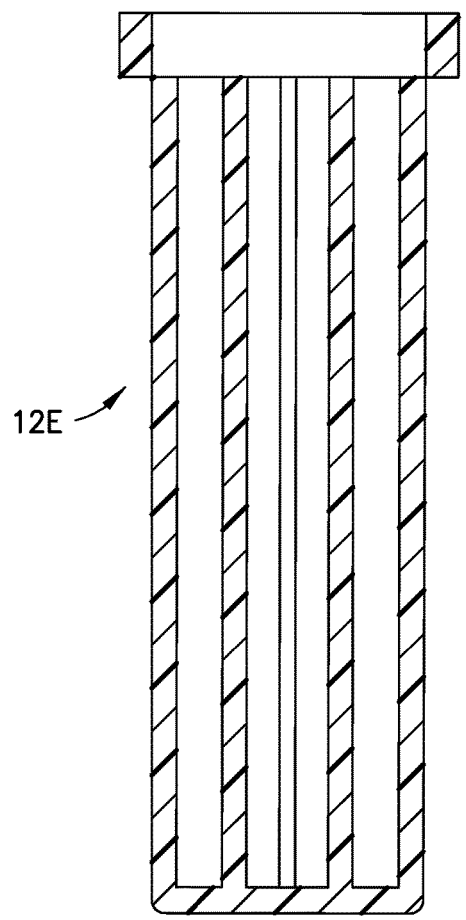
FIG. 67 is a cross-sectional view of a packaging member taken along line 67-67 of FIG. 66 in accordance with an embodiment of the present invention.
Figure 68:
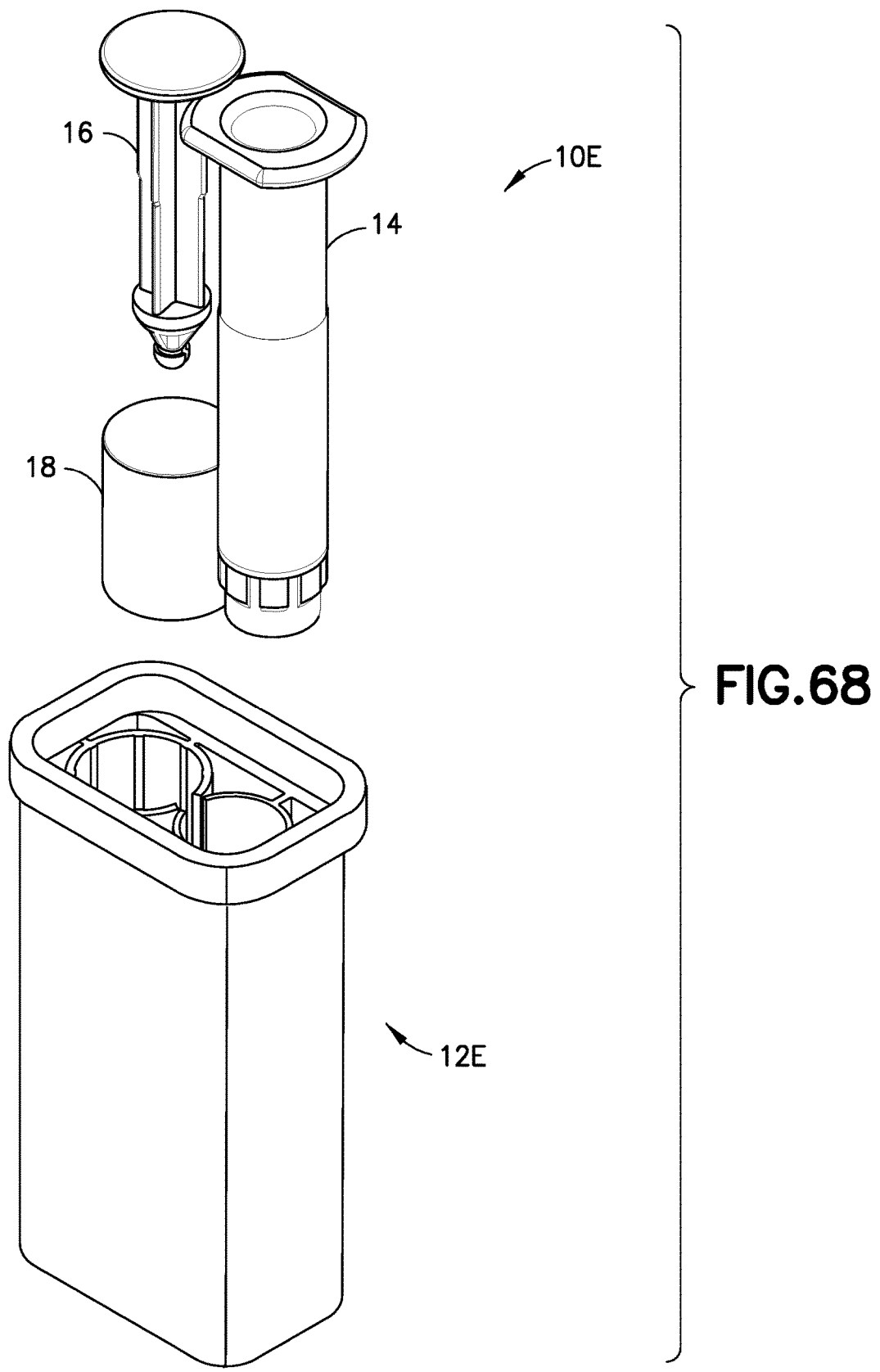
FIG. 68 is an exploded, perspective view of a syringe packaging system in accordance with an embodiment of the present invention.
Figure 69:
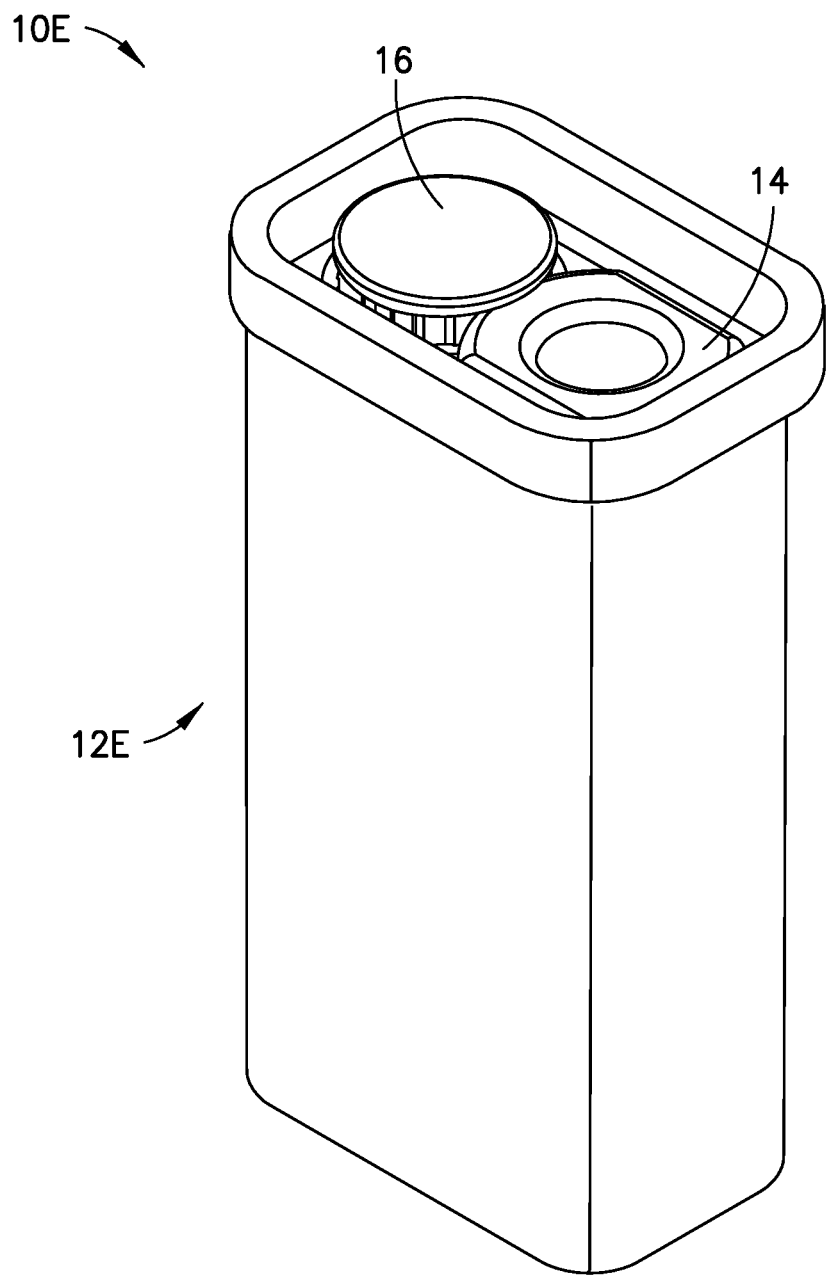
FIG. 69 is an assembled, perspective view of the syringe packaging system of FIG. 68 in accordance with an embodiment of the present invention.

In one embodiment, the fin elements 190 divide compartment portion 120D into the first compartment 100D and the second compartment 102D as shown in FIG. 55. In one embodiment, the top portion 194 and bottom portion 196 of fin elements 190 divide compartment portion 120D into the second compartment 102D and the third compartment 104D as shown in FIG. 57. The first compartment 100D, the second compartment 102D, and the third compartment 104D are in gaseous communication theretogether. In one embodiment, the first compartment 100D, the second compartment 102D, and the third compartment 104D of packaging member 12D are formed as a unitary packaging member component or compartment.

Referring to FIGS. 54 and 55, the bottom portion or bottom end 112D of packaging member 12D tapers from third compartment 104D side to first compartment 100D side. In this manner, the overall size of packaging member 12D is reduced.

All of the components of syringe packaging system 10D may be constructed of any known material, and are desirably constructed of medical-grade polymers.

Referring to FIGS. 54-61, packaging of syringe barrel 14, plunger rod 16, and oxygen absorber 18 within packaging member 12D will now be described. Initially, syringe barrel 14, plunger rod 16, and packaging member 12D are sterilized according to techniques known to those of ordinary skill in the art as described above. In some embodiments, syringe barrel 14 may be pre-filled as described above.

Next, oxygen absorber 18 is received within third compartment 104D of packaging member 12D such that oxygen absorber 18 is positioned vertically within third compartment 104D. To secure oxygen absorber 18 within third compartment 104D of packaging member 12D, oxygen absorber 18 is inserted or moved axially into packaging member 12D in a direction generally along arrow A (FIG. 1). The lead-in portion 192 of fin elements 190 provide a lead-in surface that helps with guiding and centering oxygen absorber 18 within packaging member 12D. As additional force is exerted on oxygen absorber 18 to axially move oxygen absorber 18 in the direction generally along arrow A within packaging member 12D, oxygen absorber 18 deforms a portion of fin elements 190 outward until oxygen absorber 18 advances beyond, i.e., slides over and past, the top portion 194 of fin elements 190 of packaging member 12D and locks oxygen absorber 18 within third compartment 104D of packaging member 12D. Once oxygen absorber 18 slides over and past top portion 194 of fin elements 190 of packaging member 12D, fin elements 190 return to their undeformed or original position. In this position, fin elements 190 may abut, contact, or engage oxygen absorber 18 and lock or secure oxygen absorber 18 within third compartment 104D of packaging member 12D by an interference fit between fin elements 190 and oxygen absorber 18. This configuration ensures that packaging member 12D provides a third compartment 104D that secures oxygen absorber 18 within packaging member 12D such that oxygen absorber 18 is prevented from being removed from packaging member 12D. This configuration also ensures that the oxygen absorber 18 is maintained within the third compartment 104D and is not able to slide towards the first compartment 100D.

Next, syringe barrel 14 is inserted into first compartment 100D of packaging member 12D as described above. With syringe barrel 14 properly inserted into first compartment 100D of packaging member 12D, plunger rod 16 is then inserted into second compartment 102D of packaging member 12D as described above.

In this manner, with the packaging member 12D enclosing the syringe barrel 14, the plunger rod 16, and the oxygen absorber 18, the oxygen absorber 18 is adapted to draw oxygen from the syringe barrel 14 and to absorb oxygen contained within the first compartment 100D, the second compartment 102D, and the third compartment 104D of the packaging member 12D.

FIGS. 62-70 illustrate another exemplary embodiment of the present disclosure. Referring to FIGS. 15-23 and 62-70, a syringe packaging system 10E includes a packaging member 12E, a syringe assembly 13 including a syringe barrel 14 and a detachable plunger rod 16, an oxygen absorber 18, a stopper 19, and a stopper adapter 21. With the packaging member 12E enclosing the syringe barrel 14, the plunger rod 16, and the oxygen absorber 18, the oxygen absorber 18 is adapted to draw oxygen from the syringe barrel 14 and to absorb oxygen contained within the packaging member 12E. The syringe packaging system 10E of the present disclosure also allows for reduced storage space of a syringe assembly.

The exemplary embodiment illustrated in FIGS. 62-70 includes similar components to the embodiment illustrated in FIGS. 1-9. For the sake of brevity, these similar components and the similar steps of using syringe packaging system 10E will not all be discussed in conjunction with the embodiment illustrated in FIGS. 62-70. In one embodiment, syringe packaging system 10E is compatible with the syringe assembly 13 and the oxygen absorber 18 shown in FIGS. 15-23.

Referring to FIGS. 62-70, a syringe packaging system 10E includes a packaging member 12E formed of a generally oxygen impermeable material. In one embodiment, a sealing member 15 (FIG. 2B) may be removably attached to packaging member 12E. Packaging member 12E is sized and adapted to receive each of syringe barrel 14, plunger rod 16, and oxygen absorber 18.

Referring to FIGS. 62-70, packaging member 12E includes a first compartment 100E, a second compartment 102E, a third compartment 104E, a first or top end 110E, a second or bottom end, and a sidewall 114E extending between top end 110E and bottom end. Packaging member 12E includes a locking lip 116E at top end 110E. Disposed below locking lip 116E is an upper tray portion 118E having a cross-section that has a greater area than a cross-section disposed below upper tray portion 118E, i.e., a compartment portion 120E, such that a shoulder 122E is defined therebetween. Upper tray portion 118E receives and supports flange 40 of syringe barrel 14 and flange 74 of plunger rod 16.

The compartment portion 120E includes a syringe barrel container 200 and a plunger rod and oxygen absorber container 202. The plunger rod and oxygen absorber container 202 forms second compartment 102E and third compartment 104E which are sized and adapted to receive the plunger rod 16 and the oxygen absorber 18 respectively therein. The syringe barrel container 200 forms first compartment 100E which is sized and adapted to receive the syringe barrel 14 therein. In one embodiment, the first compartment 100E, the second compartment 102E, and the third compartment 104E of packaging member 12E are formed as a unitary packaging member component or compartment. The syringe barrel container 200 and the plunger rod and oxygen absorber container 202 define a gas slot 206 which maintains first compartment 100E, second compartment 102E, and third compartment 104E in gaseous communication theretogether. The interior surface of plunger rod and oxygen absorber container 202 includes ribs 204 extending along a longitudinal axis of plunger rod and oxygen absorber container 202 of packaging member 12E.

All of the components of syringe packaging system 10E may be constructed of any known material, and are desirably constructed of medical-grade polymers.

Referring to FIGS. 62-70, packaging of syringe barrel 14, plunger rod 16, and oxygen absorber 18 within packaging member 12E will now be described. Initially, syringe barrel 14, plunger rod 16, and packaging member 12E are sterilized according to techniques known to those of ordinary skill in the art as described above. In some embodiments, syringe barrel 14 may be pre-filled as described above.

Figure 70:
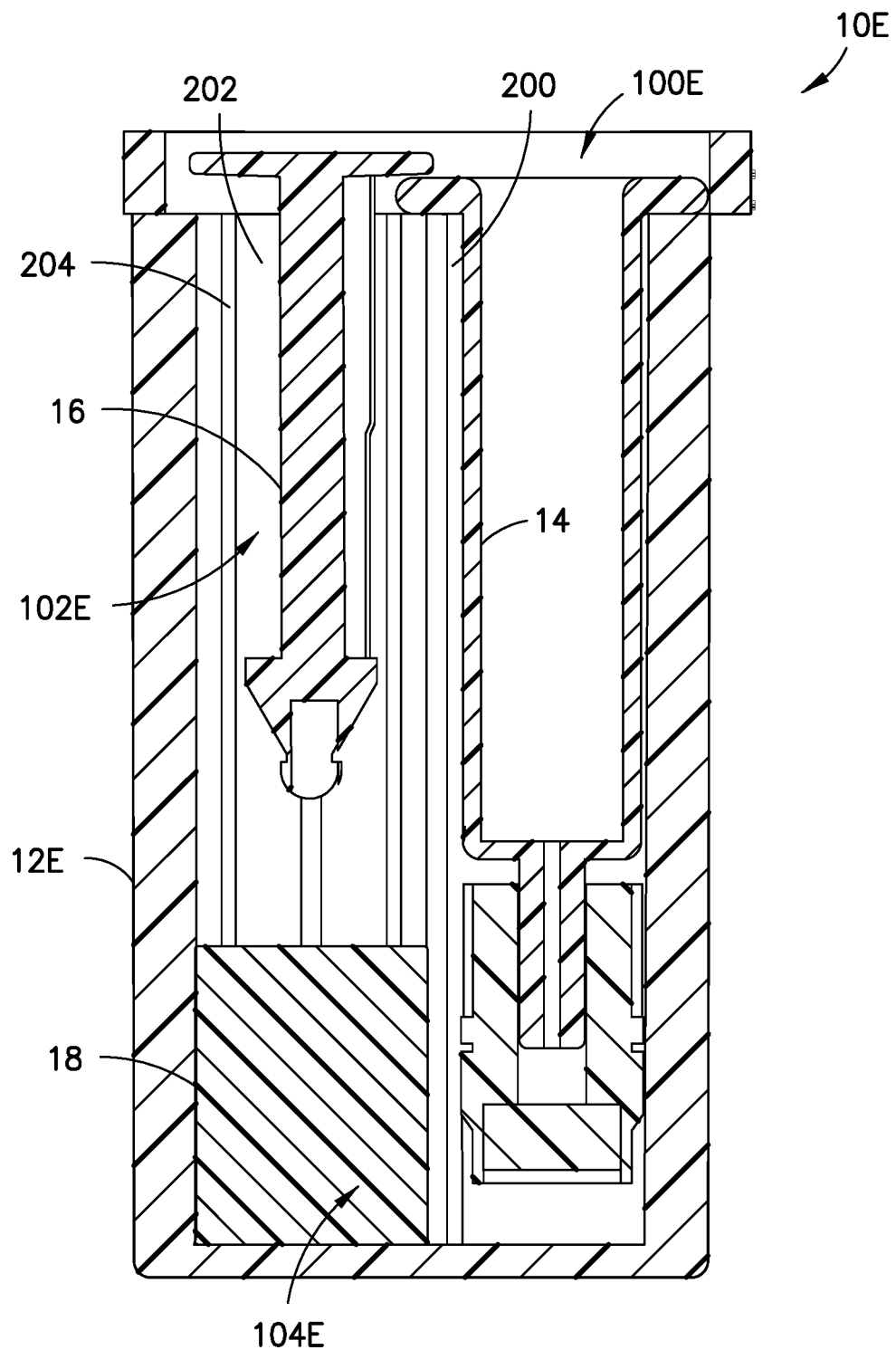
FIG. 70 is a cross-sectional view of the syringe packaging system of FIG. 69 in accordance with an embodiment of the present invention.

Next, oxygen absorber 18 is received within third compartment 104E of packaging member 12E, i.e., plunger rod and oxygen absorber container 202, such that oxygen absorber 18 is positioned vertically within plunger rod and oxygen absorber container 202 as shown in FIG. 70. To secure oxygen absorber 18 within third compartment 104E of packaging member 12E, oxygen absorber 18 is inserted or moved axially into plunger rod and oxygen absorber container 202 of packaging member 12E in a direction generally along arrow A (FIG. 1). As additional force is exerted on oxygen absorber 18 to axially move oxygen absorber 18 in the direction generally along arrow A within plunger rod and oxygen absorber container 202 of packaging member 12E, oxygen absorber 18 deforms ribs 204 outward until oxygen absorber 18 advances to the bottom portion of plunger rod and oxygen absorber container 202 of packaging member 12E. In this position, ribs 204 may abut, contact, or engage oxygen absorber 18 and lock or secure oxygen absorber 18 within plunger rod and oxygen absorber container 202 of third compartment 104E of packaging member 12E by an interference fit between ribs 204 and oxygen absorber 18. This configuration ensures that packaging member 12E provides a third compartment 104E that secures oxygen absorber 18 within packaging member 12E such that oxygen absorber 18 is prevented from being removed from packaging member 12E. This configuration also ensures that the oxygen absorber 18 is maintained within the third compartment 104E and is not able to slide towards the first compartment 100E. Next, syringe barrel 14 is inserted into syringe barrel container 200 of packaging member 12E as shown in FIG. 70. Next, plunger rod 16 is inserted into plunger rod and oxygen absorber container 202 of packaging member 12E as shown in FIG. 70.

In this manner, with the packaging member 12E enclosing the syringe barrel 14, the plunger rod 16, and the oxygen absorber 18, the oxygen absorber 18 is adapted to draw oxygen from the syringe barrel 14 and to absorb oxygen contained within the first compartment 100E, the second compartment 102E, and the third compartment 104E of the packaging member 12E.

Exemplary embodiments have been described above, however, those skilled in the art will appreciate that changes and modifications may be made to these embodiments without departing from the scope and spirit of the invention, which is defined by the claims.

What is claimed is:

1. A syringe packaging system, comprising:
a syringe barrel;
a plunger rod;
an oxygen absorber; and
a packaging member defining a first compartment, a second compartment, and a third compartment, the first compartment, the second compartment, and the third compartment distinct from each other and in gaseous communication, the first compartment structured to receive the syringe barrel therein, the second compartment structured to receive the plunger rod therein, and the third compartment structured to receive the oxygen absorber therein,
wherein with the packaging member enclosing the syringe barrel, the plunger rod, and the oxygen absorber, the oxygen absorber is adapted to draw oxygen from within the syringe barrel and to absorb oxygen contained within at least one of the first compartment, the second compartment, and the third compartment of the packaging member, and
wherein the packaging member includes an internal wall for securing the oxygen absorber within the packaging member, and a lid having an aperture, the lid securable to the internal wall.

2. The syringe packaging system of claim 1, wherein the lid is removably securable to the internal wall.

3. The syringe packaging system of claim 1, wherein the lid is secured to the internal wall via an interference fit.

4. The syringe packaging system of claim 1, wherein the lid includes opposing notches.

5. A syringe packaging system, comprising:
a syringe barrel;
a plunger rod;
an oxygen absorber;
a packaging member defining a first compartment, a second compartment, and a third compartment, the first compartment, the second compartment, and the third compartment distinct from each other and in gaseous communication, the first compartment structured to receive the syringe barrel therein, the second compartment structured to receive the plunger rod therein, and the third compartment structured to receive the oxygen absorber therein; and
a partition member receivable within the packaging member, the partition member and the packaging member defining the second compartment and the third compartment,
wherein with the packaging member enclosing the syringe barrel, the plunger rod, and the oxygen absorber, the oxygen absorber is adapted to draw oxygen from within the syringe barrel and to absorb oxygen contained within at least one of the first compartment, the second compartment, and the third compartment of the packaging member, and
wherein the packaging member includes a first protrusion and a second protrusion and the partition member is at least partially receivable between the first protrusion and the second protrusion.

6. The syringe packaging system of claim 5, wherein the first protrusion is a lateral bump.

7. The syringe packaging system of claim 5, wherein the second protrusion is a lateral bump.

8. The syringe packaging system of claim 5, wherein the first protrusion is disposed above the second protrusion.

9. The syringe packaging system of claim 5, wherein the partition member includes opposing notches.

10. The syringe packaging system of claim 5, wherein the partition member includes a plurality of gas holes.

* * * * *